US008445445B2

(12) United States Patent
Brennan et al.

(10) Patent No.: US 8,445,445 B2
(45) Date of Patent: May 21, 2013

(54) METHOD OF PROMOTING HAIR GROWTH USING FGFR4 EXTRACELLULAR DOMAINS

(75) Inventors: Thomas Brennan, San Jose, CA (US); Robert Dean, Alameda, CA (US); W. Michael Kavanaugh, Orinda, CA (US); Janine Powers, Alameda, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 13/496,182

(22) PCT Filed: Sep. 15, 2010

(86) PCT No.: PCT/US2010/048957
§ 371 (c)(1),
(2), (4) Date: Mar. 14, 2012

(87) PCT Pub. No.: WO2011/034940
PCT Pub. Date: Mar. 24, 2011

(65) Prior Publication Data
US 2012/0183541 A1    Jul. 19, 2012

Related U.S. Application Data

(60) Provisional application No. 61/288,190, filed on Dec. 18, 2009, provisional application No. 61/242,754, filed on Sep. 15, 2009.

(51) Int. Cl.
*A61K 38/00* (2006.01)
*A61K 38/18* (2006.01)
*A61K 38/16* (2006.01)
*C07K 14/475* (2006.01)
*C07K 14/50* (2006.01)

(52) U.S. Cl.
USPC ............ 514/20.7; 514/7.6; 514/9.1; 514/21.2

(58) Field of Classification Search
None
See application file for complete search history.

(56) References Cited

U.S. PATENT DOCUMENTS

| | | | |
|---|---|---|---|
| 5,229,501 A | 7/1993 | Keifer et al. |
| 5,288,855 A | 2/1994 | Bergonzoni et al. |
| 5,474,914 A | 12/1995 | Spaete |
| 5,486,462 A | 1/1996 | Rutter et al. |
| 5,707,632 A | 1/1998 | Williams et al. |
| 5,750,371 A | 5/1998 | Senoo et al. |
| 5,767,250 A | 6/1998 | Spaete |
| 5,863,888 A | 1/1999 | Dionne et al. |
| 6,255,454 B1 | 7/2001 | Keifer et al. |
| 6,344,546 B1 | 2/2002 | Dionne et al. |
| 6,350,593 B1 | 2/2002 | Williams et al. |
| 6,355,440 B1 | 3/2002 | Williams et al. |
| 6,384,191 B1 | 5/2002 | Williams et al. |
| 6,517,872 B1 | 2/2003 | Yayon et al. |
| 6,656,728 B1 | 12/2003 | Kavanaugh et al. |
| 6,844,168 B1 | 1/2005 | Keifer et al. |
| 7,045,550 B2 | 5/2006 | Fahl et al. |
| 7,135,311 B1 | 11/2006 | David et al. |
| 7,297,774 B2 | 11/2007 | Ullrich et al. |
| 7,306,789 B2 | 12/2007 | Doherty et al. |
| 7,335,641 B2 | 2/2008 | Kim et al. |
| 7,388,029 B2 | 6/2008 | DeLong et al. |
| 7,485,618 B2 | 2/2009 | Day et al. |
| 7,524,505 B2 | 4/2009 | Lin et al. |
| 7,589,060 B2 | 9/2009 | Imamura et al. |
| 7,645,609 B2 | 1/2010 | Follstad |
| 7,678,890 B2 | 3/2010 | Bosch et al. |
| 7,982,014 B2 | 7/2011 | Williams et al. |
| 8,119,770 B2 | 2/2012 | Blanche et al. |
| 8,173,134 B2 | 5/2012 | Bosch et al. |
| 8,338,569 B2 | 12/2012 | Marshall et al. |
| 2004/0063910 A1 | 4/2004 | Kavanaugh et al. |
| 2004/0115768 A1 | 6/2004 | Follstad |
| 2005/0187150 A1 | 8/2005 | Mohammadi et al. |
| 2006/0024705 A1 | 2/2006 | Centola et al. |
| 2006/0234347 A1 | 10/2006 | Harding et al. |
| 2006/0286102 A1 | 12/2006 | Jin et al. |
| 2007/0248604 A1 | 10/2007 | Desnoyers et al. |
| 2007/0248605 A1 | 10/2007 | Hestir et al. |
| 2008/0139469 A1 | 6/2008 | Imamura et al. |
| 2008/0171689 A1 | 7/2008 | Williams et al. |
| 2010/0087627 A1 | 4/2010 | Marshall et al. |
| 2012/0128672 A1 | 5/2012 | Keer |
| 2012/0237511 A1 | 9/2012 | Long et al. |
| 2012/0251538 A1 | 10/2012 | Harding et al. |
| 2012/0301921 A1 | 11/2012 | Williams et al. |
| 2013/0004492 A1 | 1/2013 | Marshall et al. |

FOREIGN PATENT DOCUMENTS

| | | |
|---|---|---|
| EP | 0 545 343 A1 | 6/1993 |
| EP | 1910542 B2 | 2/2009 |
| EP | 2083081 A1 | 7/2009 |
| EP | 2 127 674 A1 | 12/2009 |
| WO | WO 91/00916 | 1/1991 |
| WO | WO 91/11459 | 8/1991 |

(Continued)

OTHER PUBLICATIONS du Cros DL, J. Investig. Dermatol., 101:106S-113S, 1993.*
Rosenquist TA, et al. Developmental Dynamics, 205:379-386, 1996.*
Akimoto et al., "Fibroblast growth factor 2 promotes microvessel formation from mouse embryonic aorta" Am. J. Physiol. Cell Physiol., vol. 284, No. 2, 2003, pp. C371-C377.
Anderson et al., "Apert syndrome mutations in fibroblast growth factor receptor 2 exhibit increased affinity for FGF ligand" Human Molecular Genetics, vol. 7, No. 9, 1998, pp. 1475-1483.
Andre et al., "Molecular Characterization of Breast Cancer with High-Resolution Oligonucleotide Comparative Genomic Hybridization Array," Clin Cancer Res, 2009, 15(2): 441-451.
Auguste et al., "Inhibition of fibroblast growth factor-fibroblast growth factor receptor activity in glioma cells impedes tumor growth by both angiogenesis-dependent and -independent mechanisms" Cancer Research, vol. 61, Feb. 15, 2001, pp. 1717-1726.
Baker et al., "Metabolic control of recombinant protein N-glycan processing in NS0 and CHO cells" Biotechnology and Bioengineering, vol. 73, No. 3, May 5, 2001, pp. 188-202.

(Continued)

*Primary Examiner* — Robert Landsman
(74) *Attorney, Agent, or Firm* — Casimir Jones, S.C.

(57) ABSTRACT

The present invention relates to a method of promoting hair growth comprising administering a fibroblast growth factor receptor 4 (FGFR4) extracellular domain (ECD), including native FGFR4 ECDs, variants, fragments, and fusion molecules, to a subject in an amount sufficient to promote hair growth.

22 Claims, 7 Drawing Sheets

FOREIGN PATENT DOCUMENTS

| | | |
|---|---|---|
| WO | WO 2004/006949 A1 | 1/2004 |
| WO | WO 2004/110487 A1 | 12/2004 |
| WO | WO 2005/113596 A2 | 12/2005 |
| WO | WO 2005/115363 A2 | 12/2005 |
| WO | WO 2006/081430 A2 | 8/2006 |
| WO | WO 2006/113277 A2 | 10/2006 |
| WO | WO 2007/014123 A2 | 2/2007 |
| WO | WO 2007/059574 A1 | 5/2007 |
| WO | WO 2007/134210 A2 | 11/2007 |
| WO | WO 2008/065543 A2 | 6/2008 |
| WO | WO 2008/118877 A2 | 10/2008 |
| WO | WO 2011/060333 A1 | 5/2011 |
| WO | WO 2011/084711 | 7/2011 |

OTHER PUBLICATIONS

Ballinger et al., "Semirational design of a potent, artificial agonist of fibroblast growth factor receptors" Nature Biotechnology, vol. 17, Dec. 1999, pp. 1199-1204.

Bansal et al., "The Molecular Biology of Endometrial Cancers and the Implications for Pathogenesis, Classification, and Targeted Therapies," Cancer Control, 2009, 16(1):8-13.

Bass et al., "SOX2 Is an Amplified Lineage Survival Oncogene in Lung and Esophageal Squamous Cell Carcinomas," Nat. Genet., 2009, 41(11): 1238-1242, including supplemental information (15 pages).

Beroukhim et al., "The landscape of somatic copy-number alteration across human cancers," Nature, 2010, 463: 899-905.

Bjornsson et al., Pharmacokinetics of Heparin. II. Studies of Time Dependence in Rats, The Journal of Pharmacology and Experimental Therapeutics, vol. 210, No. 2, Apr. 1979, pp. 243-246.

Byron and Pollock, "FGFR2 as a molecular target in endometrial cancer," Future Oncol, 2009, 5(1):27-32.

Byron et al., "Inhibition of Activated Fibroblast Growth Factor Receptor 2 in Endometrial Cancer Cells Induces Cell Death Despite PTEN Abrogation," Cancer Res, 2008, 68(17):6902-6907.

Byron et al., "FGFR2 mutations are rare across histologic subtypes of ovarian cancer," Gynecologic Oncology, 2010, 117(1):125-129.

Celli et al., "Soluble dominant-negative receptor uncovers essential roles for fibroblast growth factors in multi-organ induction and patterning" The EMBO Journal, vol. 17, No. 6, Mar. 16, 1998, pp. 1642-1655.

Chellaiah et al., "Mapping ligand binding domains in chimeric fibroblast growth factor receptor molecules" J. Biol. Chem., vol. 274, No. 49, Dec. 3, 1999, pp. 34785-34794.

Cheon et al., "High-affinity binding sites for related fibroblast growth factor ligands reside within different receptor immunoglobulin-like domains" Proc. Natl. Acad. Sci., vol. 91, Feb. 1994, pp. 989-993.

Choo et al., SPdb—a Signal Peptide Database, BMC Bioinformatics, vol. 6, No. 249, Oct. 2005, pp. 1-8.

Compagni et al., "Fibroblast growth factors are required for efficient tumor angiogenesis" Cancer Research, vol. 60, Dec. 15, 2000, pp. 7163-7169.

Coughlin et al., "Acidic and basic fibroblast growth factors stimulate tyrosine kinase activity in vivo" J. Biol. Chem., vol. 263, No. 2, Jan. 15, 1988, pp. 988-993.

Courjal et al., "Comparative Genomic Hybridization Analysis of Breast Tumors with Predetermined Profiles of DNA Amplification," Cancer Res. 1997, 57(19):4368-77.

Cuny et al., "Relating genotype and phenotype in breast cancer: an analysis of the prognostic significance of amplification at eight different genes or loci and of p53 mutations," Cancer Res. 2000; 60(4):1077-83.

Dutt et al., "Drug-sensitive FGFR2 mutations in endometrial carcinoma," PNAS, 2008, 105(25):8713-8717.

Dutt et al., "Inhibitor-Sensitive FGFR1 Amplification in Human Non-Small Cell Lung Cancer," 2011, PLoS ONE, 6(6): e20351, 10 pages.

Elbauomy Elsheikh et al., "FGFR1 amplification in breast carcinomas: a chromogenic in situ hybridisation analysis," Breast Cancer Research 2007, 9:R23, 12 pages.

Ezzat et al., "A soluble dominant negative fibroblast growth factor receptor 4 isoform in human MCF-7 breast cancer cells" Biochem. Biophys. Res. Comm., vol. 287, No. 1, 2001, pp. 60-65.

Feige et al., "Glycosylation of the basic fibroblast growth factor receptor" J. Biol. Chem., vol. 263, No. 28, Oct. 5, 1988, pp. 14023-14029.

Gatius et al., "FGFR2 alterations in endometrial carcinoma," Modern Pathology, 2011, 24:1500-1510.

Gelsi-Boyer et al., "Comprehensive Profiling of 8p11-12 Amplification in Breast Cancer," Mol Cancer Res 2005;3(12): 655-667.

Genbank Accession No. X76885, 1994, 2 pages.

Genbank Accession No. Q90330, Nov. 1, 1996, 6 pages.

Gowardhan et al., "Evaluation of the fibroblast growth factor system as a potential target for therapy in human prostate cancer" British Journal of Cancer, vol. 92, Jan. 18, 2005, pp. 320-327.

Grossman et al., "Expression of human thyrotropin in cell lines with different glycosylation patterns combined with mutagenesis of specific glycosylation sites" J. Biol. Chem., vol. 270, No. 49, Dec. 8, 1995, pp. 29378-29385.

Guillonneau et al., "Fibroblast growth factor (FGF) soluble receptor 1 acts as a natural inhibitor of FGF2 neurotrophic activity during retinal degeneration" Molecular Biology of the Cell, vol. 9, Oct. 1998, pp. 2785-2802.

Hanneken et al., "Identification of soluble forms of the fibroblast growth factor receptor in blood" Proc. Natl. Acad. Sci., vol. 91, Sep. 1994, pp. 9170-9174.

Hanneken et al., "Soluble forms of the high-affinity fibroblast growth factor receptor in human vitreous fluid" Investigative Opthalmology & Visual Science, vol. 36, No. 6, May 1995, pp. 1192-1196.

Hanneken et al., "Structural characterization of the circulating soluble FGF receptors reveals multiple isoforms generated by secretion and ectodomain shedding" FEBS Letters, vol. 489, 2001, pp. 176-181.

Harding et al., "Role of VEGF, PDGF and FGF in glioblastoma progression as determined by soluble decoy receptor expression in preclinical models" Cell Genesys, Inc., Abstract No. 3030, presented at the AACR Annual Meeting, Apr. 16-20, 2005, 1 page.

Harding et al., "Preclinical Efficacy of FP-1039 (FGFR1:Fc) in Endometrial Carcinoma Models with Activating Mutations in FGFR2," AACR 101st Annual Meeting Poster (Apr. 17-21, 2010).

Ibrahimi et al., "Biochemical analysis of pathogenic ligand-dependent FGFR2 mutations suggests distinct pathophysiological mechanisms for craniofacial, and limb abnormalities," Human Molecular Genetics, 2004, 13(19):2313-2324.

Johnson et al., "Diverse forms of a receptor for acidic and basic fibroblast growth factors" Molecular and Cellular Biology, vol. 10, No. 9, Sep. 1990, pp. 4728-4736.

Johnson et al, "The human fibroblast growth factor receptor genes: a common structural arrangement underlies the mechanisms for generating receptor forms that differ in their third immunoglobulin domain" Molecular and Cellular Biology, vol. 11, No. 9, Sep. 1991, pp. 4627-4634.

Kan et al., "Divalent cations and heparin-heparan sulfate cooperate to control assembly and activity of the fibroblast growth factor receptor complex" J. Biol. Chem., vol. 271, No. 42, Oct. 18, 1996, pp. 26143-26148.

Katoh, "Cancer genomics and genetics of FGFR2 (Review)," International Journal of Oncology, 2008, 33:233-237.

Katoh, "FGFR2 Abnormalities Underlie a Spectrum of Bone, Skin, and Cancer Pathologies," Journal of Investigative Dermatology, 2009, 129:1861-1867.

Kaufman et al., "Characterization of ligand binding to immobilized biotinylated extracellular domains of three growth factor receptors" Anal. Biochem., vol. 211, No. 2, Jun. 1993, pp. 261-266.

Kawano et al., "Comprehensive Analysis of FGF and FGFR Expression in Skin: FGF18 Is Highly Expressed in Hair Follicles and Capable of Inducing Anagen from Telogen Stage Hair Follicles," J Invest Dermatol 124:877-885, 2005.

Keer et al., "Enrolling a Rare Patient Population: Establishing Proof of Concept for FP-1039, an FGF 'Trap,' in Endometrial Cancer Patients with the S252W FGFR2 Mutation," American Society of Clinical Oncology 2010, Annual Meeting, Jun. 4-8, 2010, Chicago, IL.

Keifer et al., "Molecular cloning of a human basic fibroblast growth factor receptor cDNA and expression of a biologically active extracellular domain in a baculovirus system" Growth Factors, vol. 5, 1991, pp. 115-127.

Kleeff et al., "Adenovirus-mediated transfer of a truncated fibroblast growth factor (FGF) type I receptor blocks FGF-2 signaling in multiple pancreatic cancer cell lines" Pancreas, vol. 28, No. 1, Jan. 2004, pp. 25-30.

Kwabi-Addo et al., "The role of fibroblast growth factors and their receptors in prostate cancer" Endocrine-Related Cancer, vol. 11, No. 4, Dec. 2004, pp. 709-724.

Lazar et al., "Transforming Growth Factor alpha: Mutation of Aspartic Acid 47 and Leucine 48 Results Different Biological Activities," Mol Cell Biol, 1988, 8(3):1247-1252.

Lee et al., "Purification and complementary DNA cloning of a receptor for basic fibroblast growth factor" Science, vol. 245, No. 4913, Jul. 7, 1989, pp. 57-60.

Lee et al., "Molecular profiles of EGFR, K-ras, c-met, and FGFR in pulmonary pleomorphic carcinoma, a rare lung malignancy," J. Cancer Res. Clin. Oncol., May 28, 2011, 9 pages.

Levi et al., "Matrix metalloproteinase 2 releases active soluble ectodomain of fibroblast growth factor receptor 1", XP-002413740, Proc. Natl. Acad. Sci., USA, vol. 93, pp. 7069-7074, (Jul. 1996).

Li et al., "Cell transformation by fibroblast growth factors can be suppressed by truncated fibroblast growth factor receptors" Molecular and Cellular Biology, vol. 14, No. 11, Nov. 1994, pp. 7660-7669.

Liu et al, "Utilization of Unlabeled Probes for the Detection of Fibroblast Growth Factor Receptor 2 Exons 7 and 12 Mutations in Endometrial Carcinoma," Appl Immunohistochem Mol Morphol, 2011, 19(4):341-346.

Liuzzo et al., "Human leukemia cell lines bind basic fibroblast growth factor (FGF) on FGF receptors and heparin sulfates: downmodulation of FGF receptors by phorbol ester" Blood, vol. 87, No. 1, Jan. 1, 1996, pp. 245-255.

Long et al. "Abstract #2789: Antitumor efficacy of FP-1039, a soluble FGF receptor 1:Fc conjugate, as a single agent or in combination with anticancer drugs," Proceedings of the American Association for Cancer Research, Apr. 18-22, 2009 Denver, CO.

Long et al. "Preclinical antitumor efficacy of FP-1039, a soluble FGF receptor 1:Fc conjugate, as a single agent or in combination with anticancer drugs," Proceedings of the American association for Cancer Research, Apr. 17-22, 2009 Denver, CO.

Lopez et al., "A novel type I fibroblast growth factor receptor activates mitogenic signaling in the absence of detectable tyrosine phosphorylation of FRS2" J. Biol. Chem., vol. 275, No. 21, May 26, 2000, pp. 15933-15939.

Lundin et al., "Selectively desulfated heparin inhibits fibroblast growth factor-induced mitogenicity and angiogenesis" J. Biol. Chem., vol. 275, No. 32, Aug. 11, 2000, pp. 24653-24660.

Mansukhani et al., "A murine fibroblast growth factor (FGF) receptor expressed in CHO cells is activated by basic FGF and Kaposi FGF" Proc. Natl. Acad. Sci., vol. 87, Jun. 1990, pp. 4378-4382.

Marics et al., "FGFR4 signaling is a necessary step in limb muscle differentiation," Development, 2002, 129:4559-4569.

Marshall et al., "Fibroblast Growth Factor Receptors Are Components of Autocrine Signaling Networks in Head and Neck Squamous Cell Carcinoma Cells," 2011, 17(15): 5016-5025.

Meijer et al., Fibroblast Growth Factor Receptor 4 Predicts Failure on Tamoxifen Therapy in Patients with Recurrent Breast Cancer, Endocrine-Related Cancer, vol. 15, 2008, pp. 101-111.

Moloney et al., "Exclusive paternal origin of new mutations in Apert syndrome," Nature Genetics, 1996, 13:48-53.

Ogawa et al., "Anti-tumor angiogenesis therapy using soluble receptors: enhanced inhibition of tumor growth when soluble fibroblast growth factor receptor-1 is used with soluble vascular endothelial growth factor receptor" Cancer Gene Therapy, vol. 9, Aug. 2002, pp. 633-640.

Ornitz et al., "Heparin is required for cell-free binding of basic fibroblast growth factor to a soluble receptor and for mitogenesis in whole cells" Molecular and Cellular Biology, vol. 12, Jan. 1992, pp. 240-247.

Ornitz et al., "Receptor specificity of the fibroblast growth factor family" J. Biol. Chem., vol. 271, No. 25, Jun. 21, 1996, pp. 15292-15297.

Otto et al., "Sialylated complex-type $N$-glycans enhance the signaling activity of soluble intercellular adhesion molecule-1 in mouse astrocytes" J. Biol. Chem., vol. 279, No. 34, Aug. 20, 2004, pp. 35201-35209.

Pasquale et al., "Identification of a developmentally regulated protein-tyrosine kinase by using anti-phosphotyrosine antibodies to screen a cDNA expression library" Proc. Natl. Acad. Sci., vol. 86, Jul. 1989, pp. 5449-5453.

Plotnikov et al., "Crystal structures of two FGF-FGFR complexes reveal the determinants of ligand-receptor specificity" Cell, vol. 101, May 12, 2000, pp. 413-424.

Pollock et al., "Frequent activating FGFR2 mutations in endometrial carcinomas parallel germline mutations associated with craniosynostosis and skeletal dysplasia syndromes," Oncogene, 2007, 26:7158-7162.

Powell et al., "Fibroblast growth factor receptors 1 and 2 interact differently with heparin-heparan sulfate" J. Biol. Chem., vol. 277, No. 32, Aug. 9, 2002, pp. 28554-28563.

Powers et al., "Fibroblast growth factors, their receptors and signaling", XP-002165147, Endocrine-Related Cancer, 7, pp. 165-197, (2000).

Rang et al, "Cancer chemotherapy," *Rang and Dale's Pharmacology*, Churchill Linvingston Elsevier, 2008, pp. 718-735.

Reis-Filho et al., "FGFR1 Emerges as a Potential Therapeutic Target for Lobular Breast Carcinomas," 2006, Clin. Cancer Res. 12(22): 6652-6662.

Roghani et al., "Heparin increases the affinity of basic fibroblast growth factor for its receptor but is not required for binding" J. Biol. Chem., vol. 269, No. 6, Feb. 11, 1994, pp. 3976-3984.

Ruta et al., "A novel protein tyrosine kinase gene whose expression is modulated during endothelial cell differentiation" Oncogene, 1988, vol. 3, pp. 9-15.

Sahadevan et al., Selective Over-expression of Fibroblast Growth Factor Receptors I and 4 in Clinical Prostate Cancer, Journal of Pathology, vol. 213, Jul. 2007, pp. 82-90.

Sanchez-Heras et al., "The fibroblast growth factor receptor acid box is essential for interactions with N-cadherin and all of the major isoforms of neural cell adhesion molecules," J Biol Chem, 2006, 281(46):35208-16.

Shamim et al., "Sequential roles for Fgf4, En1 and Fgf8 in specification and regionalization of the midbrain" Development, vol. 126, Feb. 1999, pp. 945-959.

Smith et al., "The asparagine-linked oligosaccharides on tissue factor pathway inhibitor terminate with $SO_4$-4GalNAc$\beta$1,4GlcNAc$\beta$1,2Man$\alpha$" J. Biol. Chem., vol. 267, No. 27, Sep. 25, 1992, pp. 19140-19146.

St. Bernard et al., "Fibroblast growth factor receptors as molecular targets in thyroid carcinoma" Endocrinology, vol. 146, No. 3, 2005, pp. 1145-1153.

St. Bernard et al., "Fibroblast growth factor receptors as molecular targets in thyroid carcinoma" Endocrinology, vol. 10, Nov. 24, 2004, pp. 1-26 and 6 pgs. figures.

Sugiura et al., "Co-expression of aFGF and FGFR-1 is predictive of a poor prognosis in patients with esophageal squamous cell carcinoma," Oncology Reports, 2007, 17: 557-564.

Tolcher et al., "Preliminary Results of a Phase 1 Study of FP-1039 (FGFR1:Fc), A Novel Antogonist of Multiple Fibroblast Growth Factor (FGF) Ligands, in Patients With Advanced Malignancies," 2009 AACR-EORTC-NCI Molecular Targets and Cancer Therapeutics Conference Poster (Nov. 15-18, 2009).

Tolcher et al., "Preliminary Results of a Dose Escalation Study of the Fibroblast Growth Factor (FGF) "trap" FP-1039 (FGFR1:Fc) In Patients With Advanced Malignancies," 22nd EORTC-NCI-AACR Symposium on Molecular Targets and Cancer Therapeutics Poster (Nov. 16-19, 2010).

Tolcher et al., "Preliminary results of a dose escalation study of the Fibroblast Growth Factor (FGF) "trap" FP-1039 (FGFR1:Fc) in patients with advanced malignancies," *European Journal of Cancer, Supplement*, 8(7): 121, Abstract No. 381 (Nov. 18, 2010).

Tomlinson et al., "Alternative splicing of fibroblast growth factor receptor 3 produces a secreted isoform that inhibits fibroblast growth factor-induced proliferation and is repressed in urothelial carcinoma cell lines" Cancer Research, vol. 65, No. 22, Nov. 15, 2005, pp. 10441-10449.
Trueb et al., "Characterization of FGFRL1, a novel fibroblast growth factor (FGF) receptor preferentially expressed in skeletal tissues" J. Biol. Chem., vol. 278, No. 36, Sep. 5, 2003, pp. 33857-33865.
Tucker et al., "A novel approach for inhibiting growth factor signalling in murine tooth development" Eur. J. Oral Sci., vol. 106 (suppl. 1), 1998, pp. 122-125.
Tuominen et al., "Expression and glycosylation studies of human FGF Receptor 4" Protein Expression and Purification, vol. 21, Mar. 2001, pp. 275-285.
Turner et al., "FGFR1 Amplification Drives Endocrine Therapy Resistance and Is a Therapeutic Target in Breast Cancer," 2010, 70(5): 2085-2094.
Turner et al., "A Therapeutic Target for Smoking-Associated Lung Cancer," 2010, Science Trans. Med. 2(62): 62ps56, 4 pages.
Ueno et al., "A truncated form of fibroblast growth factor receptor 1 inhibits signal transduction by multiple types of fibroblast growth factor receptor" J. Biol. Chem., vol. 267, No. 3, Jan. 25, 1992, pp. 1470-1476.
Van Den Nieuwenhof et al., "Recombinant glycodelin carrying the same type of glycan structures as contraceptive glycodelin-A can be produced in human kidney 293 cells but not in Chinese hamster ovary cells" Eur. J. Biochem., vol. 267, Aug. 2000, pp. 4753-4762.
Voortman et al., "Array comparative genomic hybridization-based characterization of genetic alterations in pulmonary neuroendocrine tumors," 2010, PNAS, 107(29): 13040-13045.
Wagner et al., "Suppression of fibroblast growth factor receptor signaling inhibits pancreatic cancer growth in vitro and in vivo" Gastroenterology, vol. 114, Apr. 1998, pp. 798-807.
Wang et al., "Purification and characterization of a functional soluble fibroblast growth factor receptor 1" Biochem. Biophys. Res. Comm., vol. 203, No. 3, Sep. 30, 1994, pp. 1781-1788.
Wang et al., "A natural kinase-deficient variant of fibroblast growth factor receptor 1" Biochemistry, Vo. 35, 1996, pp. 10134-10142.
Weiss et al., "Frequent and Focal FGFR1 Amplification Associates with Therapeutically Tractable FGFR1 Dependency in Squamous Cell Lung Cancer," Science Trans. Med., 2010, 2(62): 62ra93, 8 pages.
Wells, "Additivity of Mutational Effects in Proteins," Biochemistry, 1990, 29(37):8509-8517.
Werner et al., "Differential splicing in the extracellular region of fibroblast growth factor receptor 1 generates receptor variants with different ligand-binding specificities" Molecular and Cellular Biology, vol. 12, No. 1, Jan. 1992, pp. 82-88.
Williams et al., "Activation of the FGF receptor underlies neurite outgrowth stimulated by L1, N-CAM, and N-Cadherin" Neuron, vol. 13, Sep. 1994, pp. 583-594.
Ye et al., "FGF and Shh signals control dopaminergic and serotonergic cell fate in the anterior neural plate" Cell, vol. 93, May 29, 1998, pp. 755-766.
Yu et al., "Loss of fibroblast growth factor receptor 2 ligand-binding specificity in Apert syndrome," PNAS, 2000, 97(26):14536-14541.
Zhang et al., Receptor Specificity of the Fibroblast Growth Factor Family: The Complete Mammalian FGF Family, The Journal of Biological Chemistry, vol. 281, No. 23, Jun. 9, 2006, pp. 15694-15700.
Zhang et al., "FP-1039 (FGFR1:Fc), A Soluble FGFR1 Receptor Antagonis, Inhibits Tumor Growth and Angiogenesis," AACR-NCI-EORTC International Conference, Oct. 22-26, 2007, San Francisco, CA.
Zheng et al. "Enhanced efficacy in anti-tumour activity by combined therapy of recombinant FGFR-1 related angiogenesis and low-dose cytotoxic agent," European Journal of Cancer, vol. 43, No. 14, Sep. 14, 2007, pp. 2134-2139.
File History for U.S. Appl. No. 11/791,889, filed May 30, 2007.
File history for U.S. Appl. No. 12/535,479, filed Aug. 4, 2009.
File History for U.S. Appl. No. 12/652,720, filed Jan. 5, 2010.
File History for U.S. Appl. No. 13/157,712, filed Jun. 10, 2011.
File history for U.S. Appl. No. 13/227,398, filed Sep. 7, 2011.
File History for U.S. Appl. No. 13/296,161, filed Nov. 14, 2011.
File History for U.S. Appl. No. 13/296,168, filed Nov. 14, 2011.
File History for U.S. Appl. No. 13/438,638, filed Apr. 3, 2012.
File History for U.S. Appl. No. 13/509,068, filed Jun. 13, 2012.
File History for U.S. Appl. No. 13/675,255, filed Nov. 13, 2012.
File History for U.S. Appl. No. 13/515,429, filed Nov. 21, 2012.
International Search Report and Written Opinion mailed Mar. 8, 2012 for PCT/US2009/052704, filed Aug. 4, 2009.
International Search Report and Written Opinion of the International Searching Authority, mailed Sep. 18, 2007, for International Application No. PCT/US2006/028597, 23 pages.
International Preliminary Report on Patentability, mailed Jan. 22, 2008, for International Application No. PCT/US2006/028597, 14 pages.
International Search Report and Written Opinion, mailed Feb. 4, 2011, for International Patent Application PCT/US2010/056627, 15 pages.
International Search Report and Written Opinion of the International Searching Authority, mailed Feb. 3, 2012, for International Application No. PCT/US2010/061157, 12 pages.
International Search Report and Written Opinion of the International Searching Authority, mailed Jan. 31, 2012, for International Application No. PCT/US2011/060661, 16 pages.
International Search Report and Written Opinion of the International Searching Authority, mailed Apr. 12, 2012, for International Application No. PCT/US2011/060666, 20 pages.
European Search Report, mailed Jun. 5, 2009, in European Application No. 09075061.3, 2 pages.
Invitation to Pay Additional Fees and, Where Applicable, Protest Fee, for International Patent Application No. PCT/US2010/048957, mailed Dec. 3, 2010 (2 pages).
B.-M. Loo et al., "Production and characterization of the extracellular domain of recombinant human fibroblast growth factor receptor 4," Intl. J. Biochem. Cell Biol., 32: 489-497 (2000).
Notification of Transmittal of the International Search Report and the Written Opinion of the International Searching Authority, or the Declaration, for International Patent App. No. PCT/US2010/048957, mailed Jan. 24, 2011 (11 pages).
E. Bodó et al., "Dissecting the Impact of Chemotherapy on the Human Hair Follicle," Am. J. Pathol., 171(4): 1153-1167 (2007).
V. A. Botchkarev, "Stress and the Hair Follicle: Exploring the Connections," Am. J. Pathol., 162(3): 709-712 (2003).
V. A. Botchkarev et al., "Neurotrophins in Skin Biology and Pathology," J. Invest. Dermatol., 126: 1719-1727 (2006).
M.Y. Fessing et al., "Involvement of the Edar Signaling in the Control of Hair Follicle Involution (Catagen)," Am. J. Path., 169(6): 2075-2084 (2006).
A. Gilhar et al., "Lymphocytes, neuropeptides, and genes involved in alopecia areata," J. Clinical Invest., 117(8): 2019-2027 (2007).
S. Harrison et al., "Diffuse hair loss: Its triggers and management," Cleveland Clinical J. Med., 76(6): 361-367 (2009).
O. A. Ibrahimi et al., "Structural basis for fibroblast growth factor receptor 2 activation in Apert syndrome," Proc. Natl. Acad. Sci., USA, 98(13): 7182-7187 (2001).
O. A. Ibrahimi et al., "Proline to arginine mutations in FGF receptors 1 and 3 result in Pfeiffer and Muenke craniosynostosis syndromes through enhancement of FGF binding affinity," Hum. Mol. Genet., 13: 69-78 (2004).
O. A. Ibrahimi et al., "Analysis of Mutations in Fibroblast Growth Factor (FGF) and a Pathogenic Mutation in FGF Receptor (FGFR) Provides Direct Evidence for the Symmetric Two-End Model for FGFR Dimerization," Mol. Cell. Biol., 25(2): 671-684 (2005).
T. Ito et al. "Maintenance of Hair Follicle Immune Privilege is Linked to Prevention of NK Cell Attack," J. Invest. Dermatol., 128: 1196-1206 (2008).
K. K. Lin et al., "Circadian Clock Genes Contribute to the Regulation of Hair Follicle Cycling," PLoS Genet., 5(7): e1000573 (14 pages) (2009).
M. A. Novak et al., "Alopecia: Possible Causes and Treatments, Particularly in Captive Nonhuman Primates," Comparative Medicine, 59(1): 18-26 (2009).

S. K. Olsen et al., "Insights into the molecular basis for fibroblast growth factor receptor autoinhibition and ligand-binding promiscuity," Proc. Natl. Acad. Sci., USA, 101(4): 935-940 (2004).

Pellegrini et al., "Crystal structure of fibroblast growth factor receptor ectodomain bound to ligand and heparin," Nature, 407: 1029-1034 (2000).

E. M. J. Peters et al., "Probing the Effects of Stress Mediators on the Human Hair Follicle," Am. J. Pathol., 171(6): 1872-1886 (2007).

M. V. Plikus et al., "Complex Hair Cycle Domain Patterns and Regenerative Hair Waves in Living Rodents," J. Invest. Dermatol., 128: 1071-1080 (2008).

A. N. Plotnikov et al., "Structural Basis for FGF Receptor Dimerization and Activation," Cell, 98: 641-650 (1999).

R. M. Porter, "Mouse models for human hair loss disorders," J. Anat., 202: 125-131 (2003).

S. C. Robertson et al., "Activating mutations in the extracellular domain of the fibroblast growth factor receptor 2 function by disruption of the disulfide bond in the third immunoglobulin-like domain," Proc. Natl. Acad. Sci., USA, 95: 4567-4572 (1998).

J. Schlessinger et al., "Crystal Structure of the Ternary FGF-FGFR-Herparin Complex Reveals a Dual Role for Heparin in FGFR Binding and Dimerization," Molecular Cell, 6: 743-750 (2000).

M. R. Schneider et al., "Betacellulin Regulates Hair Follicle Development and Hair Cycle Induction and Enhances Angiogenesis in Wounded Skin," J. Invest. Dermatol., 128: 1256-1265 (2008).

A. A. Sharov et al., "Fas Signaling is Involved in the Control of Hair Follicle Response to Chemotherapy," Cancer Res, 64: 6266-6270 (2004).

A. A. Sharov et al., "Changes in Different Melanocyte Populations During Hair Follicle Involution (Catagen)," J. Invest. Dermatol., 125: 1259-1267 (2005).

A. A. Sharov et al., "Bone morphogenetic protein (BMP) signaling controls hair pigmentation by means of cross-talk with the melanocortin receptor-1 pathway," Proc. Natl. Acad. Sci., USA, 102(1): 93-98 (2005).

A. A. Sharov et al., "Bone morphogenetic protein signaling regulates the size of hair follicles and modulates the expression of cell cycle-associated genes," Proc. Natl. Acad. Sci., USA, 103(48): 18166-18171 (2006).

F. Siebenhaar et al., "Substance P as an Immunomodulatory Neuropeptide in a Mouse Model for Autoimmune Hair Loss (Alopecia Areata)," J. Invest. Dermatol., 127: 1489-1497 (2007).

A. Slominski et al., "Skin as an endocrine organ: implications for its function," Drug Discov. Today Dis. Mech., 5(2): 137-144 (2008).

D. J. Stauber et al., "Structural interaction of fibroblast growth factor receptor with its ligands," Proc. Natl. Acad. Sci., USA, 97(1): 49-54 (2000).

F. Wang et al., "Alternately Spliced $NH_2$-terminal Immunoglobulin-like Loop I in the Ectodomain of the Fibroblast Growth Factor (FGF) Receptor 1 Lowers Affinity for both Heparin and FGF-1," J. Biol. Chem, 270(17): 10231-10235 (1995).

* cited by examiner

METHOD OF PROMOTING HAIR GROWTH USING FGFR4 EXTRACELLULAR DOMAINS

This application is the U.S. national stage of International Application No. PCT/US2010/048957, filed Sep. 15, 2010. This application also claims priority to U.S. Provisional Application No. 61/288,190, filed Dec. 18, 2009, and to U.S. Provisional Application No. 61/242,754, filed Sep. 15, 2009. Those applications are incorporated by reference herein.

TECHNICAL FIELD

The present invention relates to a method of promoting hair growth comprising administering a fibroblast growth factor receptor 4 (FGFR4) extracellular domain (ECD), including native FGFR4 ECDs, variants, fragments, and fusion molecules, to a subject in an amount sufficient to promote hair growth.

BACKGROUND AND SUMMARY

Hair growth problems are wide-spread. In addition to pattern baldness, which may occur in both males and females, hair loss can be induced by drugs, such as chemotherapy drugs, or by chemical or physical damage, such as by certain hair products or styling techniques. Hair loss may also be triggered by systemic diseases, autoimmune conditions, nutritional deficiencies and physical stress, such as during pregnancy, due to surgery, or due to weight loss. It may also be induced by psychological stress.

Available treatments to promote hair growth are limited. For example, minoxidil, while relatively safe, is only moderately effective. The 5-alpha reductase inhibitor finasteride is not indicated for women or children and has negative side effects. The use of certain polypeptides to promote hair growth has been suggested. (See e.g., U.S. Pat. No. 7,335,641, U.S. Pat. No. 7,524,505, U.S. Pat. No. 7,485,618, and U.S. Patent Application No. 2008/0139469, now U.S. Pat. No. 7,589,060.) To date, the only permanent solution to hair loss is hair transplant surgery, which is both expensive and invasive. Thus, there remains a need in the art for additional agents for promoting hair growth. The present invention relates to a method of promoting hair growth comprising administering a fibroblast growth factor receptor 4 (FGFR4) extracellular domain (ECD) to a subject in an amount sufficient to promote hair growth.

Fibroblast growth factors (FGFs) and their receptors (FGFRs) are a highly conserved group of proteins with diverse functions. The FGFR family comprises four major types of receptors, FGFR1, FGFR2, FGFR3, and FGFR4. To date, there are 22 known FGFs, each with the capacity to bind one or more FGFRs. See, e.g., Zhang et al., *J. Biol. Chem.* 281:15, 694-15,700 (2006). Each FGFR binds to several FGFs, and the different FGFRs may differ from each other both in the selection of FGFs to which they bind as well as in the affinity of those interactions.

The FGFRs are transmembrane proteins having an extracellular domain (ECD), a transmembrane domain, and an intracytoplasmic tyrosine kinase domain. Each of the ECDs contains either two or three immunoglobulin (Ig) domains. When there are three Ig domains, they are referred to as D1, D2, and D3 domains. Receptors having two Ig domains typically lack D1. Extracellular FGFR activation by FGF ligand binding to an FGFR initiates a cascade of signaling events inside the cell, beginning with oligomerization of the receptor and activation of receptor tyrosine kinase activity. Structural studies of FGFR-FGF complexes have shown that FGF ligands interact extensively with the D2 domain, the D3 domain, and the linker region connecting the D2 and D3 domains of an FGFR ECD.

In experiments to determine whether an FGFR4 ECD fusion molecule exhibited antitumor activity in a cancer xenograft model, the inventors discovered that an FGFR4 ECD fusion molecule promoted hair growth at the shaved site where the tumor cells were injected. See Example 9 and FIG. 3. In subsequent experiments, both a native FGFR4 ECD fragment fusion molecule ("R4Mut4") and an FGFR4 ECD variant fusion molecule ("ABMut1") that retained FGFR4 ECD ligand binding activity promoted hair growth when administered systemically in mice. See Examples 7, 8, 10, and 11, Tables 2 and 3, and FIG. 4. Experiments in which ABMut1 or agarose beads bound to ABMut1 were subcutaneously injected into the flank of shaved mice showed that local delivery of ABMut1 also promoted hair growth. Further experiments demonstrated that systemic delivery of ABMut1 could also induce anagen in hair follicles, specifically elongation of the dermal papilla into the fatty layer of the dermis. See Example 12 and FIG. 5. Furthermore, hair growth in a shaved mouse model increased with dose of ABMut1. See Example 15 and FIG. 7. In contrast, FGFR1 ECD and FGFR2 ECD fusion molecules did not promote visible hair growth in a shaved mouse model. See Examples 13 and 14 and FIG. 6.

In certain embodiments, a method of promoting hair growth comprising administering an FGFR4 ECD to a subject in an amount sufficient to promote hair growth is provided. In certain embodiments, the FGFR4 ECD is a native FGFR4 ECD. In certain embodiments, the FGFR4 ECD is an FGFR4 ECD variant. In certain embodiments, the FGFR4 ECD is an FGFR4 ECD fragment. In certain embodiments, the FGFR4 ECD is a native FGFR4 ECD fragment. In certain embodiments, the FGFR4 ECD is a variant of an FGFR4 ECD fragment. In certain embodiments, the FGFR4 ECD is an FGFR4 2Ig ECD. In certain embodiments, the FGFR4 ECD is a native FGFR4 2Ig ECD. In certain embodiments, the FGFR4 ECD is an FGFR4 2Ig ECD variant. In certain embodiments, the FGFR4 ECD is an FGFR4 ECD acidic region mutein. In certain embodiments, the FGFR4 ECD is an FGFR4 ECD D1-D2 linker chimera. In certain embodiments, the FGFR4 ECD is an FGFR4 ECD glycosylation mutant. In certain embodiments, the amino acid sequence of the FGFR4 ECD is at least 80% identical to SEQ ID NO: 1, 2, 3, or 4. In certain embodiments, the amino acid sequence of the FGFR4 ECD is at least 85% identical to SEQ ID NO: 1, 2, 3, or 4. In certain embodiments, the amino acid sequence of the FGFR4 ECD is at least 90% identical to SEQ ID NO: 1, 2, 3, or 4. In certain embodiments, the amino acid sequence of the FGFR4 ECD is at least 95% identical to SEQ ID NO: 1, 2, 3, or 4. In certain embodiments, the amino acid sequence of the FGFR4 ECD is at least 99% identical to SEQ ID NO: 1, 2, 3, or 4. In certain embodiments, the amino acid sequence of the FGFR4 ECD has an amino acid sequence of SEQ ID NO: 10. In certain embodiments, the amino acid sequence of the FGFR4 ECD has an amino acid sequence of SEQ ID NO: 29. In certain embodiments, the FGFR4 ECD lacks a signal sequence. In certain embodiments, the FGFR4 ECD comprises a signal sequence. In certain embodiments, the signal sequence is the native signal sequence of FGFR1, FGFR2, FGFR3, or FGFR4. In certain embodiments, the signal sequence is not an FGFR signal sequence. In certain embodiments, the subject is a rodent, simian, human, feline, canine, equine, bovine, porcine, ovine, caprine, mammalian laboratory animal, mammalian farm animal, mammalian sport animal, or mammalian pet. In certain embodiments, the subject is a human. In certain embodiments, the administering is intravenous, subcutaneous, intraperitoneal, topical, or transdermal.

In certain embodiments, a method of growing hair comprising administering an FGFR4 ECD fusion molecule to a subject in an amount sufficient to promote hair growth is provided. In certain embodiments, the FGFR4 ECD fusion molecule comprises an FGFR4 ECD polypeptide and a fusion partner. In certain embodiments, the FGFR4 ECD polypeptide is a native FGFR4 ECD. In certain embodiments, the FGFR4 ECD polypeptide is an FGFR4 ECD variant. In certain embodiments, the FGFR4 ECD polypeptide is an FGFR4 ECD fragment. In certain embodiments, the FGFR4 ECD polypeptide is a variant of an FGFR4 ECD fragment. In certain embodiments, the FGFR4 ECD polypeptide is an FGFR4 2Ig ECD. In certain embodiments, the FGFR4 ECD polypeptide is an FGFR4 ECD acidic region mutein. In certain embodiments, the FGFR4 ECD is an FGFR4 ECD D1-D2 linker chimera. In certain embodiments, the FGFR4 ECD is an FGFR4 ECD glycosylation mutant. In certain embodiments, the fusion partner is selected from an Fc, albumin, and polyethylene glycol. In certain embodiments, the fusion partner is an Fc. In certain embodiments, the FGFR4 ECD fusion molecule has an amino acid sequence of SEQ ID NO: 15. In certain embodiments, the FGFR4 ECD fusion molecule has an amino acid sequence of SEQ ID NO: 52. In certain embodiments, the FGFR4 ECD fusion molecule lacks a singal sequence. In certain embodiments, the FGFR4 ECD fusion molecule comprises a signal sequence. In certain embodiments, the signal sequence is the native signal sequence of FGFR1, FGFR2, FGFR3, or FGFR4. In certain embodiments, the signal sequence is not an FGFR signal sequence. In certain embodiments, the subject is a rodent, simian, human, feline, canine, equine, bovine, porcine, ovine, caprine, mammalian laboratory animal, mammalian farm animal, mammalian sport animal, or mammalian pet. In certain embodiments, the subject is a human. In certain embodiments, the administering is intravenous, subcutaneous, intraperitoneal, topical, transdermal, or intradermal.

BRIEF DESCRIPTION OF THE DRAWINGS

Figure 1:
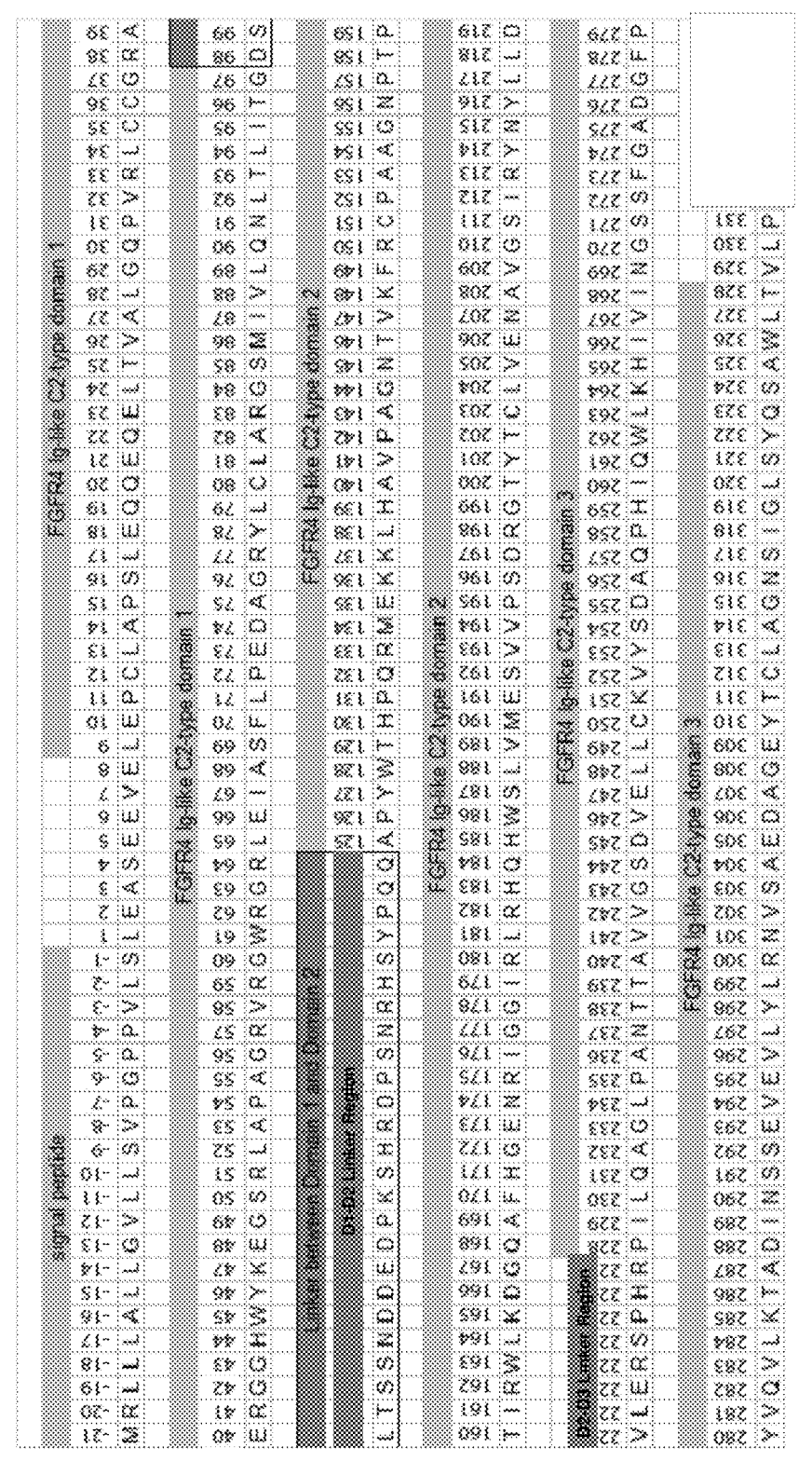

FIG. 1 shows the extracellular domain (ECD) amino acid sequence of FGFR4 with a 17 amino acid carboxy-terminal deletion (SEQ ID NO: 105). The amino acid sequence in FIG. 1 includes the signal peptide, which is cleaved in the mature fusion protein. The numbers refer to the amino acid position, and certain domains within the ECD are illustrated in gray above the amino acid numbers. The amino acid positions within the signal peptide are given negative values because they are cleaved in the mature fusion protein (SEQ ID NO: 10). The first amino acid residue of the mature fusion protein is designated as amino acid position 1. The signal peptide and domains D1, D2, and D3 are noted in gray shading. The linker between the first and second Ig domains (referred to herein interchangeably as the "FGFR4 ECD D1-D2 linker" and "FGFR4 ECD D1-D2 linker region") and the linker between the second and third Ig domains (referred to herein interchangeably as the "FGFR4 ECD D2-D3 linker," "FGFR4 ECD D2-D3 linker," and "FGFR4 ECD D2-D3 linker region" are illustrated in a darker gray.

Figure 2:
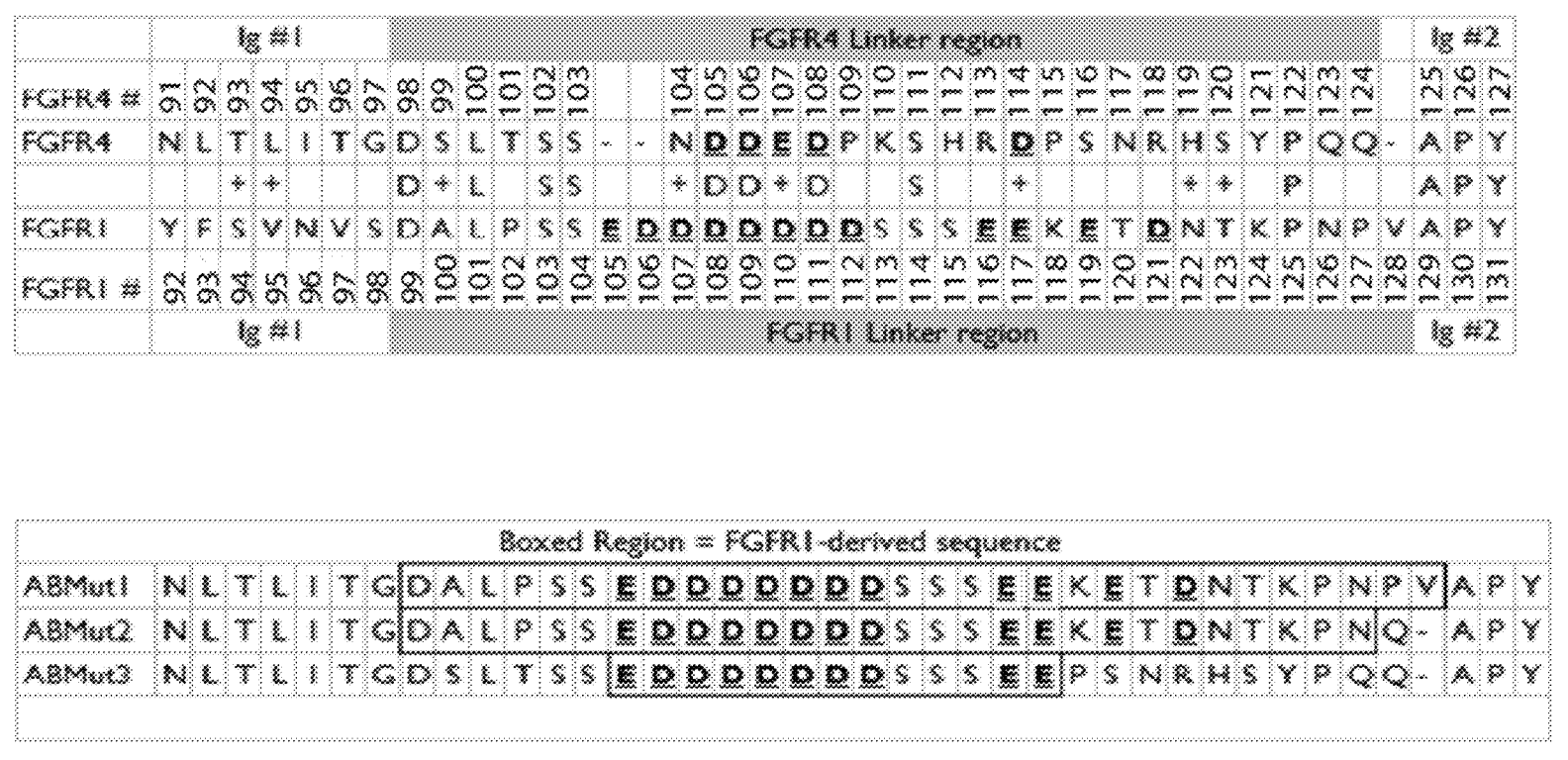

FIG. 2 shows a sequence alignment of the D1-D2 linker regions from FGFR4 and FGFR1 and the boundaries and sequence of the swapped regions in three FGFR4 ECD variants, called FGFR4 ECD(ABMut1: delta17)-Fc ("ABMut1") (SEQ ID NO: 52), FGFR4ECD(ABMut2: delta17)-Fc ("ABMut2") (SEQ ID NO: 53), and FGFR4ECD(ABMut3: delta17)-Fc ("ABMut3") (SEQ ID NO: 91). Acidic residues within the D1-D2 linker are indicated with underlining and bold font.

DETAILED DESCRIPTION OF CERTAIN EMBODIMENTS

Figure 3:
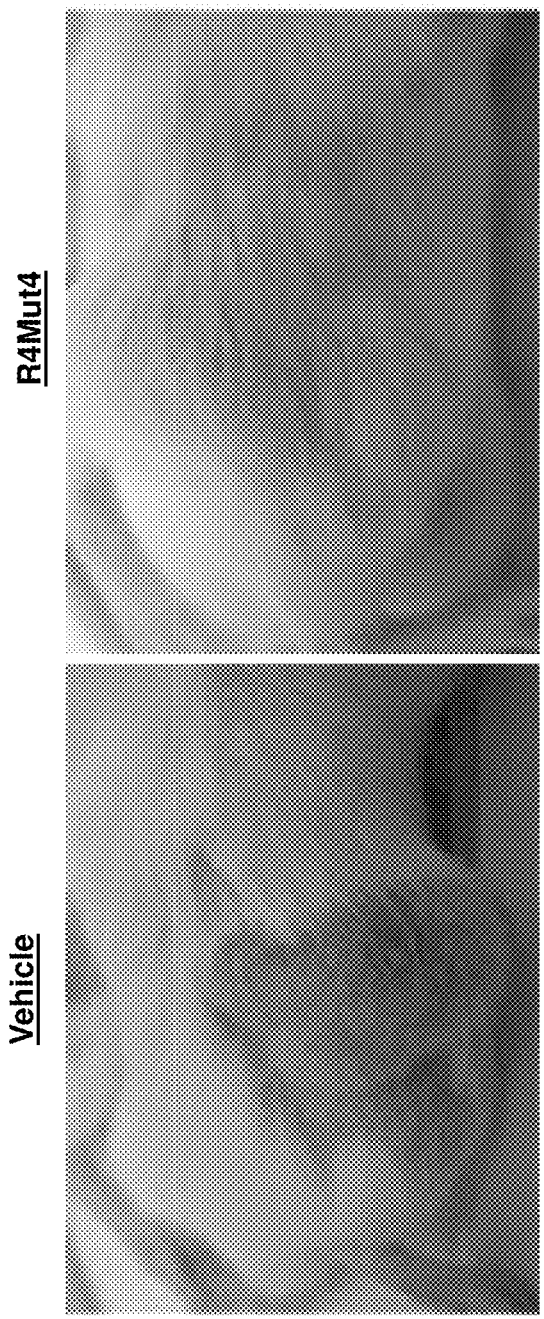
FIG. 3 shows that systemic delivery of R4Mut4 (SEQ ID NO: 15) promotes hair growth in a cancer xenograft model at the shaved site where the tumor cells were injected. R4Mut4 is an FGFR4 ECD with a 17 amino acid C-terminal deletion, which is fused at the carboxy-terminus to an Fc domain. Shown are the shaved sites of tumor cell injection in a vehicle-treated mouse and in an R4Mut4-treated mouse at 15 days post-dose.

The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Certain techniques used in connection with recombinant DNA, oligonucleotide synthesis, tissue culture and transformation (e.g., electroporation, lipofection), enzymatic reactions, and purification techniques are known in the art. Many such techniques and procedures are described, e.g., in Sambrook et al. *Molecular Cloning: A Laboratory Manual* (2d ed., Cold Spring Harbor Laboratory Press, Cold Spring Harbor, N.Y. (1989)), among other places. In addition, certain techniques for chemical syntheses, chemical analyses, pharmaceutical preparation, formulation, delivery, and treatment of patients are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "nucleic acid molecule" and "polynucleotide" may be used interchangeably, and refer to a polymer of nucleotides. Such polymers of nucleotides may contain natural and/or non-natural nucleotides, and include, but are not limited to, DNA, RNA, and PNA.

The terms "polypeptide" and "protein" are used interchangeably, and refer to a polymer of amino acid residues. Such polymers of amino acid residues may contain natural and/or non-natural amino acid residues, and include, but are not limited to, peptides, oligopeptides, dimers, trimers, and multimers of amino acid residues. The terms "polypeptide" and "protein" include natural and non-natural amino acid sequences, and both full-length proteins and fragments thereof. Those terms also include post-translationally modified polypeptides and proteins, including, for example, glycosylated, sialylated, acetylated, and/or phosphorylated polypeptides and proteins.

The terms "acidic amino acid," "acidic amino acid residue," and "acidic residue" are used interchangeably herein and refer to an amino acid residue that is negatively charged at physiological pH. Acidic amino acids include, but are not limited to, aspartic acid (Asp, D) and glutamic acid (Glu, E).

The terms "non-acidic amino acid," "non-acidic amino acid residue," and "non-acidic residue" are used interchangeably and refer to an amino acid residue that is not negatively charged at physiological pH.

The terms "conservative amino acid substitutions" and "conservative substitutions" are used interchangeably herein to refer to intended amino acid swaps within a group of amino acids wherein an amino acid is exchanged with a different amino acid of similar size, structure, charge, and/or polarity. Examples include exchange of one of the aliphatic or hydrophobic amino acids Ala, Val, Leu, and Ile for one of the other amino acids in that group of four; exchange between the hydroxyl-containing residues Ser and Thr; exchange between the acidic residues Asp and Glu; exchange between the amide residues Asn and Gln, exchange between the basic residues Lys, Arg, and His; exchange between the aromatic residues Phe, Tyr, and Trp; and exchange between the small-sized amino acids Ala, Ser, Thr, Met, and Gly.

The terms "FGFR extracellular domain" and "FGFR ECD" in the context of this invention refer to the portion of an FGFR that is normally found in the extracellular space. An FGFR ECD may include the amino-terminal residues that precede the D1 domain, the D1 domain, the D1-D2 linker region, the D2 domain, the D2-D3 linker region, the D3 domain, and the carboxy-terminal residues that follow the D3 domain.

The terms "FGFR4 extracellular domain" and "FGFR4 ECD" as used herein refer to a genus consisting of the following sub-genuses: native FGFR4 ECDs, FGFR4 ECD variants, FGFR4 ECD fragments, native FGFR4 ECD fragments, variants of FGFR4 ECD fragments, FGFR4 2Ig ECDs, native FGFR4 2Ig ECDs, FGFR4 2Ig ECD variants, FGFR4 ECD acidic region muteins, FGFR4 ECD D1-D2 linker chimeras, FGFR4 ECD glycosylation mutants, and FGFR4 ECD fusion molecules, as well as non-human FGFR4 ECDs. The FGFR4 ECDs as defined herein bind FGF2 and/or FGF19 as tested herein. (See Examples 7 and 8.)

As used herein, the terms "native FGFR4 ECD" and "wild-type FGFR4 ECD" are used interchangeably to refer to an FGFR4 ECD consisting of an amino acid sequence selected from SEQ ID NOs: 1, 2, 3, and 4.

As used herein, the term "FGFR4 ECD variants" refers to FGFR4 ECDs containing amino acid additions, deletions, and substitutions in comparison to the native FGFR ECDs of SEQ ID NOs: 1, 2, 3, or 4. Amino acid additions and deletions may be made at the amino-terminus, at the carboxy-terminus, and/or within SEQ ID NOs: 1, 2, 3, or 4.

As used herein, the term "native FGFR4 ECD fragment" refers to an FGFR4 ECD having an amino acid sequence selected from SEQ ID NOs: 1, 2, 3, and 4, but modified in that amino acid residues have been deleted from the amino-terminus and/or from the carboxy-terminus of the polypeptide. Non-limiting examples of native FGFR4 ECD fragments include "native FGFR4 2Ig ECDs" defined below, as well as the amino acid sequences shown in SEQ ID NOs: 7 to 11, and 44 to 49.

As used herein, the terms "FGFR4 ECD fragment variant" and "variant of FGFR4 ECD fragment" are used interchangeably to refer to FGFR4 ECDs containing, not only amino acid deletions from the amino- and/or carboxy-terminus of SEQ ID NOs: 1, 2, 3, or 4, but also amino acid additions, deletions, and substitutions within the retained portion of SEQ ID NOs: 1, 2, 3, or 4.

Collectively, "native FGFR4 ECD fragments" and "FGFR4 ECD fragment variants" form the genus of "FGFR4 ECD fragments."

The term "FGFR4 ECD D1 domain" refers to the first Ig domain of a native FGFR4 ECD. The native FGFR4 ECD D1 domain consists of the sequence of SEQ ID NO: 98, which is amino acids 9 to 97, inclusive, of SEQ ID NO: 1. (See also FIG. 1.)

The term "FGFR4 ECD D2 domain" refers to the second Ig domain of a native FGFR4 ECD. The native FGFR4 ECD D2 domain consists of the sequence of SEQ ID NO: 99, which is amino acids 125 to 219, inclusive, of SEQ ID NO: 1; or consists of the sequence of SEQ ID NO: 100, which is amino acids 125 to 219, inclusive, of SEQ ID NO: 4. (See also FIG. 1.)

The term "FGFR4 ECD D3 domain" refers to the third Ig domain of a native FGFR4 ECD. The native FGFR4 ECD D3 domain consists of the sequence of SEQ ID NO: 101, which is amino acids 228 to 328, inclusive, of SEQ ID NO: 1; or consists of the sequence of SEQ ID NO: 102, which is amino acids 228 to 328, inclusive, of SEQ ID NO: 3. (See also FIG. 1.)

The terms "FGFR4 ECD D1-D2 linker" and "FGFR4 ECD D1-D2 linker region" are used interchangeably to refer to the linker between the first and second Ig domains (the D1 and D2 domains, respectively) of the FGFR4 ECD. The native FGFR4 ECD D1-D2 linker consists of the sequence DSLTSSNDDEDPKSHRDPSNRHSYPQQ (SEQ ID NO: 17), which is amino acids 98 to 124, inclusive, of SEQ ID NO: 1; or consists of the sequence DSLTSSNDDEDPKSHRDL-SNRHSYPQQ (SEQ ID NO: 18), which is amino acids 98 to 124, inclusive, of SEQ ID NO: 2. (See also FIG. 1.)

The terms "FGFR4 ECD D2-D3 linker" and "FGFR4 ECD D2-D3 linker region" are used interchangeably to refer to the linker between the second and third Ig domains (the D2 and D3 domains, respectively) of the FGFR4 ECD. The native FGFR4 ECD D2-D3 linker consists of the sequence VLER-SPHR (SEQ ID NO: 103), which is amino acids 220 to 227, inclusive, of SEQ ID NO: 1. (See also FIG. 1.)

In certain embodiments, an FGFR4 ECD variant corresponds to an "FGFR4 2Ig extracellular domain" or "FGFR4 2Ig ECD." An FGFR4 2Ig ECD as defined herein is an FGFR4 ECD variant wherein at least a portion of the D1 domain is deleted, but that retains the D2 domain, D3 domain, and D2-D3 linker region. Such polypeptides, for example, may also retain all or a portion of the FGFR4 ECD D1-D2 linker region or may lack the FGFR4 ECD D1-D2 linker region. Such polypeptides, for example, may optionally retain all or a portion of the 8 amino acids prior to the D1 domain. An exemplary FGFR4 2Ig ECD that retains the entire FGFR4 ECD D1-D2 linker region consists of the sequence of SEQ ID NO: 58. An exemplary FGFR4 2Ig ECD that lacks the D1-D2 linker region consists of the amino acid sequence of SEQ ID NO: 59. FGFR4 2Ig ECDs include native FGFR4 2Ig ECDs and FGFR4 2Ig ECD variants.

As used herein, the term "native FGFR4 2Ig ECD" refers to an FGFR4 2Ig ECD wherein the polypeptide sequence that is retained after the deletion is a native FGFR4 ECD sequence consisting of the remaining portion of SEQ ID NOs: 1, 2, 3, or 4. An exemplary native FGFR4 2Ig ECD that retains the entire FGFR4 ECD D1-D2 linker region has the amino acid sequence of SEQ ID NO: 58. An exemplary native FGFR4 2Ig ECD that lacks the D1-D2 linker region consists of the amino acid sequence of SEQ ID NO: 59. As used herein, the term "FGFR4 2Ig ECD variants" refers to variants of the FGFR4 2Ig ECDs wherein the remaining FGFR4 ECD sequence, in comparison to SEQ ID NOs: 1, 2, 3, and 4, contains amino acid additions, deletions, and/or substitutions.

As used herein, an "FGFR4 ECD acidic region mutein" is an FGFR4 ECD variant having a greater number of acidic residues in the D1-D2 linker region than the native FGFR4 ECD D1-D2 linker region. Non-limiting exemplary FGFR4 ECD acidic region muteins include SEQ ID NOs: 29 to 33, 64 to 76, 90, and 92.

An "FGFR4 ECD D1-D2 linker chimera" refers to an FGFR4 ECD acidic region mutein wherein the D1-D2 linker region has been replaced with the D1-D2 linker region from FGFR1, FGFR2, or FGFR3. In certain exemplary D1-D2 linker chimeras, the D1-D2 linker of the native FGFR4 ECD (SEQ ID NOs: 17 or 18, described above), is exchanged for a D1-D2 linker of FGFR1: DALPSSEDDDDDDSS-SEEKETDNTKPNPV (SEQ ID NO: 23), which is amino acids 99 to 128, inclusive, of SEQ ID NO: 22; or DALPSSEDDDDDDDSSSEEKETDNTKPNRMPV (SEQ ID NO: 27), which is amino acids 99 to 130, inclusive, of SEQ ID NO: 26. Certain exemplary FGFR4 ECD D1-D2 linker chimeras include, but are not limited to, FGFR4 ECD D1-D2 linker chimeras consisting of the amino acid sequences of SEQ ID NOs: 29 and 30.

FGFR4 ECD variants may include amino acid substitutions within the FGFR4 ECD sequence that inhibit N-glycosylation, referred to interchangeably herein as "FGFR4 ECD glycosylation mutants" and "FGFR4 ECD N-glycan mutants." In certain embodiments, one or more amino acids are mutated to prevent glycosylation at that site in the polypeptide. Non-limiting exemplary native FGFR4 ECD amino acids that may be glycosylated include N91, N156, N237, N269, N290, and N301 in SEQ ID NOs: 1, 2, 3, and 4. Accordingly, one or more of those amino acids may be substituted. Non-limiting exemplary amino acid substitutions include N91A, N156A, N237A, N269A, N290A, and N301A in SEQ ID NOs: 1, 2, 3, and 4. Non-limiting exemplary FGFR4 ECD glycosylation mutants include SEQ ID NOs: 75, 76, and 92.

The terms "FGFR4 ECD fusion molecule" and "FGFR ECD fusion" are used interchangeably herein to refer to an FGFR4 ECD comprising an FGFR4 ECD polypeptide and a fusion partner. FGFR4 ECD fusions may be constructed based upon any of the FGFR4 ECD genera defined above or any of the FGFR4 ECD species described elsewhere herein. The fusion partner may be linked to either the amino-terminus or the carboxy-terminus of the polypeptide. In certain embodiments, the polypeptide and the fusion partner are covalently linked. If the fusion partner is also a polypeptide ("the fusion partner polypeptide"), the polypeptide and the fusion partner polypeptide may be part of a continuous amino acid sequence. In such cases, the polypeptide and the fusion partner polypeptide may be translated as a single polypeptide from a coding sequence that encodes both the polypeptide and the fusion partner polypeptide. In certain embodiments, the polypeptide and the fusion partner are covalently linked through other means, such as, for example, a chemical linkage other than a peptide bond. Many methods of covalently linking polypeptides to other molecules (for example, fusion partners) are known in the art. One skilled in the art can select a suitable method of covalent linkage based on the particular polypeptide and fusion partner to be covalently linked.

In certain embodiments, the polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

Certain exemplary fusion partners include, but are not limited to, an immunoglobulin Fc domain, albumin, and polyethylene glycol. The amino acid sequences of certain exemplary Fc domains are shown in SEQ ID NOs: 40 to 42, 94, and 95. Exemplary FGFR4 ECD Fc fusions include those shown in Table 1 below.

In certain embodiments, the FGFR4 ECD amino acid sequence is derived from that of a non-human mammal. Such FGFR4 ECDs are termed "non-human FGFR4 ECDs." In such embodiments, the FGFR4 ECD sequence may be derived from mammals including, but not limited to, rodents, simians, felines, canines, equines, bovines, porcines, ovines, caprines, mammalian laboratory animals, mammalian farm animals, mammalian sport animals, and mammalian pets. Known non-human FGFR4 ECD sequences include those with GenBank Accession Nos. NP_032037, NP_001103374, XP_546211, XP_602166, XP_001087243, and XP_518127. Such FGFR4 ECD sequences can be modified in the same way as the human FGFR4 ECD sequences described above. In other words, non-human FGFR4 ECDs include the corresponding native FGFR4 ECDs, FGFR4 ECD variants, FGFR4 ECD fragments, native FGFR4 ECD fragments, variants of FGFR4 ECD fragments, FGFR4 2Ig ECDs, native FGFR4 2Ig ECDs, FGFR4 2Ig ECD variants, FGFR4 ECD acidic region muteins, FGFR4 ECD D1-D2 linker chimeras, FGFR4 ECD glycosylation mutants, and FGFR4 ECD fusion molecules.

The terms "signal peptide" and "signal sequence" are used interchangeably herein to refer to a sequence of amino acid residues that facilitates secretion of a polypeptide from a mammalian cell. A signal peptide is typically cleaved upon export of the polypeptide from the mammalian cell. Certain exemplary signal peptides include, but are not limited to, the native signal peptides of FGFR1, FGFR2, FGFR3, and FGFR4, such as, for example, the amino acid sequences of SEQ ID NOs: 34 to 37, and 43. Certain exemplary signal peptides also include signal peptides from heterologous proteins. A "signal sequence" refers to a polynucleotide sequence that encodes a signal peptide.

A "vector" refers to a polynucleotide that is used to express a polypeptide of interest in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, e.g., β-galactosidase). One skilled in the art can select suitable vector elements for the particular host cell and application at hand.

A "host cell" refers to a cell that can be or has been a recipient of a vector or isolated polynucleotide. Host cells may be prokaryotic cells or eukaryotic cells. Exemplary eukaryotic cells include mammalian cells, such as primate or non-primate animal cells; fungal cells; plant cells; and insect cells. Certain exemplary mammalian cells include, but are not limited to, 293 and CHO cells.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "subject" is used herein to refer to mammals, including, but not limited to, rodents, simians, humans, felines, canines, equines, bovines, porcines, ovines, caprines, mammalian laboratory animals, mammalian farm animals, mammalian sport animals, and mammalian pets.

"Treatment," as used herein, covers any administration or application of a composition for a disease or condition and includes preventing its occurrence, inhibiting or slowing its progress, arresting its development, ameliorating, or relieving it "Administration," as used herein, includes both self-administration by the subject as well as administration by another individual, such as a physician, nurse, or veterinarian.

A "pharmaceutically acceptable carrier" refers to a non-toxic solid, semisolid, or liquid filler, diluent, encapsulating material, formulation auxiliary, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the composition is to be administered orally, the carrier may be a gel capsule. If the composition is to be administered subcutaneously, the carrier ideally is not irritable to the skin and does not cause injection site reaction.

FGFR4 ECDs

As defined above, an FGFR4 ECD is a genus consisting of the following sub-genuses: native FGFR4 ECDs, FGFR4 ECD variants, FGFR4 ECD fragments, native FGFR4 ECD fragments, variants of FGFR4 ECD fragments, FGFR4 2Ig ECDs, native FGFR4 2Ig ECDs, FGFR4 2Ig ECD variants, FGFR4 ECD acidic region muteins, FGFR4 ECD D1-D2 linker chimeras, FGFR4 ECD glycosylation mutants, and FGFR4 ECD fusion molecules, as well as non-human FGFR4 ECDs. In certain embodiments, an FGFR4 ECD is isolated. The FGFR4 ECDs as defined herein bind FGF2 and/or FGF19 as tested herein.

Descriptions of the methods used herein to test FGF2 and FGF19 binding by FGFR4 ECDs are provided in Examples 7 and 8. Two different types of assays were used to measure FGF2 and FGF19 binding, a Biacore® X surface plasmon resonance (SPR) technology-based assay and a competition ELISA assay. In certain embodiments, an FGFR4 ECD binds to FGF2 with an equilibrium dissociation constant ($K_D$) value of no more than 1 µM, or no more than 100 nM, or no more than 10 nM, or no more than 6 nM in a Biacore® X SPR ligand binding assay. (See Example 7.) In certain embodiments, an FGFR4 ECD binds to FGF19 with a $K_D$ value of no more than 1 µM, or no more than 100 nM, or no more than 50 nM in a Biacore® X SPR ligand binding assay. (Id.)

One skilled in the art can create FGFR4 ECDs that are capable of binding to FGF2 and/or FGF19 based on structural data for FGFRs and FGFR-FGF binding as well as knowledge from prior mutational experiments in the art. For example, previous structural studies have shown that FGFR-FGF binding is largely determined by the interaction between the FGF ligand and the D2 domain, D3 domain, and D2-D3 linker region of the FGFR ECD. See e.g., Plotnikov et al., Cell 98:641-650 (1999); and Olsen et al., Proc. Natl. Acad. Sci. 101(4):935-940 (2004). Thus, the D1 domain and the D1-D2 linker region of an FGFR ECD may be modified such that FGF binding is maintained. Previous studies have shown that FGFR4 ECD ligand binding specificity can be maintained when at least a portion of the D1 domain is deleted, when at least a portion of the D1 domain and the D1-D2 linker region are deleted, when the D1-D2 linker region is replaced with the FGFR1 ECD D1-D2 linker region, and when residues within the D1-D2 linker region are mutated. See e.g., U.S. patent application Ser. No. 12/535,479, now U.S. Pat. No. 8,338,569. Furthermore, previous studies have shown that FGFR4 ECDs can maintain their ligand binding profile when a binding partner is attached to their carboxy-terminus, such as to create a fusion molecule. Id. Accordingly, embodiments of the present invention may include one or a combination of such mutational strategies. Exemplary polypeptides that may be used in the present invention include each of the following:

Native FGFR4 ECDs

As described above, native FGFR4 ECDs are FGFR4 ECDs consisting of an amino acid sequence selected from SEQ ID NOs: 1, 2, 3, and 4. In some embodiments, such a native FGFR4 ECD may be used.

FGFR4 ECD Variants

As set forth above, FGFR4 ECD variants are FGFR4 ECDs containing amino acid additions, deletions, and substitutions in comparison to the native FGFR ECDs of SEQ ID NOs: 1, 2, 3, or 4. Amino acid additions and deletions may be made at the amino-terminus, at the carboxy-terminus, and/or within SEQ ID NOs: 1, 2, 3, or 4. For example, in some embodiments, the FGFR4 ECD may comprise SEQ ID NO: 1, 2, 3, or 4, so as to include optional additional amino acids on one or both termini. In other embodiments, the FGFR4 ECD may include additions, deletions, or substitutions within SEQ ID NO: 1, 2, 3, or 4. In yet other embodiments, the FGFR4 ECD may include a combination of additions or deletions from one or both ends of SEQ ID NOs: 1, 2, 3, or 4 and substitutions, additions, or deletions within the native sequence of SEQ ID NOs: 1, 2, 3, or 4.

In certain embodiments, the amino acid sequence of the FGFR4 ECD is at least 80% identical to SEQ ID NOs: 1, 2, 3, or 4. In certain embodiments, the amino acid sequence of an FGFR4 ECD is at least 85% identical to SEQ ID NO: 1, 2, 3, or 4. In certain embodiments, the amino acid sequence of an FGFR4 ECD is at least 90% identical to SEQ ID NOs: 1, 2, 3, or 4. In certain embodiments, the amino acid sequence of an FGFR4 ECD is at least 95% identical to SEQ ID NOs: 1, 2, 3, or 4. And in certain embodiments, the amino acid sequence of an FGFR4 ECD is at least 99% identical to SEQ ID NOs: 1, 2, 3, or 4.

Native FGFR4 ECD Fragments

As defined above, native FGFR4 ECD fragments are FGFR4 ECDs having an amino acid sequence selected from SEQ ID NOs: 1, 2, 3, and 4, but modified in that amino acid residues have been deleted from the amino-terminus and/or from the carboxy-terminus of the polypeptide. Non-limiting examples of native FGFR4 ECD fragments include "native FGFR4 2Ig ECDs" defined below, as well as the amino acid sequences shown in SEQ ID NOs: 7 to 11, and 44 to 49.

Variants of FGFR4 ECD Fragments

As described above, variants of FGFR4 ECD fragments are FGFR4 ECDs containing, not only amino acid deletions from the amino- and/or carboxy-terminus of SEQ ID NOs: 1, 2, 3, or 4, but also amino acid additions, deletions, and substitutions within the retained portion of SEQ ID NOs: 1, 2, 3, or 4.

Collectively, "native FGFR4 ECD fragments" and "variants of FGFR4 ECD fragments" form the genus of "FGFR4 ECD fragments."

FGFR4 2Ig ECDs

As defined above, FGFR4 2Ig ECDs are FGFR4 ECD variants wherein at least a portion of the D1 domain is deleted, but that retains the D2 domain, D3 domain, and D2-D3 linker region. Such polypeptides, for example, may also retain all or a portion of the FGFR4 ECD D1-D2 linker region or may lack the FGFR4 ECD D1-D2 linker region. Such polypeptides, for example, may optionally retain all or a portion of the 8 amino acids prior to the D1 domain. An exemplary FGFR4 2Ig ECD that retains the entire FGFR4 ECD D1-D2 linker region consists of the sequence of SEQ ID NO: 58. An exemplary FGFR4 2Ig ECD that lacks the D1-D2 linker region consists of the amino acid sequence of SEQ ID NO: 59. FGFR4 2Ig ECDs include native FGFR4 2Ig ECDs and FGFR4 2Ig ECD variants.

Native FGFR4 2Ig ECDs

As set forth above, native FGFR4 2Ig ECDs are FGFR4 2Ig ECDs wherein the polypeptide sequence that is retained after the deletion is a native FGFR4 ECD sequence consisting of the remaining portion of SEQ ID NOs: 1, 2, 3, or 4. An exemplary native FGFR4 2Ig ECD that retains the entire FGFR4 ECD D1-D2 linker region has the amino acid sequence of SEQ ID NO: 58. An exemplary native FGFR4 2Ig ECD that lacks the D1-D2 linker region consists of the amino acid sequence of SEQ ID NO: 59.

FGFR4 2Ig ECD Variants

As defined above, FGFR4 2Ig ECD variants are variants of the FGFR4 2Ig ECDs wherein the remaining FGFR4 ECD sequence, in comparison to SEQ ID NOs: 1, 2, 3, and 4, contains amino acid additions, deletions, and/or substitutions.

FGFR4 ECD Acidic Region Muteins

As described above, FGFR4 ECD acidic region muteins are FGFR4 ECD variants having a greater number of acidic residues in the D1-D2 linker region than the native FGFR4 ECD D1-D2 linker region. Non-limiting exemplary FGFR4 ECD acidic region muteins include SEQ ID NOs: 29 to 33, 64 to 76, 90, and 92.

FGFR4 ECD D1-D2 Linker Chimeras

As defined above, FGFR4 ECD D1-D2 linker chimeras are FGFR4 ECD acidic region muteins wherein the D1-D2 linker region has been replaced with the D1-D2 linker region from FGFR1, FGFR2, or FGFR3. In certain exemplary D1-D2 linker chimeras, the D1-D2 linker of the native FGFR4 ECD (SEQ ID NOs: 17 or 18, described above), is exchanged for a D1-D2 linker of FGFR1: DALPSSEDDDDDDDSS-SEEKETDNTKPNPV (SEQ ID NO: 23), which is amino acids 99 to 128, inclusive, of SEQ ID NO: 22; or DALPSSEDDDDDDDSSSEEKETDNTKPNRMPV (SEQ ID NO: 27), which is amino acids 99 to 130, inclusive, of SEQ ID NO: 26. Certain exemplary FGFR4 ECD D1-D2 linker chimeras include, but are not limited to, FGFR4 ECD D1-D2 linker chimeras consisting of the amino acid sequences of SEQ ID NOs: 29 and 30.

FGFR4 ECD Glycosylation Mutants

As described above, FGFR4 ECD glycosylation mutations are FGFR4 ECD variants that include amino acid substitutions within the FGFR4 ECD sequence that inhibit N-glycosylation. In certain embodiments, one or more amino acids are mutated to prevent glycosylation at that site in the polypeptide. Non-limiting exemplary native FGFR4 ECD amino acids that may be glycosylated include N91, N156, N237, N269, N290, and N301 in SEQ ID NOs: 1, 2, 3, or 4. Accordingly, one or more of those amino acids may be substituted. Non-limiting exemplary amino acid substitutions include N91A, N156A, N237A, N269A, N290A, and N301A in SEQ ID NOs: 1, 2, 3, or 4. Non-limiting exemplary FGFR4 ECD glycosylation mutants include SEQ ID NOs: 75, 76, and 92.

Signal Peptides

Typically, the signal peptide is cleaved from the mature FGFR4 ECD polypeptide. Thus, in many embodiments, the FGFR4 ECD lacks a signal peptide. Nonetheless, in certain embodiments, an FGFR4 ECD includes at least one signal peptide, which may be selected from a native FGFR4 signal peptide and/or a heterologous signal peptide. In some embodiments, the FGFR4 ECD comprises a signal sequence at its amino terminus. Any one of the above genuses of polypeptides defined above or the polypeptide species described herein may further include a signal peptide. Exemplary signal peptides include, but are not limited to, the signal peptides of FGFR1, FGFR2, FGFR3, and FGFR4, such as, for example, the amino acid sequences of SEQ ID NOs: 34 to 37, and 43. In other embodiments, the signal peptide may be a signal peptides from a heterologous protein.

FGFR4 ECD Fusion Molecules and their Construction

In some embodiments, the FGFR4 ECD is a fusion molecule. Accordingly, any one of the genuses of polypeptides defined above or the polypeptide species described herein may further include a fusion partner. FGFR4 ECD fusion molecules comprising an FGFR4 ECD polypeptide and a fusion partner may be used in the methods herein.

Certain exemplary FGFR4 ECD fusion molecules are provided in Tables 1 and 7. For example, R4Mut4 (SEQ ID NO: 15) is a native FGFR4 ECD fragment (with a 17 amino acid C-terminal deletion) fused to an Fc. ABMut1 (SEQ ID NO: 52) is an FGFR4 ECD D1-D2 linker chimera fused to an Fc. ABMut2 (SEQ ID NO: 53) and ABMut3 (SEQ ID NO: 91) are both acidic region mutein-Fc fusions. Additional non-limiting exemplary FGFR4 ECD acidic region mutein-Fc fusions include SEQ ID NOs: 77 to 89, and 93. An exemplary FGFR4 2Ig ECD-Fc fusion that retains the entire FGFR4 ECD D1-D2 linker region consists of the amino acid sequence of SEQ ID NO: 55. An exemplary FGFR4 2Ig ECD-Fc fusion that lacks the FGFR4 ECD D1-D2 linker region consists of the amino acid sequence of SEQ ID NO: 56. Non-limiting exemplary FGFR4 ECD glycosylation mutant-Fc fusions include SEQ ID NOs: 88, 89, and 93.

Fusion Partners and Conjugates

In certain embodiments, a fusion partner is selected that imparts favorable pharmacokinetics and/or pharmacodynamics on the FGFR4 ECD fusion molecule.

Many different types of fusion partners are known in the art. One skilled in the art can select a suitable fusion partner according to the intended use. Non-limiting exemplary fusion partners include polymers, polypeptides, lipophilic moieties, and succinyl groups. Exemplary polypeptide fusion partners include serum albumin and an antibody Fc domain. Exemplary polymer fusion partners include, but are not limited to, polyethylene glycol, including polyethylene glycols having branched and/or linear chains.

Oligomerization Domain Fusion Partners

In various embodiments, oligomerization offers certain functional advantages to a fusion protein, including, but not limited to, multivalency, increased binding strength, and the combined function of different domains. Accordingly, in certain embodiments, a fusion partner comprises an oligomerization domain, for example, a dimerization domain. Exemplary oligomerization domains include, but are not limited to, coiled-coil domains, including alpha-helical coiled-coil domains; collagen domains; collagen-like domains, and certain immunoglobulin domains. Certain exemplary coiled-coil polypeptide fusion partners include the tetranectin coiled-coil domain; the coiled-coil domain of cartilage oligomeric matrix protein; angiopoietin coiled-coil domains; and leucine zipper domains. Certain exemplary collagen or collagen-like oligomerization domains include, but are not limited to, those found in collagens, mannose binding lectin, lung surfactant proteins A and D, adiponectin, ficolin, conglutinin, macrophage scavenger receptor, and emilin.

Antibody Fc Immunoglobulin Domain Fusion Partners

Many Fc domains that could be used as fusion partners are known in the art. One skilled in the art can select an appropriate Fc domain fusion partner according to the intended use. In certain embodiments, a fusion partner is an Fc immunoglobulin domain. An Fc fusion partner may be a wild-type Fc found in a naturally occurring antibody, a variant thereof, or a fragment thereof. Non-limiting exemplary Fc fusion partners include Fcs comprising a hinge and the CH2 and CH3 constant domains of a human IgG, for example, human IgG1, IgG2, IgG3, or IgG4. Certain additional Fc fusion partners include, but are not limited to, human IgA and IgM. In certain embodiments, an Fc fusion partner comprises a C237S mutation. In certain embodiments, an Fc fusion partner comprises a hinge, CH2, and CH3 domains of human IgG2 with a P331S mutation, as described in U.S. Pat. No. 6,900,292. Certain exemplary Fc domain fusion partners are shown in SEQ ID NOs: 40 to 42, 94, and 95.

Certain exemplary FGFR4 ECD fusion molecules comprise, but are not limited to, polypeptides having the amino acid sequences of SEQ ID NOs: 6, and 12 to 16. Certain exemplary FGFR4 ECD fusion molecules comprising an FGFR4 ECD acidic region mutein include, but are not limited to, polypeptides having the amino acid sequences of SEQ ID NOs: 52 to 54, 77 to 89, 91, and 93. In certain embodiments, an FGFR4 ECD fusion molecule comprises the amino acid sequence of SEQ ID NO: 52. In certain embodiments, an FGFR4 ECD fusion molecule consists of the amino acid sequence of SEQ ID NO: 52.

Albumin Fusion Partners and Albumin-Binding Molecule Fusion Partners

In certain embodiments, a fusion partner is an albumin. Certain exemplary albumins include, but are not limited to, human serum album (HSA) and fragments of HSA that are capable of increasing the serum half-life and/or bioavailability of the polypeptide to which they are fused. In certain embodiments, a fusion partner is an albumin-binding molecule, such as, for example, a peptide that binds albumin or a molecule that conjugates with a lipid or other molecule that binds albumin. In certain embodiments, a fusion molecule comprising HSA is prepared as described, e.g., in U.S. Pat. No. 6,686,179.

Polymer Fusion Partners

In certain embodiments, a fusion partner is a polymer, for example, polyethylene glycol (PEG). PEG may comprise branched and/or linear chains. In certain embodiments, a fusion partner comprises a chemically-derivatized polypeptide having at least one PEG moiety attached. Pegylation of a polypeptide may be carried out by any method known in the art. One skilled in the art can select an appropriate method of pegylating a particular polypeptide, taking into consideration the intended use of the polypeptide. Certain exemplary PEG attachment methods include, for example, EP 0 401 384; Malik et al., *Exp. Hematol.*, 20:1028-1035 (1992); Francis, *Focus on Growth Factors*, 3:4-10 (1992); EP 0 154 316; EP 0 401 384; WO 92/16221; and WO 95/34326. As non-limiting examples, pegylation may be performed via an acylation reaction or an alkylation reaction, resulting in attachment of one or more PEG moieties via acyl or alkyl groups. In certain embodiments, PEG moieties are attached to a polypeptide through the α- or ε-amino group of one or more amino acids, although any other points of attachment known in the art are also contemplated.

Pegylation by acylation typically involves reacting an activated ester derivative of a PEG moiety with a polypeptide. A non-limiting exemplary activated PEG ester is PEG esterified to N-hydroxysuccinimide (NHS). As used herein, acylation is contemplated to include, without limitation, the following types of linkages between a polypeptide and PEG: amide, carbamate, and urethane. See, e.g., Chamow, *Bioconjugate Chem.*, 5:133-140 (1994). Pegylation by alkylation typically involves reacting a terminal aldehyde derivative of a PEG moiety with a polypeptide in the presence of a reducing agent. Non-limiting exemplary reactive PEG aldehydes include PEG propionaldehyde, which is water stable, and mono C1-C10 alkoxy or aryloxy derivatives thereof. See, e.g., U.S. Pat. No. 5,252,714.

In certain embodiments, a pegylation reaction results in poly-pegylated polypeptides. In certain embodiments, a pegylation reaction results in mono-, di-, and/or tri-pegylated polypeptides. One skilled in the art can select appropriate pegylation chemistry and reaction conditions to achieve the desired level of pegylation. Further, desired pegylated species may be separated from a mixture containing other pegylated species and/or unreacted starting materials using various purification techniques known in the art, including among others, dialysis, salting-out, ultrafiltration, ion-exchange chromatography, gel filtration chromatography, and electrophoresis.

Exemplary Attachment of Fusion Partners

The fusion partner may be attached, either covalently or non-covalently, to the amino-terminus or the carboxy-terminus of the FGFR4 ECD. The attachment may also occur at a location within the FGFR4 ECD other than the amino-terminus or the carboxy-terminus, for example, through an amino acid side chain (such as, for example, the side chain of cysteine, lysine, histidine, serine, or threonine).

In either covalent or non-covalent attachment embodiments, a linker may be included between the fusion partner and the FGFR4 ECD. Such linkers may be comprised of amino acids and/or chemical moieties. One skilled in the art can select a suitable linker depending on the attachment method used, the intended use of the FGFR4 ECD fusion molecule, and the desired spacing between the FGFR4 ECD and the fusion partner.

Exemplary methods of covalently attaching a fusion partner to an FGFR4 ECD include, but are not limited to, translation of the fusion partner and the FGFR4 ECD as a single amino acid sequence and chemical attachment of the fusion partner to the FGFR4 ECD. When the fusion partner and the FGFR4 ECD are translated as single amino acid sequence, additional amino acids may be included between the fusion partner and the FGFR4 ECD as a linker. In certain embodiments, the linker is glycine-serine ("GS"). In certain embodiments, the linker is selected based on the polynucleotide sequence that encodes it, to facilitate cloning the fusion partner and/or FGFR4 ECD into a single expression construct (for example, a polynucleotide containing a particular restriction site may be placed between the polynucleotide encoding the fusion partner and the polynucleotide encoding the FGFR4 ECD, wherein the polynucleotide containing the restriction site encodes a short amino acid linker sequence).

When the fusion partner and the FGFR4 ECD are covalently coupled by chemical means, linkers of various sizes can typically be included during the coupling reaction. One skilled in the art can select a suitable method of covalently attaching a fusion partner to an FGFR4 ECD depending, for example, on the identity of the fusion partner and the particular use intended for the FGFR4 ECD fusion molecule. One skilled in the art can also select a suitable linker type and length, if one is desired.

Exemplary methods of non-covalently attaching a fusion partner to an FGFR4 ECD include, but are not limited to, attachment through a binding pair. Exemplary binding pairs include, but are not limited to, biotin and avidin or streptavidin, an antibody and its antigen, etc. Again, one skilled in the art can select a suitable method of non-covalently attaching a fusion partner to an FGFR4 ECD depending, for example, on the identity of the fusion partner and the particular use intended for the FGFR4 ECD fusion molecule. The selected non-covalent attachment method should be suitable for the conditions under which the FGFR4 ECD fusion molecule will be used, taking into account, for example, the pH, salt concentrations, and temperature.

Non-Human FGFR4 ECDs

As described above, in certain embodiments, the FGFR4 ECD amino acid sequence is that of a non-human mammal. In such embodiments, the FGFR4 ECD sequence may be derived from mammals including, but not limited to, rodents, simians, felines, canines, equines, bovines, porcines, ovines, caprines, mammalian laboratory animals, mammalian farm animals, mammalian sport animals, and mammalian pets. Known non-human FGFR4 ECD sequences include those with GenBank Accession Nos. NP_032037, NP_001103374, XP_546211, XP_602166, XP_001087243, and XP_518127. As set forth above, such FGFR4 ECD sequences can be modified in the same way as the human FGFR4 ECD sequences described above. In other words, non-human FGFR4 ECDs include the corresponding native FGFR4 ECDs, FGFR4 ECD variants, FGFR4 ECD fragments, native FGFR4 ECD fragments, variants of FGFR4 ECD fragments, FGFR4 2Ig ECDs, native FGFR4 2Ig ECDs, FGFR4 2Ig ECD variants, FGFR4 ECD acidic region muteins, FGFR4 ECD D1-D2 linker chimeras, FGFR4 ECD glycosylation mutants, and FGFR4 ECD fusion molecules.

Nucleic Acid Molecules, Vectors, and Protein Expression Methods

Nucleic acid molecules that encode FGFR4 ECDs can be constructed by one skilled in the art using recombinant DNA techniques conventional in the art.

In certain embodiments, a polynucleotide encoding a polypeptide of the invention comprises a nucleotide sequence that encodes a signal peptide, which, when translated, will be fused to the amino-terminus of the FGFR4 polypeptide of the invention. As discussed above, the signal peptide may be the native signal peptide, the signal peptide of FGFR1, FGFR2, FGFR3, or FGFR4, or may be another heterologous signal peptide. The amino acid sequences for certain exemplary FGFR signal peptides are shown, e.g., in SEQ ID NOs: 34 to 37, and 43. Certain exemplary signal peptides are known in the art, and are described, e.g., in the online Signal Peptide Database maintained by the Department of Biochemistry, National University of Singapore, http://proline.bic.nus.edu.sg/spdb/index.html (see also Choo et al., *BMC Bioinformatics*, 6: 249 (2005)); and in PCT Publication No. WO 2006/081430.

To prepare the polypeptides, the nucleic acid molecule comprising the polynucleotide encoding the FGFR4 ECD may be placed into a vector suitable for expression in a selected host cell. Such vectors include, but are not limited to, DNA vectors, phage vectors, viral vectors, retroviral vectors, etc. One skilled in the art can select a suitable vector depending on the polypeptide to be expressed and the host cell chosen for expression.

In certain embodiments, a vector is selected that is optimized for expression of polypeptides in CHO-S or CHO-S-derived cells. Exemplary such vectors are described, e.g., in Running Deer et al., *Biotechnol. Prog.* 20:880-889 (2004).

In certain embodiments, a vector is chosen for in vivo expression of the polypeptides of the invention in animals, including humans. In certain such embodiments, expression of the polypeptide is under the control of a promoter that functions in a tissue-specific manner. For example, liver-specific promoters are described, e.g., in PCT Publication No. WO 2006/076288.

The polypeptides of the invention can be expressed, in various embodiments, in prokaryotic cells, such as bacterial cells; or eukaryotic cells, such as fungal cells, plant cells, insect cells, and mammalian cells. Such expression may be carried out, for example, according to procedures known in the art. Certain exemplary eukaryotic cells that can be used to express polypeptides include, but are not limited to, Cos cells, including Cos 7 cells; 293 cells, including 293-6E and 293-T cells; CHO cells, including CHO-S and DG44 cells; and NS0 cells. One skilled in the art can select a suitable host cell depending on the polypeptide to be expressed, the desired use of that polypeptide, and the scale of the production (e.g., a small amount for laboratory use, or a larger amount for pharmaceutical use). In certain embodiments, a particular eukaryotic host cell is selected based on its ability to make certain desired post-translational modifications of the polypeptide of the invention. For example, in certain embodiments, CHO cells produce FGFR4 ECDs that have a higher level of glycosylation and/or sialylation than the same polypeptide produced in 293 cells.

Introduction of a nucleic acid into a desired host cell can be accomplished by any method known in the art, including, but not limited to, calcium phosphate transfection, DEAE-dextran mediated transfection, cationic lipid-mediated transfection, electroporation, transduction, infection, etc. Certain exemplary methods are described, e.g., in Sambrook et al., *Molecular Cloning, A Laboratory Manual*, 3rd ed. Cold Spring Harbor Laboratory Press (2001). Nucleic acids may be transiently or stably transfected in the desired host cells, according to methods known in the art.

In certain embodiments, a polypeptide can be produced in vivo in an animal that has been engineered or transfected with a nucleic acid molecule encoding the polypeptide, according to methods known in the art.

Purification of FGFR4 ECD Polypeptides

The polypeptides of the invention can be purified by various methods known in the art. Such methods include, but are not limited to, the use of affinity matrices, ion exchange chromatography, and/or hydrophobic interaction chromatography. Suitable affinity ligands include any ligands of the FGFR4 ECD, antibodies to FGFR4 ECD, or, in the case of an FGFR4 ECD fusion, a ligand of the fusion partner. For example, a Protein A, Protein G, Protein A/G, or an antibody affinity column may be used to bind to an Fc fusion partner to purify a polypeptide of the invention. Hydrophobic interactive chromatography, for example, a butyl or phenyl column, may also suitable for purifying certain polypeptides. Many methods of purifying polypeptides are known in the art. One skilled in the art can select a suitable method depending on the identity of the polypeptide or molecule to be purified and on the scale of the purification (i.e., the quantity of polypeptide or molecule produced).

Methods of Administration

Routes of Administration and Carriers

The polypeptides of the invention can be administered in vivo by various routes known in the art, including, but not limited to, intravenous, subcutaneous, parenteral, intranasal, intramuscular, buccal, intraperitoneal, intradermal, topical, transdermal, and intrathecal, or otherwise by implantation or inhalation. The subject compositions can be formulated into preparations in solid, semi-solid, liquid, or gaseous forms; including, but not limited to, tablets, capsules, powders, granules, ointments, solutions, injections, inhalants, and aerosols. Nucleic acid molecules encoding the polypeptides of the invention can be coated onto gold microparticles and delivered intradermally by a particle bombardment device, or "gene gun," as described in the literature (see, e.g., Tang et al., *Nature* 356:152-154 (1992)). One skilled in the art can select the appropriate formulation and route of administration according to the intended application.

In some embodiments, compositions comprising the polypeptides of the invention are provided in formulation with pharmaceutically acceptable carriers, a wide variety of which are known in the art (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7th ed., Lippencott Williams and Wilkins (2004); Kibbe et al., *Handbook of Pharmaceutical Excipients*, 3rd ed., Pharmaceutical Press (2000)). Various pharmaceutically acceptable carriers, which include vehicles, adjuvants, carriers, and diluents, are available to the public. Moreover, various pharmaceutically acceptable auxiliary substances, such as pH adjusting and buffering agents, tonicity adjusting agents, stabilizers, wetting agents and the like, are also available to the public. Certain non-limiting exemplary carriers include saline, buffered saline, dextrose, water, glycerol, ethanol, and combinations thereof. One skilled in the art can select a suitable carrier according to the intended use.

In various embodiments, compositions comprising polypeptides of the invention can be formulated for injection by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1. One skilled in the art can select a suitable formulation depending on the intended route of administration, using techniques and components known in the art.

Pharmaceutical packs and kits comprising one or more containers, each containing one or more doses of the polypeptides of the invention are also provided. In certain embodiments, a unit dosage is provided wherein the unit dosage contains a predetermined amount of a composition comprising a polypeptide of the invention, with or without one or more additional agents. In certain embodiments, such a unit dosage is supplied in single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that can be reconstituted upon addition of an appropriate liquid, for example, sterile water. In certain embodiments, the composition comprises one or more substances that inhibit protein aggregation, including, but not limited to, sucrose and arginine. In certain embodiments, a composition of the invention comprises heparin and/or a proteoglycan.

The FGFR4 ECD compositions are administered in an amount effective to promote hair growth. The effective amount is typically dependent on the weight of the subject being treated, his or her physical or health condition, the extensiveness of the condition to be treated, and/or the age of the subject being treated. In general, the polypeptides of the invention can be administered subcutaneously in an amount in the range of about 10 ng to about 500 µg. Optionally, the polypeptides of the invention can be administered subcutaneously in an amount in the range of about 10 ng to about 100 µg. Further optionally, the polypeptides of the invention can be administered subcutaneously in an amount in the range of about 100 ng to about 10 µg. In general, the polypeptides of the invention can be administered intravenously in an amount in the range of about 10 µg/kg body weight to about 30 mg/kg body weight per dose. Optionally, the polypeptides of the invention can be administered intravenously in an amount in the range of about 100 µg/kg body weight to about 20 mg/kg body weight per dose. Further optionally, the polypeptides of the invention can be administered intravenously in an amount in the range of about 0.5 mg/kg body weight to about 20 mg/kg body weight per dose The compositions comprising the polypeptides of the invention can be administered as needed to subjects. Determination of the frequency of administration can be made by persons skilled in the art, such as an attending physician or pharmacist or hair growth specialist based on considerations of the condition being treated, age of the subject being treated, severity of the condition being treated, general state of health of the subject being treated and the like. In certain embodiments, an effective dose of the polypeptide of the invention is administered to a subject one or more times. In various embodiments, an effective dose of the polypeptide of the invention is administered to the subject no more than once a year, nor more than twice a year, no more than twice a month, no more than once a week, no more than twice a week, or no more than three times a week. In various embodiments, an effective dose of the polypeptide of the invention is administered to the subject for no more than a week, for no more than a month, for no more than three months, for no more than six months, or for no more than a year.

Combination Therapy

Polypeptides of the invention may be administered alone or with other modes of treatment. They may be provided before, substantially contemporaneous with, or after other modes of treatment. Certain exemplary combination therapies could include a combination of an FGFR4 ECD with minoxidil, finasteride, dutasteride, other 5-alpha reductase inhibitors, and/or hair transplant surgery.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Certain FGFR4 ECD-Fc Fusion Molecules

The cloning of the parental FGFR4 ECD-Fc fusion protein used in these examples has been described (WO 2007/014123, called "R4Mut4") (SEQ ID NO: 15). For transient expression in 293-6E cells, R4Mut4 was cloned into and expressed from vector pTT5 (Biotechnology Research Institute, Montreal, Canada). Chimeras of the R4Mut4 fusion protein were constructed using PCR and conventional mutagenesis techniques. The R4Mut4 chimeras were originally cloned into the mammalian expression vector pcDNA3.1 (Invitrogen) for transient expression in 293-6E cells.

The primary sequence and domain structure of the FGFR4 ECD moiety in the R4Mut4 construct is shown in FIG. 1. Table 1 lists various exemplary FGFR4 ECD-Fc fusion proteins used in these examples with names and brief descriptions.

TABLE 1

Exemplary FGFR4 ECD-Fc Fusion Proteins

| Protein Name | SEQ ID # | Brief Description | Short name |
| --- | --- | --- | --- |
| FGFR4ECD(delta17)-Fc | 15 | A native FGFR4 ECD fragment that has a 17 amino acid carboxy-terminal deletion from the FGFR4 ECD. | R4Mut4 |
| FGFR4ECD(ABMut1: delta17)-Fc | 52 | The D1-D2 linker from FGFR1 (amino acids 99 to 128, inclusive, of SEQ ID NO: 22) swapped into R4Mut4. | ABMut1 |
| FGFR4ECD(ABMut2: delta17)-Fc | 53 | A portion of the D1-D2 linker from FGFR1 (amino acids 99 to 126, inclusive, of SEQ ID NO: 22) swapped into R4Mut4. | ABMut2 |
| FGFR4ECD(ABMut3: delta17)-Fc | 91 | A portion of the D1-D2 linker from FGFR1 (amino acids 105 to 117, inclusive, of SEQ ID NO: 22) swapped into R4Mut4. | ABMut3 |
| FGFR4ECD(2Ig + Linker)-GS linker-Fc | 55 | A portion of the D1 domain of R4Mut4 is deleted, but the D1-D2 linker is retained with a GS linker | R4(2Ig + L) |
| FGFR4ECD(2Ig-Linker)-GS linker Fc | 56 | A portion of the D1 domain and the D1-D2 linker are deleted from R4Mut4 with a GS linker. | R4(2Ig-L) |
| FGFR4ECD(R4Mut4(N104D): delta17)-Fc | 79 | R4Mut4 with N104D point mutation. | R4Mut4(N104D) |
| FGFR4ECD(R4Mut4(P109D): delta17)-Fc | 80 | R4Mut4 with P109D point mutation. | R4Mut4(P109D) |
| FGFR4ECD(R4Mut4(R113E): delta17)-Fc | 81 | R4Mut4 with R113E point mutation. | R4Mut4(R113E) |
| FGFR4ECD(R4Mut4(S116E): delta17)-Fc | 82 | R4Mut4 with S116E point mutation. | R4Mut4(S116E) |

TABLE 1-continued

Exemplary FGFR4 ECD-Fc Fusion Proteins

| Protein Name | SEQ ID # | Brief Description | Short name |
|---|---|---|---|
| FGFR4ECD(R4Mut4(104-114): FGFR1(106-117): delta 17)-Fc | 83 | Residues 106 to 117, inclusive, from FGFR1 (SEQ ID NO: 22) swapped into R4Mut4. | R4(104-114): R1(106-117) |
| FGFR4ECD(R4Mut4(104-114): FGFR1(107-117): delta 17)-Fc | 84 | Residues 107 to 117, inclusive, from FGFR1 (SEQ ID NO: 22) swapped into R4Mut4. | R4(104-114): R1(107-117) |
| FGFR4ECD(R4Mut4(104-110): FGFR1(105-113): delta 17)-Fc | 85 | Residues 105 to 113, inclusive, from FGFR1 (SEQ ID NO: 22) swapped into R4Mut4. | R4(104-110): R1(105-113) |
| FGFR4ECD(R4Mut4(113-116): FGFR1(116-119): delta 17)-Fc | 86 | Residues 116 to 119, inclusive, from FGFR1 (SEQ ID NO: 22) swapped into R4Mut4. | R4(113-116): R1(116-119) |
| FGFR4ECD(R4Mut4(109-113): FGFR1(112-116): delta 17)-Fc | 87 | Residues 112 to 116, inclusive, from FGFR1 (SEQ ID NO: 22) swapped into R4Mut4. | R4(109-113): R1(112-116) |
| FGFR4ECD(ABMut1(N91A): delta 17)-Fc | 88 | ABMut1 with N91A point mutation. | ABMut1(N91A) |
| FGFR4ECD(ABMut1(N159A): delta 17)-Fc | 89 | ABMut1 with N159A point mutation. | ABMut1(N159A) |

For expression of the fusion proteins in CHO-S host cells, we used the pTT5 and pDEF38 (ICOS Corporation, Bothell, Wash.) vectors. R4Mut4 and the FGFR4 ECD-Fc variants were subcloned into the pTT5 and pDEF38 vectors using PCR and conventional subcloning techniques. For expression in DG44 cells, we used the pDEF38 vector.

Example 2

Transient Expression of Fusion Proteins in 293-6E and CHO-S Host Cells

FGFR4 ECD fusion proteins were transiently expressed in 293-6E cells. The R4Mut4/pTT5 expression vector, as described in Example 1, was designed to provide transient expression in 293-6E host cells. The 293-6E host cells used for expression were previously adapted to serum-free suspension culture in Free-Style medium (Invitrogen). The cells were transfected with the expression vector while in logarithmic growth phase (log phase growth) at a cell density of between $9 \times 10^5$/ml and $1.2 \times 10^6$/ml.

In order to transfect 500 ml of 293-6E cell suspension, a transfection mixture was made by mixing 500 micrograms (ug) of the expression vector DNA in 25 ml of sterile phosphate buffered saline (PBS) with 1 mg of polyethylenimine (from a 1 mg/ml solution in sterile water) in 25 ml of sterile PBS. This transfection mixture was incubated for 15 min at room temperature. Following incubation, the transfection mixture was added to the 293-6E cells in log phase growth for transfection. The cells and the transfection mixture were then incubated at 37° C. in 5% $CO_2$ for 24 hours. Following incubation, Trypton-N1 (Organotechnie S.A., La Courneuve, France; 20% solution in sterile FreeStyle medium) was added to a final concentration of 0.5% (v/v). The mixture was maintained at 37° C. and 5% $CO_2$ for about 6-8 days until the cells reached a density of about $3-4 \times 10^6$ cells/ml and showed a viability of >80%. To harvest the fusion protein from the cell culture medium, cells were pelleted at 400×g for 15 min at 4° C. and the supernatant was decanted. The supernatant was cleared of cell debris by centrifugation at 3,315×g for 15 min at 4° C. The cleared supernatant containing the fusion protein was then submitted for purification.

To provide small batches (1-2 mg) of R4Mut4 for in vivo study in a short period of time, transient production from suspension CHO-S host cells was carried out using the plasmid construct R4Mut4/pDEF38. Briefly, suspension CHO-S cells (Invitrogen) were cultured in Freestyle CHO expression medium supplemented with L-Glutamine (Invitrogen). The day before transfection, the CHO-S cells were seeded into a shaker flask at a density of about $5 \times 10^5$/ml, which then reached a density of about $1 \times 10^6$/ml on the day of transfection. In order to transfect 125 ml of cell suspension, 156.25 ug of the expression vector DNA was mixed with 2.5 ml of OptiPro serum free medium. 156.25 ul of FreestyleMax transfection reagent (Invitrogen) was separately mixed with 2.5 ml of OptiPro serum free medium. The transfection mixture was made by combining the DNA/OptiPro medium mixture and the FreestyleMax/Optipro medium mixture for 10 min at room temperature. Following incubation, the transfection mixture was added to the CHO-S cells. The cells and the transfection mixture were then incubated at 37° C. in 5% $CO_2$ for 6 days. Following incubation, the cell density was about $3.3-3.7 \times 10^6$/ml with a viability of about 82-88%. The supernatant from the culture was separated from the cells by centrifugation and collected for purification. Using this method, 1 mg of R4Mut4 can be produced from 400 ml of transiently transfected cell culture in about 1 week.

When indicated below, other FGFR4 ECDs were similarly produced by transient expression in CHO-S cells using the pDEF38 expression vectors described in Example 1.

Example 3

Purification of Expressed Proteins

FGFR4 ECD-Fc fusion proteins expressed from recombinant host cells were purified from the cell culture supernatant using a first purification step of Protein-A affinity chromatography, followed by a second purification step of butyl hydrophobic interaction chromatography. For the Protein-A affinity chromatography step, the components of the media were separated on a Mabselect Protein-A Sepharose column (GE Healthcare Bio-Sciences, Piscataway, N.J.), which will bind to the Fc region of the fusion molecule. The column was equilibrated with ten column volumes of a sterile buffer of 10 mM Tris, 100 mM NaCl, pH 8.0; then the cell culture supernatant was applied to the column. The column was washed with eight column volumes of sterile 10 mM Tris, 100 mM NaCl buffer, pH 8.0. The bound material, including R4Mut4, was then eluted at a rate of 10 ml/min with a one step elution using seven column volumes of elution buffer (100 mM glycine, 100 mM NaCl, pH 2.7). Ten ml fractions were collected in tubes containing one ml 1 M Tris pH 8.0 (Ambion, Austin, Tex.) to neutralize the eluate. Fractions comprising R4Mut4 were identified by gel electrophoresis and pooled.

For the second purification step of butyl hydrophobic interaction chromatography, pooled Protein-A column eluates were further purification on a butyl Sepharose column using a GE Healthcare Akta Purifier 100 (GE Healthcare Bio-Sciences, Piscataway, N.J.). The column was first equilibrated with five column volumes of sterile 10 mM Tris, 1 M ammonium sulfate, pH 8.0. A half volume of 3 M ammonium sulfate was then added to the eluate, which was then applied to the equilibrated butyl Sepharose column. The column was washed with four column volumes of the equilibration buffer and the bound material was eluted at a rate of five ml/min with a linear gradient starting at 50% equilibration buffer/50% elution buffer (10 mM Tris pH 8.0) and ending at 90% elution buffer/10% equilibration buffer over a total volume of 20 column volumes. Finally, an additional two column volumes of 100% elution buffer was used. Fourteen ml fractions were collected. R4Mut4 was eluted with approximately 40-60% elution buffer. The fractions containing the bulk of the R4Mut4 were identified by gel electrophoresis and pooled.

After purification, endotoxin levels were checked by the limulus amoebocyte lysate (LAL) assay (Cambrex, Walkersville, Md.). Endotoxin levels were confirmed to be less than or equal to 1 endotoxin unit (EU) per mg of R4Mut4.

Example 4

Stable Production in DG44 Cells

The expression vector R4Mut4/pDEF38, described in Example 1, was used to transfect DG44 host cells for stable production of R4Mut4. The untransfected DHFR-negative CHO cell line, DG44, was cultured in CHO-CD serum free medium (Irvine Scientific, Irvine, Calif.) supplemented with 8 mM L-Glutamine, 1× Hypoxanthine/Thymidine (HT; Invitrogen), and 18 ml/L of Pluronic-68 (Invitrogen). About 50 ug of R4Mut4/pDEF38 plasmid DNA was linearized by digestion with restriction enzyme PvuI, then precipitated by addition of ethanol, briefly air-dried, and then resuspended in 400 ul of sterile, distilled water. The DG44 cells were seeded into a shaker flask at a density of about $4\times10^5$/ml the day before transfection, and reached a density of about $0.8\times10^6$/ml on the day of transfection. The cells were harvested by centrifugation and about $1\times10^7$ cells were used per transfection.

For transfection, each cell pellet was resuspended in 0.1 ml of Nucleofector V solution and transferred to an Amaxa Nucleofector cuvette (Amaxa, Cologne, Germany). About 5 ug of the resuspended linearized plasmid DNA was added and mixed with the suspended DG44 cells in the cuvette. Cells were then electroporated with an Amaxa Nucleofector Device II using program U-024. Electroporated cells were cultured in CHO-CD medium for two days and then transferred into selective medium (CHO-CD serum free medium supplemented with 8 mM L-Glutamine and 18 ml/L Pluronic-68). The selective medium was changed once every week. After about 12 days, 1 ug/ml R3 Long IGF I growth factor (Sigma, St. Louis, Mo.) was added to the medium and the culture was continued for another week until confluent. The supernatants from pools of stably transfected cell lines were assayed by a sandwich R4Mut4 ELISA to determine the product titer. This transfection method generated an expression level of about 30 ug/ml of R4Mut4 from the pools of stably transfected cells.

Example 5

Transient Expression in 293-T Cells

The R4Mut4 (SEQ ID NO: 15) and ABMut1 (SEQ ID NO:52) fusion proteins were also transiently expressed in 293-T cells. For transient expression in 293-T cells, 0.5-0.65× $10^6$ cells were plated in each well of a 6-well plate (with or without poly-lysine coating) in 2 ml DMEM supplemented with 10% FBS. A Fugene™ (Roche) stock was made by combining 93.5 ul Optimem with 6.5 ul Fugene™, followed by a 5 min incubation. A DNA stock was made by combining 1.3 ug DNA with Optimem to a final volume of 100 ul. The Fugene™ stock (100 ul) was added to the DNA stock (100 ul), and the combined solution (200 ul) was added to one well of the 6-well plate. The solution was gently swirled and allowed to incubate with the cells for 30 min at room temperature. The cells were incubated in a humidified incubator with 5% $CO_2$. After 40 hours, the medium was removed, the cells were washed, and 1.5 ml Optimem was added to each well. Forty-nine hours after the medium was changed, the supernatant was collected, spun at 1,400 rpm for 10 min, and transferred to a fresh tube. The fusion proteins were purified from the culture medium as described in Example 3, except that only the first purification step of Protein-A affinity chromatography was used. Protein levels were determined using AlphaScreen (hu IgG AlphaLISA; Perkin-Elmer #AL205C).

Example 6

Additional Method of Transient Expression in CHO-S Cells

The R4Mut4 (SEQ ID NO: 15), ABMut1 (SEQ ID NO: 52), ABMut1(N91A) (SEQ ID NO: 88), and ABMut1 (N159A) (SEQ ID NO: 89) fusion proteins were transiently expressed in CHO-S cells. Briefly, a 500 ml culture of CHO-S cells (Invitrogen) was established by inoculating $0.5\times10^6$ cells/ml in fresh 37° C. Freestyle CHO medium containing 8 mM L-Glutamine (Invitrogen). The cells were grown in a 2 l plastic flask and were derived from a seed strain that was continuously maintained up to passage 20. The following day, the cells were counted and diluted, if necessary, to $1\times10^6$ cells/ml in 37° C. Freestyle CHO medium (Invitrogen) with a cell viability greater than 95%. The cells were transfected by transferring 10 ml of 37° C. OptiPRO SFM medium containing 8 mM L-Glutamine (dilution media) into two 50 ml tubes. To the first tube (A), 625 ul of FreestyleMax transfection reagent (Invitrogen) were added. To the second tube (B), 625 ug of DNA were added. Both tubes were gently mixed by inverting, and the contents of tube A were immediately added to tube B, followed by gentle mixing by inversion. The mixture was incubated at room temperature for between 10 to 20 min, and was then delivered drop-wise into the 500 ml cell culture in the 2 l culture flask while slowly swirling the flask. The culture was then transferred to an incubator at 37° C., 5% $CO_2$, 125 rpm. After six days, the cell viability was greater than 80%, and the culture supernatant was collected into a centrifuge bottle. The supernatant was centrifuged at 1,000×g for 10 min, transferred to a new centrifuge bottle, and centrifuged at 4,000×g for 10 min. The supernatant was collected into a new bottle and filtered through a 0.2 um filter. The supernatant was stored at 37° C. prior to the purification step. The fusion proteins were purified from the culture supernatant as described in Example 3, except that Q Sepharose anion exchange chromatography was used as the second purification step. Protein-A eluates were applied to a Q Sepharose HP column (GE Healthcare 17-1014-01) equilibrated with five column volumes of sterile buffer (10 mM Tris, 50 mM NaCl, pH 8.0). The column was washed with five column volumes of the same buffer and the bound material was eluted at a rate of five ml/min with a linear gradient of 15 column volumes of elution buffer (10 mM Tris, 2 M NaCl, pH 8.0), followed by five column volumes with 100% elution buffer. Fourteen ml fractions were collected and the fractions comprising the FGFR ECD-Fc were identified by gel electrophoresis and pooled. The FGFR4 ECD-Fc fusion proteins eluted with approximately 10-25% elution buffer. Protein levels were determined based on absorbance measurements at 280 nm.

Example 7

FGFR4 ECD-Fc Fusion Proteins Bind to FGF2 and/or FGF19

The FGF2 and FGF19 ligand binding affinity and kinetics of R4Mut4 and five different FGFR4 ECD variant-Fc fusion proteins (collectively "FGFR4 ECD proteins") were determined using Biacore® X surface plasmon resonance (SPR) technology (Uppsala, Sweden). FGF2 was selected because it is broadly expressed in adult tissue. FGF19 was selected because, in the absence of other protein cofactors, it binds specifically to FGFR4. Briefly, Protein-A was covalently linked to a CM5 chip, according to manufacturer's instructions. The FGFR4 ECD proteins were bound to the chip by interaction of the Fc domain with protein A. The FGFR4 ECD proteins were captured onto flow channels 2-4, while channel 1 served as a reference. FGF2 was purchased from Peprotech (Rocky Hill, N.J.) and FGF19 was purchased from R&D Systems. Each FGF ligand was injected at 5 concentrations (100 nM, 25 nM, 6.25 nM, 1.56 nM, and 0 nM) for 2 minutes and dissociation was monitored for 4 minutes. 50 uM Heparin was included in the running buffer. The association constant, dissociation constant, affinity, and binding capacity of each of the R4 proteins for FGF2 and FGF19 was calculated using the Biacore T100 Evaluation software package using the 1:1 binding model.

The results of that experiment are shown in Tables 2 and 3.

TABLE 2

| FGF2 Ligand Binding | | | | |
|---|---|---|---|---|
| Protein Name | $k_a$ (1/M · ms) | $k_d$ (1/s) · 1000 | $K_D$ (nM) | $R_{max}$ (RU) |
| R4Mut4 (experiment 1) | 59 | 0.23 | 3.90 | 46 |
| R4Mut4 (experiment 2) | 45 | 0.27 | 5.88 | 53 |
| ABMut1 | 160 | 0.27 | 1.70 | 56 |
| ABMut2 | 114 | 0.26 | 2.26 | 57 |
| ABMut3 | 242 | 0.35 | 1.44 | 58 |
| R4(2Ig + L) | 313 | 0.79 | 2.54 | 62 |
| R4(2Ig − L) | 306 | 0.73 | 2.40 | 51 |

TABLE 3

| FGF19 Ligand Binding | | | | |
|---|---|---|---|---|
| Protein Name | $k_a$ (1/M · ms) | $k_d$ (1/s) · 1000 | $K_D$ (nM) | $R_{max}$ (RU) |
| R4Mut4 (experiment 1) | 176 | 0.63 | 3.60 | 55 |
| R4Mut4 (experiment 2) | 184 | 0.61 | 3.32 | 50 |
| ABMut1 | 213 | 0.68 | 3.18 | 45 |
| ABMut2 | 250 | 0.64 | 2.58 | 44 |
| ABMut3 | 211 | 0.74 | 3.50 | 40 |
| R4(2Ig + L) | 80 | 2.76 | 34.31 | 26 |
| R4(2Ig − L) | 118 | 2.14 | 18.15 | 18 |

As shown in Tables 2 and 3, the FGFR4 ECD variant-Fc fusion proteins ABMut1 (SEQ ID NO: 52), ABMut2 (SEQ ID NO: 53), and ABMut3 (SEQ ID NO: 91) all bind to FGF2 and FGF19, as measured by the equilibrium dissociation constant ($K_D$). In addition, all had an affinity equal to or greater than the parental R4Mut4 for both FGF2 and FGF19 in that experiment.

In addition, FGFR4 2Ig ECD-Fc fusion proteins in which a portion of the D1 domain was deleted, in either the presence (R4(2Ig+L); SEQ ID NO: 55) or absence (R4(2Ig-L); SEQ ID NO: 56) of the D1-D2 linker region, bound FGF2 with an affinity equal to or greater than the parental R4Mut4 in that experiment, as measured by the equilibrium dissociation constant ($K_D$). Deletion of the D1 domain reduced binding to FGF19 by approximately ten-fold in the presence of the D1-D2 linker region (R4(2Ig+L)), and by approximately five-fold in the absence of the D1-D2 linker region (R4(2Ig-L)) in that experiment.

Those results show that all of the FGFR4 ECD proteins tested retained the ability to bind to FGF2 and/or FGF19, although the FGFR4 ECD proteins with the D1 domain deleted exhibited weaker binding to FGF19 than the parental or the acidic region chimeras in that experiment.

Example 8

FGF2 and FGF19 Competition ELISA Assays With FGFR4 ECD-Fc Fusion Proteins

FGF2 and FGF19 competition ELISA assays were carried out to determine the relative FGF2 and FGF19 ligand binding activities of ABMut1 (SEQ ID NO: 52) versus R4Mut4 (SEQ ID NO: 15), and of ABMut1 versus the FGFR4 ECD glycosylation mutant fusion proteins, ABMut1(N91A) (SEQ ID NO: 88) and ABMut1(N159A) (SEQ ID NO: 89). In these assays, ABMut1 was the reference standard, and R4Mut4, ABMut1(N91A), and ABMut1(N159A) were the test samples. Purified ABMut1, R4Mut4, ABMut1(N91A), and ABMut1(N159A) were serially diluted in sample diluent (PBS containing 1% BSA (fraction V; Sigma #A3059), 0.05% Tween-20, 200 ng/ml FGF2 (PreproTech #100-18B) or 50 ng/ml FGF19 (PreproTech #100-32), and 20 ug/ml heparin (Sigma #H3149)) to concentrations ranging from 1.5 ng/ml to 90,000 ng/ml. The protein mixtures were incubated for 60 min. A 96-well plate was incubated with 100 ul of 5 ug/ml R4Mut4 overnight at 4° C., washed three times, blocked in blocking buffer (PBS containing 1% BSA) for between one and two hours at room temperature, and washed three times. The protein mixtures (100 ul) were then transferred to the wells of the 96-well plate and incubated for one hour at room temperature with shaking.

In this assay, FGF2 or FGF19 that was not bound to the test samples or the reference standard during the initial incubation step would be free to bind to the surface-bound R4Mut4. The wells were washed three times using a plate washer, followed by detection using biotinylated anti-FGF2 antibody (R&D Systems #BAM233) or biotinylated anti-FGF19 antibody (R&D Systems #BAF969) with the VECTASTAIN ABC Kit (Vector Laboratories #PK-4000). Biotinylated anti-FGF2 antibody or biotinylated anti-FGF19 was diluted to 1 ug/ml in assay diluent (PBS containing 1% BSA and 0.05% Tween-20), and 100 ul was added to each well, followed by a one hour incubation at room temperature with shaking. The ABC solution was reconstituted by mixing three drops of solution A with three drops of solution B in 15 ml PBS, and the solution was allowed to stand for 30 min at room temperature. The plates were washed six times using a plate washer and 100 ul of the freshly reconstituted ABC solution were added to each well, followed by a 45 min to one hour incubation at room temperature. TMB substrate (100 ul) was added to each well, followed by incubation for 6 to 8 min at room temperature in the dark with gentle shaking. One hundred microliters of stop solution were added to each well, and the plates were mixed by tapping. The plate optical density (OD) was read at 450 nm with 570 nm subtraction.

The OD values were then plotted versus the protein concentration on a log scale to generate standard curves. The OD value for each well was directly proportional to the amount of bound FGF2 or FGF19, and was inversely proportional to the amount of active FGFR4 ECD-Fc fusion protein in the test solution. The concentration profiles for the test samples and the reference standards were fit using a 4-parameter logistic. The relative binding activity (% bioactivity) of each test sample was calculated by dividing the $IC_{50}$ value for the standard reference by the $IC_{50}$ value for the test sample, which was then multiplied by 100%. The relative FGF2 binding activities of R4Mut4, ABMut1(N91A), and ABMut1 (N159A) when ABMut1 was used as the reference standard in this assay were 69%, 44%, and 42%, respectively. The relative FGF19 binding activities of R4Mut4, ABMut1(N91A), and ABMut1(N159A) when ABMut1 was used as the reference standard in this assay were 103%, 51%, and 56%, respectively.

Taken together, the results of the competition ELISA assays and the Biacore® X SPR assays demonstrate that a series of FGFR4 ECD variants with different types of amino acid substitutions, deletions, and/or insertions maintain their ability to bind to FGF2 and/or FGF19.

Example 9

Systemic Delivery of an FGFR4 ECD Fusion Molecule Promotes Hair Growth in a Mouse Xenograft Model In experiments to determine whether an FGFR4 ECD fusion molecule ("R4Mut4") (SEQ ID NO: 15) exhibited antitumor activity in a cancer xenograft model, a noticeable effect on hair growth was observed. In those experiments, CB17 SCID mice (Charles River Labs, Wilmington, Mass.) between six and eight weeks of age were put into two groups of 10 mice per group, shaved on the right hind flank, and inoculated subcutaneously with $5 \times 10^6$ (100 ul) cells of the HCT116sc human colorectal cancer cell. The mice were given biweekly intravenous doses of 20 mg/kg R4Mut4 or vehicle control. The mice were monitored daily for signs of hair growth for 21 days. As shown in FIG. 3, the R4Mut4-treated mice showed substantial and clearly visible hair growth by day 15 when compared to vehicle-treated mice.

Example 10

Intraperitoneal Delivery of an FGFR4 ECD Fusion Molecule Promotes Hair Growth in Mice Fourteen-week-old female BalbC mice (Charles River Labs, Wilmington, Mass.) were weighed and sorted into 3 groups of 3 mice according to Table 4.

TABLE 4

Study Design for Testing the Effect of R4Mut4 on Hair Growth in Mice.

| Study Group | Dose Group | # Animals |
|---|---|---|
| 1 | BIW Vehicle | 3 |
| 2 | BIW R4Mut4 | 3 |
| 3 | Single Bolus R4Mut4 | 3 |

Mice were individually housed to avoid excessive grooming. All mice were shaved on the back prior to the first dose of R4Mut4 (SEQ ID NO: 15). Mice in Groups 1 and 2 received biweekly intraperitoneal injections of vehicle and 20 mg/kg R4Mut4, respectively. Mice in Group 3 received a single intraperitoneal injection of 20 mg/kg R4Mut4. Hair growth in the mice was monitored daily for up to 21 days. By days 14-15 post-dose, a substantial amount of clearly visible hair growth was observed in mice from Groups 2 and 3, whereas no visible hair growth was observed in animals from the vehicle-treated mice in Group 1 at this time. Similar results were seen in Sprague Dawley Rats.

Example 11

Systemic Delivery of an FGFR4 ECD Fusion Molecule Promotes Hair Growth in Mice

Eight-week-old female C57B1.6 mice (Charles River Labs, Wilmington, Mass.) were weighed and sorted into 5 treatment groups of 10 mice each based on body weight, as shown in Table 4. Five mice from each group were administered vehicle, and five mice from each group were administered 30 mg/kg the FGFR4 ECD fusion molecule ABMut1 (SEQ ID NO: 52) as a 0.2 cc intravenous infusion. The day of administration of test agent was designated as day 0. Immediately following the dosing, mice from study group 1 were shaved on the right flank. Mice from study groups 2, 3, 4, and 5 were shaved on day 2, 5, 7, and 9, respectively. Hair growth was monitored and recorded daily for up to 16 days after shaving.

TABLE 5

Study Design of Hair Growth Timecourse

| Study Group | # Animals | # Mice Administered Saline (Subgroup A) | # Mice Administered ABMut1 (Subgroup B) | Day of Test Agent Administration | Day of Shave |
|---|---|---|---|---|---|
| 1 | 10 | 5 | 5 | 0 | 0 |
| 2 | 10 | 5 | 5 | 0 | 2 |
| 3 | 10 | 5 | 5 | 0 | 5 |
| 4 | 10 | 5 | 5 | 0 | 7 |
| 5 | 10 | 5 | 5 | 0 | 9 |

Figure 4:
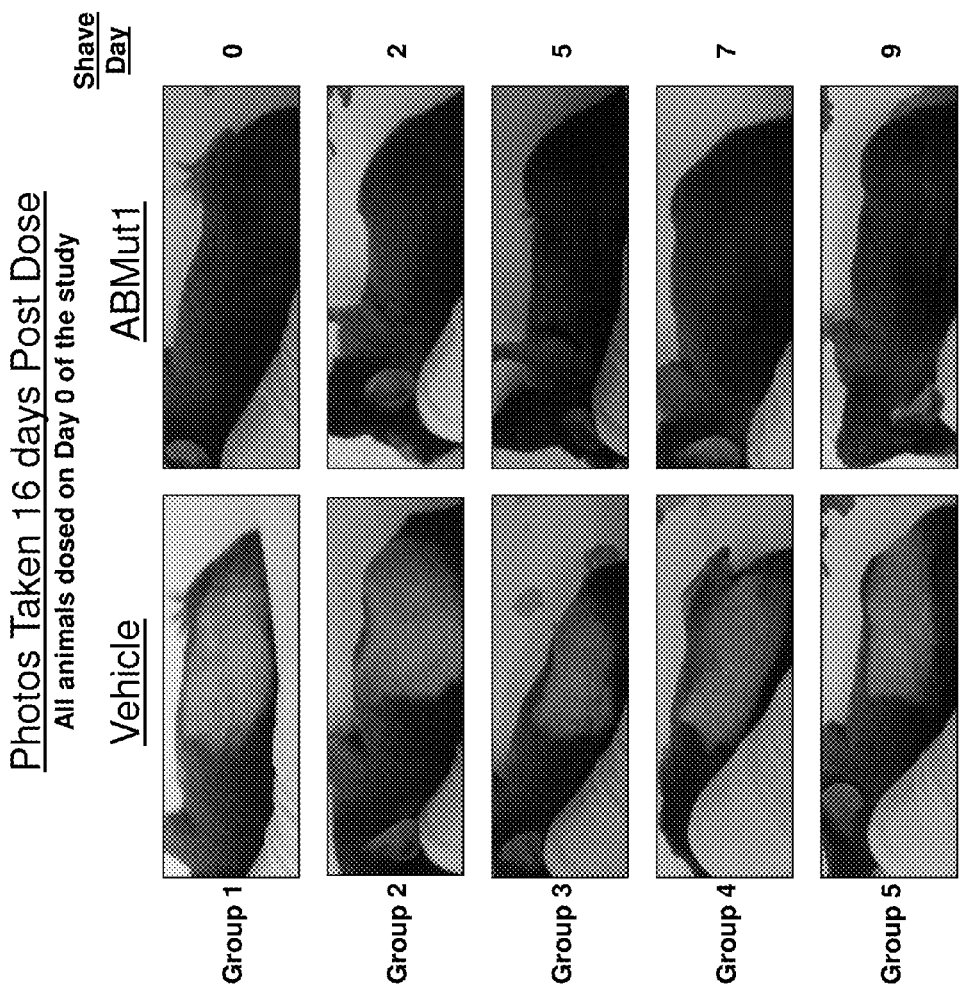
FIG. 4 shows that systemic delivery of ABMut1 (SEQ ID NO: 52) promotes a substantial amount of clearly visible hair growth by 16 days post-dose, whereas no visible hair growth was observed in vehicle-treated mice by 16 days post-dose. Five different groups of eight-week-old mice (designated 1-5) were administered vehicle (group A) or ABMut1 (30 mg/kg) (group B) by intravenous infusion on day 0. Mice in study groups 1, 2, 3, 4, and 5 were shaved on the right flank immediately following the dose, or on days 2, 5, 7, and 9, respectively. Hair growth was monitored and recorded daily for up to 16 days after shaving.

Observable hair growth appeared by day 9 as demonstrated by the presence of dark skin pigmentation and the lack of pale pink skin pigmentation in the shaved region in the freshly shaved mice of group 5B, and in the mice of groups 1B, 2B, 3B, and 4B, which were shaved on day 0, 2, 5, and 7, respectively. In contrast, the mice in vehicle-treated groups 1A, 2A, 3A, 4A, and 5A all had pale pink skin pigmentation in the shaved region on day 9. As shown in FIG. 4, by 16 days after dosing, all animals treated with ABMut1 exhibited a substantial amount of clearly visible hair growth in the shaved region, whereas the animals in the vehicle-treated groups did exhibit visible hair growth.

In experiments to determine whether local delivery of ABMut1 promotes hair growth in a manner similar to systemic delivery of ABMut1, mice were implanted with agarose beads bound to ABMut1 or vehicle. Affi-Gel Agarose Beads (Biorad, Hercules, Calif.) were washed 3 times and resuspended in Phosphate Buffered Saline. ABMut1 or an equivalent volume of vehicle was added directly to the prepared beads, and incubated at 37° C. for 1 hour with gentle agitation. Eight-week-old female C57B1.6 mice (Charles River Labs, Wilmington, Mass.) were weighed and sorted into groups of 10 mice based on weight. The entire back and both the right and left flank were shaved with electric clippers (Wahl, Sterling, Ill.). The animals were anesthetized with isoflurane prior to dose (Henry Schein, Melville, N.Y.). Agarose bead slurries were mixed thoroughly and drawn into a 1 ml syringe with a 25 g needle. The needle was inserted subcutaneously into the right flank of the anesthetized mouse, and 0.2 cc of the agarose bead slurry containing 3 mg/kg ABMut1 or vehicle was implanted with a rapid, forceful injection to drive the beads into the skin. The contralateral left side served as an uninjected internal control. Animals were examined daily for hair growth on both flanks. By 15 days post-injection, the ABMut1-treated mice showed a substantial amount of clearly visible, localized hair growth in the region surrounding the ABMut1-coated Affi-Gel Agarose Beads, whereas the vehicle-treated animals did not exhibit visible hair growth on day 15 post-injection.

Taken together, the results of these experiments provide evidence that the FGFR4 ECD fusion molecule induces anagen.

Example 12

Systemic Delivery of an FGFR4 ECD Fusion Molecule Induces Anagen in Hair Follicles in Mice Eight-week-old C57B16 mice (Charles River Labs, Wilmington, Mass.) were weighed and sorted into 8 groups of 5 mice each according to Table 6.

TABLE 6

Study Design for Histology Timecourse Analysis

| Study Group | # Animals | # Mice Administered Saline (Sub-group A) | # Mice Administered ABMut1 (Sub-group B) | Day of Test Agent Administration | Day of Histology |
|---|---|---|---|---|---|
| 1 | 10 | 5 | 5 | 0 | 3 |
| 2 | 10 | 5 | 5 | 0 | 5 |
| 3 | 10 | 5 | 5 | 0 | 7 |
| 4 | 10 | 5 | 5 | 0 | 14 |

Figure 5:
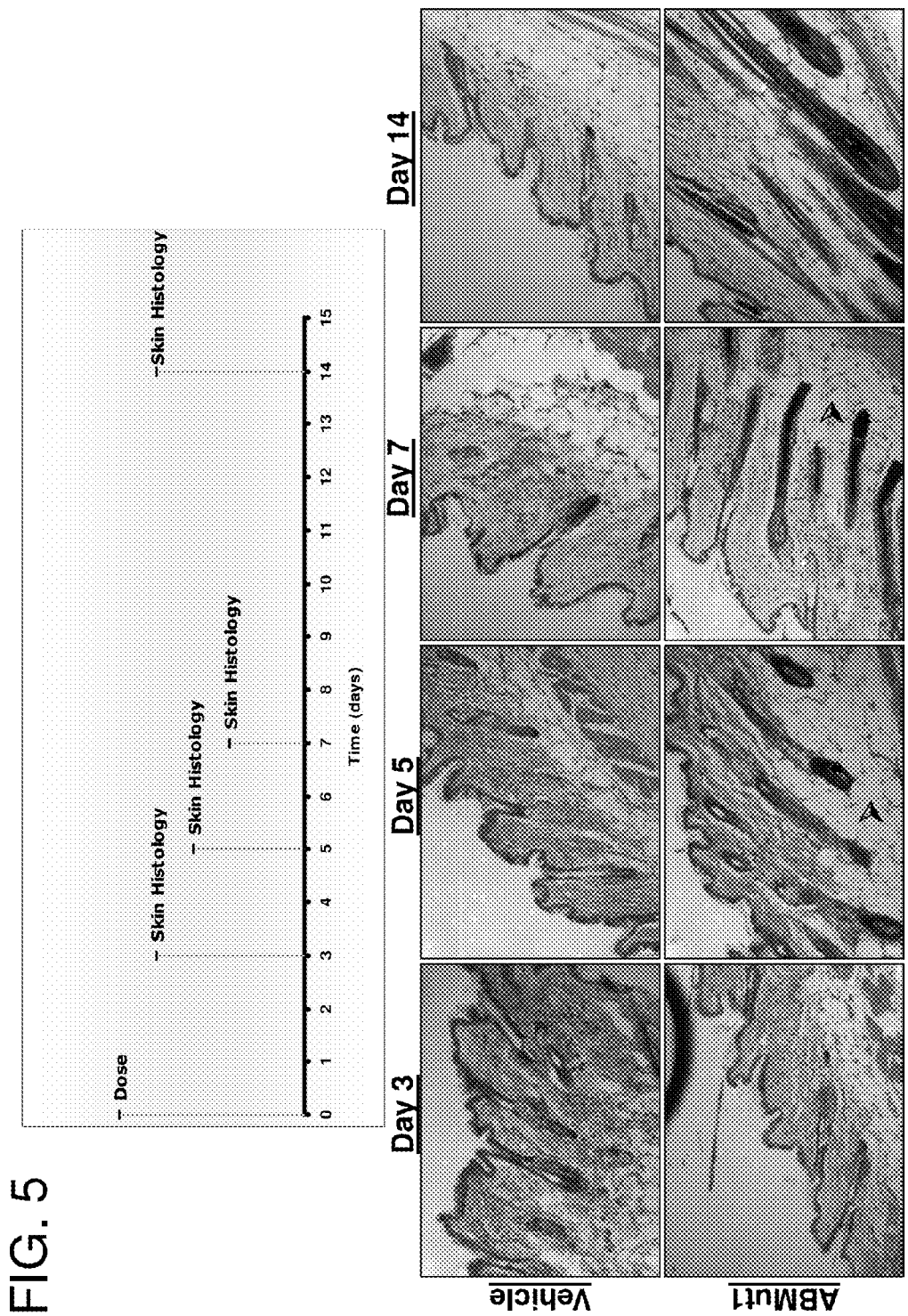
FIG. 5 shows that systemic delivery of ABMut1 (SEQ ID NO: 52) induces anagen in hair follicles of eight-week-old mice. Shown are paraffin-embedded skin biopsies stained with Haematoxylin/Eosin from vehicle- and ABMut1-treated mice at days 3, 5, 7, and 14 post-dose. By day 5 and continuing through day 14, mice treated with ABMut1 showed an elongation of the dermal papilla (*) into the fatty layer of the dermis (➤), showing that a single dose of ABMut1 can induce anagen (the growth phase of the hair cycle).

All mice were shaved on the right flank. Mice in subgroups A and B were given a single intravenous dose of 0.2 cc/mouse of Vehicle and ABMut1 (SEQ ID NO: 52), respectively. The mice were euthanized on the days shown in Table 6, and a 2 cm² skin biopsy was harvested from each mouse and fixed in neutral buffered saline for 12 hours. Samples were paraffin-embedded, and structural differences were visualized by Haematoxylin/Eosin staining. As shown in FIG. 5, by day 5 and continuing through day 14, the mice dosed with ABMut1 demonstrated an elongation of the dermal papilla (*) into the fatty layer of the dermis (➤), providing evidence that a single dose of ABMut1 can induce anagen.

Example 13

Subcutaneous Delivery of an FGFR1 ECD Fusion Molecule does not Promote Hair Growth in a Shaved Mouse Model 8 week old Female C57B1.6 mice (Charles River Labs, Wilmington, Mass.) were weighed and sorted into 2 groups of 10 mice according to Table 7.

TABLE 7

Study Design for Testing the Effect of an FGFR1 ECD Fusion Molecule on Hair Growth in a Shaved Mouse Model.

| Study Group | Dose Group | # Animals |
|---|---|---|
| 1 | Vehicle | 10 |
| 2 | FGFR1 ECD-Fc | 10 |

All mice were shaved on the entire back prior to dosing with Vehicle, or 10 mg/kg of an FGFR1 ECD fusion molecule (SEQ ID NO: 57). Mice were given a single subcutaneous injection on the midline of the back. Mice were monitored for hair growth for 28 days post dose. Hair growth was not observed in either group dosed (Data not shown).

Example 14

Intravenous Delivery of an FGFR2 ECD Fusion Molecule does not Promote Hair Growth in a Shaved Mouse Model 8 week old Female C57B1.6 mice (Charles River Labs, Wilmington, Mass.) were weighed and sorted into 3 groups of 10 mice according to Table 8.

TABLE 8

Study Design for Testing the Effect of an FGFR2 ECD Fusion Molecule on Hair Growth in a Shaved Mouse Model.

| Study Group | Dose Group | # Animals |
|---|---|---|
| 1 | Vehicle | 10 |
| 2 | FGFR2 ECD fusion | 10 |
| 3 | ABMut1 | 10 |

Figure 6:
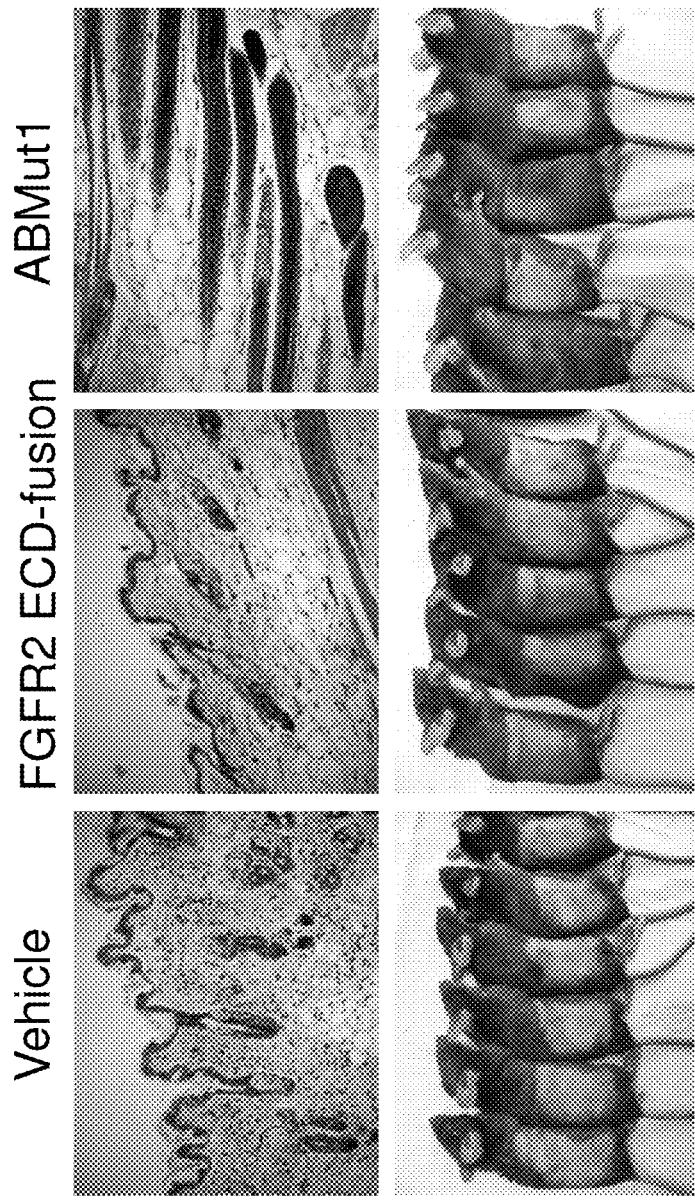
FIG. 6 shows that intravenous delivery of an FGFR2 ECD fusion molecule does not promote hair growth in a shaved mouse model. Shown are paraffin-embedded skin biopsies stained with Haematoxylin/Eosin from vehicle-, FGFR2 ECD-fusion-, and ABMut1-treated mice at day 15 post-dose. Mice treated with ABMut1 showed induction of anagen, whereas mice treated with vehicle or with an FGFR2 ECD fusion molecule did not show induction of anagen. By day 15, mice treated with ABMut1 showed hair growth. In contrast, mice treated with either vehicle or with the FGFR2 ECD fusion molecule did not show hair growth.

All mice were shaved on the right flank prior to dosing with Vehicle, or 20 mg/kg FGFR2 ECD fusion molecule or 10 mg/kg ABMut1. Mice were given a single intravenous injection. At day 15 post injection 5 animals from each group were subject to skin biopsy by removing a section of skin from the shaved region and fixing in neutral buffered formalin solution for 16 hours. Skin biopsies were paraffin embedded, sectioned and stained with H&E (Gladstone Histology Core, San Francisco, Calif.). The remaining 5 animals were observed for hair growth out to day 28. As demonstrated in FIG. 6, histology revealed induction of anagen in animals from group 3 that received a single intravenous injection of ABMut1, but no evidence of anagen induction in any animal in groups 1 (Vehicle) or 2 (FGFR2 ECD fusion molecule). Additionally, marked hair growth was observed by day 15 in animals in group 3 (FIG. 6), but no hair growth was not observed in animals from groups 1 and 2 up to 28 days post dosing.

Example 15

Subcutaneous Delivery of ABMut1 Results in Dose Responsive Hair Growth 8 week old Female C57B1.6 mice (Charles River Labs, Wilmington, Mass.) were weighed and sorted into 4 groups of 10 mice according to Table 9.

TABLE 9

Study Design for Testing the Dose Responsiveness of ABMut1 on Hair Growth in a Shaved Mouse Model.

| Study Group | Dose Group | # Animals | Dose (mg/kg) |
|---|---|---|---|
| 1 | Vehicle | 10 | 0 |
| 2 | ABMut1 | 10 | 0.1 |
| 3 | ABMut1 | 10 | 1 |
| 4 | ABMut1 | 10 | 10 |

Figure 7:
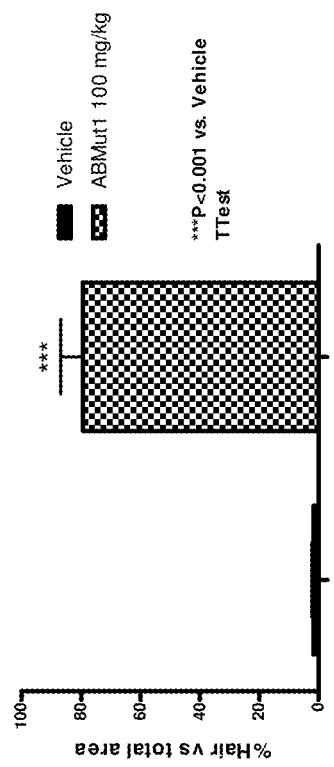
FIG. 7A and FIG. 7B show that subcutaneous delivery of ABMut1 results in dose responsive hair growth. (A) Mice were treated with 0 mg/kg (vehicle), 0.1 mg/kg, 1 mg/kg, or 10 mg/kg ABMut1. Shown is a graphical representation of hair growth at day 13 post-dose. (B) Mice were treated with a single dose of vehicle or 100 mg/kg ABMut1. Shown is a graphical representation of hair growth.
Figure 7:
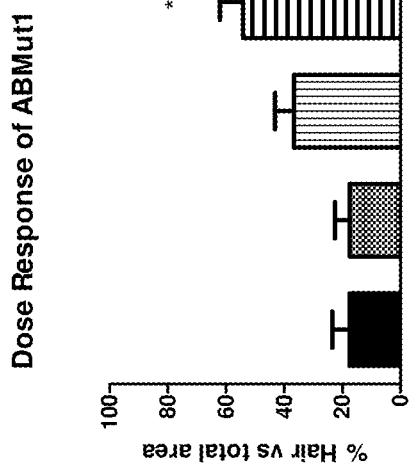

The entire belly and back of all mice was shaved and mice were injected with a single subcutaneous injection directly in the center of the belly along the midline. On day 13 animals were euthanized and the skin was shaved, removed, tacked down flat, and photographed. Hair growth was quantified by calculating total surface area vs. hair surface area in photographs Image J Analysis (NIH). As demonstrated in FIG. 7A, animals in group 2 did not demonstrate hair growth above what was quantified in the control group 1. Animals in group 3 demonstrated a 2 fold increase in hair growth compared to animals in group 1. Animals in group 4 demonstrated a significant 3 fold increase in hair growth compared to animals in group 1 suggesting a dose dependent hair growth response to subcutaneous exposure to ABMut1. In a subsequent study, using identical methods, animals given a single subcutaneous dose of 100 mg/kg ABMut1 demonstrated an 80% induction of hair growth compared to 2% in vehicle treated animals (FIG. 7B).

INDUSTRIAL APPLICABILITY

The FGFR4 ECDs and FGFR4 ECD fusion molecules described herein can be used to promote hair growth, which may be useful to subjects suffering from hair loss.

TABLE OF SEQUENCES

Table 10 provides certain sequences discussed herein. Solely for the sake of simplicity and not for any limiting reason, all FGFR sequences are shown without the signal peptide unless otherwise indicated.

TABLE 10

Sequences and Descriptions

| SEQ. ID. NO. | Description | Sequence |
|---|---|---|
| 1 | Native FGFR4 ECD | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 2 | FGFR4 ECD P115L | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDLSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 3 | FGFR4 ECD D276V | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGAVGFPY VQVLKTADIN SSEVEVLYLR NVSAEDAGEY TCLAGNSIGL SYQSAWLTVL PEEDPTWTAA APEARYTD |
| 4 | FGFR4 ECD T158A | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPAPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY |

TABLE 10-continued

Sequences and Descriptions

| SEQ. ID. NO. | Description | Sequence |
|---|---|---|
| | | VQVLKTADIN SSEVEVLYLR NVSAEDAGEY TCLAGNSIGL SYQSAWLTVL PEEDPTWTAA APEARYTD |
| 5 | FGFR4 ECD + linker + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTDGS EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 6 | FGFR4 ECD + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTDEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 7 | FGFR4 ECD Δ5 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APE |
| 8 | FGFR4 ECD Δ10 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTW |
| 9 | FGFR4 ECD Δ15 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEE |
| 10 | FGFR4 ECD Δ17 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |

TABLE 10-continued

Sequences and Descriptions

| SEQ. ID. NO. | Description | Sequence |
|---|---|---|
| 11 | FGFR4 ECD Δ18 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL |
| 12 | FGFR4 ECD Δ5 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVINGS SFGADGFPYV QVLKTADINS SEVEVLYLRN VSAEDAGEYT CLAGNSIGLS YQSAWLTVLP EEDPTWTAAA PEEPKSSDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 13 | FGFR4 ECD Δ10 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTEP KSSDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 14 | FGFR4 ECD Δ15 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEEPKSSDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSRDELTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 15 | FGFR4 ECD Δ17 + Fc (also called FGFR4ECD(delta17)-Fc and R4Mut4) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEPKSSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |

TABLE 10-continued

Sequences and Descriptions

| SEQ. ID. NO. | Description | Sequence |
|---|---|---|
| 16 | FGFR4 ECD Δ18 + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK |
| 17 | FGFR4 D1-D2 linker | DSLTSSNDDED PKSHRDPSNR HSYPQQ |
| 18 | FGFR4 P115L D1-D2 linker | DSLTSSNDDED PKSHRDLSNR HSYPQQ |
| 19 | FGFR4 exon 4 | DSLTSSNDDE DPKSHRDPSN RHSYPQ |
| 20 | FGFR4 P115L exon 4 | DSLTSSNDDE DPKSHRDLSN RHSYPQ |
| 21 | FGFR4 acid box | DDEDPKSHR |
| 22 | Native FGFR1 ECD | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |
| 23 | FGFR1 D1-D2 linker | DALPSSEDDDD DDDSSSEEKE TDNTKPNPV |
| 24 | FGFR1 exon 4 | DALPSSEDDD DDDDSSSEEK ETDNTKPN |
| 25 | FGFR1 acid box | EDDDDDDDSS SE |
| 26 | FGFR1 RM ECD | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNRMP VAPYWTSPEK MEKKLHAVPA AKTVKFKCPS SGTPNPTLRW LKNGKEFKPD HRIGGYKVRY ATWSIIMDSV VPSDKGNYTC IVENEYGSIN HTYQLDVVER SPHRPILQAG LPANKTVALG SNVEFMCKVY SDPQPHIQWL KHIEVNGSKI GPDNLPYVQI LKTAGVNTTD KEMEVLHLRN VSFEDAGEYT CLAGNSIGLS HHSAWLTVLE ALEERPAVMT SPLYLE |
| 27 | FGFR1 RM D1-D2 linker | DALPSSEDDDD DDDSSSEEKE TDNTKPNRMP V |
| 28 | FGFR1 RM exon 4 | DALPSSEDDD DDDDSSSEEK ETDNTKPNRM |
| 29 | FGFR4 ECD Δ17 R1 D1-D2 linker chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |
| 30 | FGFR4 ECD Δ17 R1 RM D1-D2 linker chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNRMPVA PYWTHPQRME KKLHAVPAGN TV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV |

TABLE 10-continued

Sequences and Descriptions

| SEQ. ID. NO. | Description | Sequence |
|---|---|---|
| | | INGSSFGADG FPYVQVLKTA DINSSEVEVL YLRNVSAEDA GEYTCLAGNS IGLSYQSAWL TVLP |
| 31 | FGFR4 ECD Δ17 R1 exon 4 chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNQAPYW THPQRMEKKL HAVPAGNTVK FR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 32 | FGFR4 ECD Δ17 R1 RM exon 4 chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNRMQAPYW THPQRMEKKL HAVPAGNTVK FR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 33 | FGFR4 ECD Δ17 R1 acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNEDDDDDDSS SEDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 34 | FGFR1 signal peptide | MWSWKCLLFWAVLVTATLCTA |
| 35 | FGFR2 signal peptide | MVSWGRFICLVVVTMATLSLA |
| 36 | FGFR3 signal peptide | MGAPACALALCVAVAIVAGASS |
| 37 | FGFR4 signal peptide | MRLLLALLGI LLSVPGPPVL S |
| 38 | FGFR4 N-terminal sequence | LEASEEVE |
| 39 | FGFR4 C-terminal sequence | LPEEDPTWTAA APEARYTD |
| 40 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 41 | Fc | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 42 | Fc | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 43 | FGFR4 V10I signal peptide | MRLLLALLGI LLSVPGPPVL S |
| 44 | FGFR4 ECD NΔ2 | ASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT |

TABLE 10-continued

Sequences and Descriptions

| SEQ. ID. NO. | Description | Sequence |
|---|---|---|
| | | IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 45 | FGFR4 ECD NΔ3 | SEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 46 | FGFR4 ECD NΔ5 | EVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 47 | FGFR4 ECD NΔ7 | ELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 48 | FGFR4 ECD NΔ8 | LE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 49 | FGFR4 ECD NΔ8 Δ17 | LE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 50 | FGFR4 ECD w/signal peptide | MRLLLALLGI LLSVPGPPVL SLEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEEDPTWTAA APEARYTD |
| 51 | FGFR1 RM ECD w/ signal peptide | MWSWKCLLFW AVLVTATLCT ARPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNRMP VAPYWTSPEK MEKKLHAVPA AKTVKFKCPS SGTPNPTLRW LKNGKEFKPD HRIGGYKVRY ATWSIIMDSV VPSDKGNYTC IVENEYGSIN HTYQLDVVER SPHRPILQAG LPANKTVALG SNVEFMCKVY SDPQPHIQWL KHIEVNGSKI GPDNLPYVQI LKTAGVNTTD |

TABLE 10-continued

Sequences and Descriptions

| SEQ. ID. NO. | Description | Sequence |
|---|---|---|
| | | KEMEVLHLRN VSFEDAGEYT CLAGNSIGLS HHSAWLTVLE ALEERPAVMT SPLYLE |
| 52 | FGFR4 ECD Δ17 R1 D1-D2 linker chimera + Fc (also called FGFR4ECD (ABMut1: delta 17)-Fc and ABMut1) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLPEPKSSD KTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 53 | FGFR4 ECD Δ17 R1 exon 4 chimera + Fc (also called FGFR4ECD(ABMut2: delta17)-Fc and ABMut2) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNQAPYW THPQRMEKKL HAVPAGNTVK FR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEPKSSD KTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 54 | FGFR4 ECD Δ17 R1 acid box chimera + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNEDDDDDDSS SEDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL PEPKSSD KTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK |
| 55 | FGFR4 ECD 2Ig + D1-D2 linker + GS linker + Fc (also called FGFR4ECD(2Ig + Linker)-Fc and R4(2Ig + L)) | LEASEEVELED SLTSSNDDED PKSHRDPSNR HSYPQQAPYW THPQRMEKKL HAVPAGNTVK FRCPAAGNPT PTIRWLKDGQ AFHGENRIGG IRLRHQHWSL VMESVVPSDR GTYTCLVENA VGSIRYNYLL DVLERSPHRP ILQAGLPANT TAVVGSDVEL LCKVYSDAQP HIQWLKHIVI NGSSFGADGF PYVQVLKTAD INSSEVEVLY LRNVSAEDAG EYTCLAGNSI GLSYQSAWLT VLPEEDPTWT AAAPEARYTD GSEPKSSDKT HTCPPCPAPE LLGGPSVFLF PPKPKDTLMI SRTPEVTCVV VDSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 56 | FGFR4 ECD 2Ig − D1-D2 linker + GS linker + Fc (also called FGFR4ECD(2II-Linker)-Fc and R4(2Ig-L)) | LEASEEVELEA PYWTHPQRME KKLHAVPAGN TVKFRCPAAG NPTPTIRWLK DGQAFHGENR IGGIRLRHQH WSLVMESVVP SDRGTYTCLV ENAVGSIRYN YLLDVLERSP HRPILQAGLP ANTTAVVGSD VELLCKVYSD AQPHIQWLKH IVINGSSFGA DGFPYVQVLK TADINSSEVE VLYLRNVSAE DAGEYTCLAG NSIGLSYQSA WLTVLPEEDP TWTAAAPEAR YTDGSEPKSS DKTHTCPPCP APELLGGPSV FLFPPKPKDT LMISRTPEVT CVVVDSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE |

TABLE 10-continued

Sequences and Descriptions

| SEQ. ID. NO. | Description | Sequence |
|---|---|---|
| | | WESNGQPENN YKTTPPVLDS DGSFFLYSKL TVDKSRWQQG NVFSCSVMHE ALHNHYTQKS LSLSPGK |
| 57 | FGFR1 ECD Δ14 + Fc (also called FGFR1ECD(delta14)-Fc and R1Mut4) | RPSPTLPEQA QPWGAPVEVE SFLVHPGDLL QLRCRLRDDV QSINWLRDGV QLAESNRTRI TGEEVEVQDS VPADSGLYAC VTSSPSGSDT TYFSVNVSDA LPSSEDDDDD DDSSSEEKET DNTKPNPVAP YWTSPEKMEK KLHAVPAAKT VKFKCPSSGT PNPTLRWLKN GKEFKPDHRI GGYKVRYATW SIIMDSVVPS DKGNYTCIVE NEYGSINHTY QLDVVERSPH RPILQAGLPA NKTVALGSNV EFMCKVYSDP QPHIQWLKHI EVNGSKIGPD NLPYVQILKT AGVNTTDKEM EVLHLRNVSF EDAGEYTCLA GNSIGLSHHS AWLTVLEALE PKSSDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 58 | FGFR4 ECD 2Ig + D1-D2 linker | LEASEEVELED SLTSSNDDED PKSHRDPSNR HSYPQQAPYW THPQRMEKKL HAVPAGNTVK FRCPAAGNPT PTIRWLKDGQ AFHGENRIGG IRLRHQHWSL VMESVVPSDR GTYTCLVENA VGSIRYNYLL DVLERSPHRP ILQAGLPANT TAVVGSDVEL LCKVYSDAQP HIQWLKHIVI NGSSFGADGF PYVQVLKTAD INSSEVEVLY LRNVSAEDAG EYTCLAGNSI GLSYQSAWLT VLPEEDPTWT AAAPEARYTD |
| 59 | FGFR4 ECD 2Ig − D1-D2 linker | LEASEEVELEA PYWTHPQRME KKLHAVPAGN TVKFRCPAAG NPTPTIRWLK DGQAFHGENR IGGIRLRHQH WSLVMESVVP SDRGTYTCLV ENAVGSIRYN YLLDVLERSP HRPILQAGLP ANTTAVVGSD VELLCKVYSD AQPHIQWLKH IVINGSSFGA DGFPYVQVLK TADINSSEVE VLYLRNVSAE DAGEYTCLAG NSIGLSYQSA WLTVLPEEDP TWTAAAPEAR YTD |
| 60 | FGFR4 long acid box | NDDEDPKSHR DPSNR |
| 61 | FGFR4 P115L long acid box | NDDEDPKSHR DLSNR |
| 62 | FGFR1 long acid box | EDDDDDDDSS SEEKETD |
| 63 | FGFR4 short acid box | DDED |
| 64 | FGFR4 ECD Δ17 R1 long acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDDSSSEEKETD HS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 65 | FGFR4 ECD Δ17 R1 short acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSN EDDDDDDD PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 66 | FGFR4 ECD Δ17 N104D | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSDDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 67 | FGFR4 ECD Δ17 P109D | LEASEEVELE PCLAPSLEQQ EQELTVALGQ PVRLCCGRAE RGGHWYKEGS RLAPAGRVRG WRGRLEIASF LPEDAGRYLC |

TABLE 10-continued

Sequences and Descriptions

| SEQ. ID. NO. | Description | Sequence |
|---|---|---|
| | | LARGSMIVLQ NLTLITGDSL TSSNDDEDDK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 68 | FGFR4 ECD Δ17 R113E | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHEDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 69 | FGFR4 ECD Δ17 S116E | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPENRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 70 | FGFR4 ECD Δ17 R4(104-114): R1(106-117) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 71 | FGFR4 ECD Δ17 R4(104-114): R1(107-117) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 72 | FGFR4 ECD Δ17 R4(104-110): R1 (105-113) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDS SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 73 | FGFR4 ECD Δ17 R4(113-116): R1(116-119) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SH EEKE NRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 74 | FGFR4 ECD Δ17 R4(109-113): R1(112-116) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDED DSSSE DPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY |

TABLE 10-continued

Sequences and Descriptions

| SEQ. ID. NO. | Description | Sequence |
|---|---|---|
| | | VQVLKTADIN SSEVEVLYLR NVSAEDAGEY TCLAGNSIGL SYQSAWLTVL P |
| 75 | FGFR4 ECD Δ17 R1 D1-D2 linker chimera (N91A) | LEASEEVELE PCLAPSLEQQ EQELTVALGQ PVRLCCGRAE RGGHWYKEGS RLAPAGRVRG WRGRLEIASF LPEDAGRYLC LARGSMIVLQ ALTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |
| 76 | FGFR4 ECD Δ17 R1 D1-D2 linker chimera (N159A) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGAP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |
| 77 | FGFR4 ECD Δ17 R1 long acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDDSSSEEKETD HS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 78 | FGFR4 ECD Δ17 R1 short acid box chimera-Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSN EDDDDDDD PK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 79 | FGFR4 ECD Δ17 N104D + Fc (also called FGFR4ECD(N104D):delta17)-Fc and R4Mut4(N104D)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSDDDEDPK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 80 | FGFR4 ECD Δ17 P109D + Fc (also called FGFR4ECD(R4Mut4 (P109D):delta17)-Fc and R4Mut4(P109D)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDDK SHRDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF |

TABLE 10-continued

Sequences and Descriptions

| SEQ. ID. NO. | Description | Sequence |
|---|---|---|
| | | NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 81 | FGFR4 ECD Δ17 R113E + Fc (also called FGFR4ECD(R4Mut4 (R113E): delta17)-Fc and R4Mut4(R113E)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHEDPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 82 | FGFR4 ECD Δ17 S116E + Fc (also called FGFR4ECD(R4Mut4 (S116E): delta17)-Fc and R4Mut4(S116E)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SHRDPENRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 83 | FGFR4 ECD Δ17 R4(104-114): R1(106-117) + Fc (also called FGFR4ECD(R4Mut4 (104-114): FGFR1(106-117): delta 17)-Fc and R4(104-114): R1(106-117)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 84 | FGFR4 ECD Δ17 R4(104-114): R1(107-117) + Fc (also called FGFR4ECD(R4Mut4 (104-114): FGFR1(107-117): delta17)-Fc and R4(104-114): R1(107-117)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS DDDDDDSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 85 | FGFR4 ECD Δ17 R4(104-110): R1(105-113) + Fc (also called FGFR4ECD(R4Mut4 | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDS SHRDPSNRHS YPQQAPYWTH PQRMEKKLHA VPAGNTVKFR CPAAGNPTPT IRWLKDGQAF HGENRIGGIR LRHQHWSLVM |

TABLE 10-continued

Sequences and Descriptions

| SEQ. ID. NO. | Description | Sequence |
|---|---|---|
| | (104-110): FGFR1(105-113): delta17)-Fc and R4(104-110): R1(105-113)) | ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 86 | FGFR4 ECD Δ17 R4(113-116): R1(116-119) + Fc (also called FGFR4ECD(R4Mut4 (113-116): FGFR1(116-119): delta 17)-Fc and R4(113-116): R1(116-119)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDEDPK SH EEKE NRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 87 | FGFR4 ECD Δ17 R4(109-113): R1(112-116) + Fc (also called FGFR4ECD(R4Mut4 (109-113): FGFR1(112-116): delta 17)-Fc and R4009-113): R1(112-116)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSSNDDED DSSSE DPSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 88 | FGFR4 ECD Δ17 R1 D1-D2 linker chimera (N91A) + Fc (also called FGFR4ECD(ABMut1 (N91A): delta 17)-Fc and ABMut1(N91A)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ ALTLITGDAL PSSEDDDDDD DSSSEEKETD NTKPNPVAPY WTHPQRMEKK LHAVPAGNTV KFRCPAAGNP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 89 | FGFR4 ECD Δ17 R1 D1-D2 linker chimera (N159A) + Fc (also called FGFR4ECD(ABMut1 (N159A): delta 17)-Fc andABMut1(N159A)) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDAL PSSEDDDDDD DSSSEEKETD NTKPNPVAPY WTHPQRMEKK LHAVPAGNTV KFRCPAAGAP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |

TABLE 10-continued

Sequences and Descriptions

| SEQ. ID. NO. | Description | Sequence |
|---|---|---|
| 90 | FGFR4 ECD Δ17 R4(104-114): R1(105-117) acid box chimera | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P |
| 91 | FGFR4 ECD Δ17 R4(104-114): R1(105-117) acid box chimera + Fc (also called FGF4ECD(ABMut3: delta17)-Fc or ABMut3) | LEASEEVELE PCLAPSLEQQ EQELTVALGQ PVRLCCGRAE RGGHWYKEGS RLAPAGRVRG WRGRLEIASF LPEDAGRYLC LARGSMIVLQ NLTLITGDSL TSS EDDDDDDSSSEE PSNRHS YPQQAPYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLDV LERSPHRPIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLTVL P EPKSSDKTHT CPPCPAPELL GGPSVFLFPP PKPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 92 | FGFR4 ECD Δ17 R1 D1-D2 linker chimera (N91A, N159A) | LEASEEVELE PCLAPSLEQQ EQELTVALGQ PVRLCCGRAE RGGHWYKEGS RLAPAGRVRG WRGRLEIASF LPEDAGRYLC LARGSMIVLQ ALTLITGDAL PSSEDDDDDD DSSSEEKETD NTKPNPVAPY WTHPQRMEKK LHAVPAGNTV KFRCPAAGAP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP |
| 93 | FGFR4 ECD Δ17 R1 D1-D2 linker chimera (N91A, N159A) + Fc | LEASEEVELE PCLAPSLEQQ EQELTVALGQ PVRLCCGRAE RGGHWYKEGS RLAPAGRVRG WRGRLEIASF LPEDAGRYLC LARGSMIVLQ ALTLITGDAL PSSEDDDDDD DSSSEEKETD NTKPNPVAPY WTHPQRMEKK LHAVPAGNTV KFRCPAAGAP TPTIRWLKDG QAFHGENRIG GIRLRHQHWS LVMESVVPSD RGTYTCLVEN AVGSIRYNYL LDVLERSPHR PILQAGLPAN TTAVVGSDVE LLCKVYSDAQ PHIQWLKHIV INGSSFGADG FPYVQVLKTA DINSSEVEVL YLRNVSAEDA GEYTCLAGNS IGLSYQSAWL TVLP EPKSSDKTHT CPPCPAPELL GGPSVFLFPP PKPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 94 | Fc | ESKYGPPCPP CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 95 | Fc | ERKSSVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 96 | FGFR1 ECD Δ14 | RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDSSSEEKE TDNKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL |

TABLE 10-continued

Sequences and Descriptions

| SEQ. ID. NO. | Description | Sequence |
|---|---|---|
| 97 | FGFR1 ECD w/signal peptide | MWSWKCLLFW AVLVTATLCT A RPSPTLPEQ AQPWGAPVEV ESFLVHPGDL LQLRCRLRDD VQSINWLRDG VQLAESNRTR ITGEEVEVQD SVPADSGLYA CVTSSPSGSD TTYFSVNVSD ALPSSEDDDD DDDSSSEEKE TDNTKPNPVA PYWTSPEKME KKLHAVPAAK TVKFKCPSSG TPNPTLRWLK NGKEFKPDHR IGGYKVRYAT WSIIMDSVVP SDKGNYTCIV ENEYGSINHT YQLDVVERSP HRPILQAGLP ANKTVALGSN VEFMCKVYSD PQPHIQWLKH IEVNGSKIGP DNLPYVQILK TAGVNTTDKE MEVLHLRNVS FEDAGEYTCL AGNSIGLSHH SAWLTVLEAL EERPAVMTSP LYLE |
| 98 | FGFR4 D1 Domain | LE PCLAPSLEQQ EQELTVALGQ PVRLCCGRAE RGGHWYKEGS RLAPAGRVRG WRGRLEIASF LPEDAGRYLC LARGSMIVLQ NLTLITG |
| 99 | FGFR4 D2 Domain | APYWTH PQRMEKKLHA VPAGNTVKFR CPAAGNPTPT IRWLKDGQAF HGENRIGGIR LRHQHWSLVM ESVVPSDRGT YTCLVENAVG SIRYNYLLD |
| 100 | FGFR4 T158A D2 Domain | APYWTH PQRMEKKLHA VPAGNTVKFR CPAAGNPAPT IRWLKDGQAF HGENRIGGIR LRHQHWSLVM ESVVPSDRGT YTCLVENAVG SIRYNYLLD |
| 101 | FGFR4 D3 Domain | PIL QAGLPANTTA VVGSDVELLC KVYSDAQPHI QWLKHIVING SSFGADGFPY VQVLKTADIN SSEVEVLYLR NVSAEDAGEY TCLAGNSIGL SYQSAWLT |
| 102 | FGFR4 D276V D3 Domain | PIL QAGLPANTTA VVGSDVELLC KVYSDAQPHI QWLKHIVING SSFGAVGFPY VQVLKTADIN SSEVEVLYLR NVSAEDAGEY TCLAGNSIGL SYQSAWLT |
| 103 | FGFR4 D2-D3 Linker | V LERSPHR |
| 104 | FGFR1 short acid box | EDDDDDDD |
| 105 | signal peptide + FGFR4 ECD Δ17 | MRLLLALLGVLLSVPGPPVLSLEASEEVELEPCLAPSLEQQEQE LTVALGQPVRLCCGRAERGGHWYKEGSRLAPAGRVRGWRGRLEI ASFLPEDAGRYLCLARGSMIVLQNLTLITGDSLTSSNDDEDPKS HRDPSNRHSYPQQAPYWTHPQRMEKKLHAVPAGNTVKFRCPAAG NPTPTIRWLKDGQAFHGENRIGGIRLRHQHWSLVMESVVPSDRG TYTCLVENAVGSIRYNYLLDVLERSPHRPILQAGLPANTTAVVG SDVELLCKVYSDAQPHIQWLKHIVINGSSFGADGFPYVQVLKTA DINSSEVEVLYLRNVSAEDAGEYTCLAGNSIGLSYQSAWLTVLP |

The invention claimed is:

1. A method of promoting hair growth or growing hair, comprising administering a Fibroblast Growth Factor Receptor 4 Extra-Cellular Domain (FGFR4 ECD) to a subject suffering from hair loss in an amount sufficient to promote hair growth or grow hair.

2. The method of claim 1, wherein the FGFR4 ECD is a native FGFR4 ECD.

3. The method of claim 1, wherein the FGFR4 ECD is an FGFR4 ECD acidic region mutein.

4. The method of claim 1, wherein the FGFR4 ECD is an FGFR4 ECD D1-D2 linker chimera.

5. The method of claim 1, wherein the amino acid sequence of the FGFR4 ECD is at least 95% identical to SEQ ID NO: 1, 2, 3, or 4.

6. The method of claim 1, wherein the amino acid sequence of the FGFR4 ECD is at least 99% identical to SEQ ID NO: 1, 2, 3, or 4.

7. The method of claim 1, wherein the amino acid sequence of the FGFR4 ECD has an amino acid sequence of SEQ ID NO: 10.

8. The method of claim 1, wherein the amino acid sequence of the FGFR4 ECD has an amino acid sequence of SEQ ID NO: 29.

9. The method of claim 1, wherein the subject is a rodent, simian, human, feline, canine, equine, bovine, porcine, ovine, caprine, mammalian laboratory animal, mammalian farm animal, mammalian sport animal, or mammalian pet.

10. The method of claim 9, wherein the subject is a human.

11. The method of claim 1, wherein the administering is intravenous, subcutaneous, intraperitoneal, topical, transdermal, or intradermal.

12. The method of claim 1, wherein the FGFR4 ECD is an FGFR4 ECD fusion molecule comprising an FGFR4 ECD polypeptide and a fusion partner.

13. The method of claim 12, wherein the FGFR4 ECD polypeptide is a native FGFR4 ECD.

14. The method of claim 12, wherein the FGFR4 ECD polypeptide is an FGFR4 ECD acidic region mutein.

15. The method of claim 12, wherein the FGFR4 ECD is an FGFR4 ECD D1-D2 linker chimera.

16. The method of claim 12, wherein the fusion partner is selected from an Fc, albumin, and polyethylene glycol.

17. The method of claim 16, wherein the fusion partner is an Fc.

18. The method of 12, wherein the FGFR4 ECD fusion molecule has an amino acid sequence of SEQ ID NO: 15.

19. The method of 12, wherein the FGFR4 ECD fusion molecule has an amino acid sequence of SEQ ID NO: 52.

20. The method of claim 12, wherein the subject is a rodent, simian, human, feline, canine, equine, bovine, porcine, ovine, caprine, mammalian laboratory animal, mammalian farm animal, mammalian sport animal, or mammalian pet.

21. The method of claim 20, wherein the subject is a human.

22. The method of claim 12, wherein the administering is intravenous, subcutaneous, intraperitoneal, topical, transdermal, or intradermal.

\* \* \* \* \*

SEQUENCE LISTING

<160> NUMBER OF SEQ ID NOS: 105

<210> SEQ ID NO 1
<211> LENGTH: 348
<212> TYPE: PRT
<213> ORGANISM: Artificial Sequence
<220> FEATURE:
<223> OTHER INFORMATION: Native FGFR4 ECD

<400> SEQUENCE: 1

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp
            340                 345

<210> SEQ ID NO 2
<211> LENGTH: 348
<212> TYPE: PRT
<213> ORGANISM: Artificial Sequence
<220> FEATURE:
<223> OTHER INFORMATION: FGFR4 ECD P115L

<400> SEQUENCE: 2

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

```
Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Leu Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp
            340                 345

<210> SEQ ID NO 3
<211> LENGTH: 348
<212> TYPE: PRT
<213> ORGANISM: Artificial Sequence
<220> FEATURE:
<223> OTHER INFORMATION: FGFR4 ECD D276V

<400> SEQUENCE: 3

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
```

```
                    100                 105                 110
Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Val Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp
            340                 345

<210> SEQ ID NO 4
<211> LENGTH: 348
<212> TYPE: PRT
<213> ORGANISM: Artificial Sequence
<220> FEATURE:
<223> OTHER INFORMATION: FGFR4 ECD T158A

<400> SEQUENCE: 4

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125
```

Thr His Pro Gln Arg Met Glu Lys Lys Leu His Ala Val Pro Ala Gly
            130                 135                 140

Asn Thr Val Lys Phe Arg Cys Pro Ala Ala Gly Asn Pro Ala Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp
            340                 345

<210> SEQ ID NO 5
<211> LENGTH: 582
<212> TYPE: PRT
<213> ORGANISM: Artificial Sequence
<220> FEATURE:
<223> OTHER INFORMATION: FGFR4 ECD + linker + Fc

<400> SEQUENCE: 5

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
            130                 135                 140

```
Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp Gly Ser Glu Pro
            340                 345                 350

Lys Ser Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
                420                 425                 430

Ser Thr Tyr Arg Val Val Ser Val Leu Thr Val Leu His Gln Asp Trp
            435                 440                 445

Leu Asn Gly Lys Glu Tyr Lys Cys Lys Val Ser Asn Lys Ala Leu Pro
        450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Asp Glu Leu Thr Lys Asn
                485                 490                 495

Gln Val Ser Leu Thr Cys Leu Val Lys Gly Phe Tyr Pro Ser Asp Ile
                500                 505                 510

Ala Val Glu Trp Glu Ser Asn Gly Gln Pro Glu Asn Asn Tyr Lys Thr
            515                 520                 525

Thr Pro Pro Val Leu Asp Ser Asp Gly Ser Phe Phe Leu Tyr Ser Lys
530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575
```

Ser Leu Ser Pro Gly Lys
        580

<210> SEQ ID NO 6
<211> LENGTH: 580
<212> TYPE: PRT
<213> ORGANISM: Artificial Sequence
<220> FEATURE:
<223> OTHER INFORMATION: FGFR4 ECD + Fc

<400> SEQUENCE: 6

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Ala Arg Tyr Thr Asp Glu Pro Lys Ser
            340                 345                 350

```
Ser Asp Lys Thr His Thr Cys Pro Pro Cys Pro Ala Pro Glu Leu Leu
        355                 360                 365

Gly Gly Pro Ser Val Phe Leu Phe Pro Pro Lys Pro Lys Asp Thr Leu
        370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
                405                 410                 415

Val His Asn Ala Lys Thr Lys Pro Arg Glu Glu Gln Tyr Asn Ser Thr
                    420                 425                 430

Tyr Arg Val Val Ser Val Leu Thr Val Leu His Gln Asp Trp Leu Asn
                435                 440                 445

Gly Lys Glu Tyr Lys Cys Lys Val Ser Asn Lys Ala Leu Pro Ala Pro
    450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Asp Glu Leu Thr Lys Asn Gln Val
                    485                 490                 495

Ser Leu Thr Cys Leu Val Lys Gly Phe Tyr Pro Ser Asp Ile Ala Val
                500                 505                 510

Glu Trp Glu Ser Asn Gly Gln Pro Glu Asn Asn Tyr Lys Thr Thr Pro
            515                 520                 525

Pro Val Leu Asp Ser Asp Gly Ser Phe Phe Leu Tyr Ser Lys Leu Thr
        530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
                565                 570                 575

Ser Pro Gly Lys
            580

<210> SEQ ID NO 7
<211> LENGTH: 343
<212> TYPE: PRT
<213> ORGANISM: Artificial Sequence
<220> FEATURE:
<223> OTHER INFORMATION: FGFR4 ECD delta5

<400> SEQUENCE: 7

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
```

```
                130                 135                 140
Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
                290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu
                340

<210> SEQ ID NO 8
<211> LENGTH: 337
<212> TYPE: PRT
<213> ORGANISM: Artificial Sequence
<220> FEATURE:
<223> OTHER INFORMATION: FGFR4 ECD delta10

<400> SEQUENCE: 8

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
                35                  40                  45

Gly Ser Arg Leu Ala Pro Ala Gly Arg Val Arg Gly Trp Arg Gly Arg
                50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
                100                 105                 110

Arg Asp Pro Ser Asn Arg His Ser Tyr Pro Gln Gln Ala Pro Tyr Trp
                115                 120                 125

Thr His Pro Gln Arg Met Glu Lys Lys Leu His Ala Val Pro Ala Gly
                130                 135                 140

Asn Thr Val Lys Phe Arg Cys Pro Ala Ala Gly Asn Pro Thr Pro Thr
145                 150                 155                 160
```

```
Ile Arg Trp Leu Lys Asp Gly Gln Ala Phe His Gly Glu Asn Arg Ile
            165                 170                 175

Gly Gly Ile Arg Leu Arg His Gln His Trp Ser Leu Val Met Glu Ser
        180                 185                 190

Val Val Pro Ser Asp Arg Gly Thr Tyr Thr Cys Leu Val Glu Asn Ala
    195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp

<210> SEQ ID NO 9
<211> LENGTH: 333
<212> TYPE: PRT
<213> ORGANISM: Artificial Sequence
<220> FEATURE:
<223> OTHER INFORMATION: FGFR4 ECD delta15

<400> SEQUENCE: 9

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
```

```
                    180                 185                 190
Val Val Pro Ser Asp Arg Gly Thr Tyr Thr Cys Leu Val Glu Asn Ala
            195                 200                 205
Val Gly Ser Ile Arg Tyr Asn Tyr Leu Leu Asp Val Leu Glu Arg Ser
        210                 215                 220
Pro His Arg Pro Ile Leu Gln Ala Gly Leu Pro Ala Asn Thr Thr Ala
225                 230                 235                 240
Val Val Gly Ser Asp Val Glu Leu Leu Cys Lys Val Tyr Ser Asp Ala
                245                 250                 255
Gln Pro His Ile Gln Trp Leu Lys His Ile Val Ile Asn Gly Ser Ser
            260                 265                 270
Phe Gly Ala Asp Gly Phe Pro Tyr Val Gln Val Leu Lys Thr Ala Asp
        275                 280                 285
Ile Asn Ser Ser Glu Val Glu Val Leu Tyr Leu Arg Asn Val Ser Ala
    290                 295                 300
Glu Asp Ala Gly Glu Tyr Thr Cys Leu Ala Gly Asn Ser Ile Gly Leu
305                 310                 315                 320
Ser Tyr Gln Ser Ala Trp Leu Thr Val Leu Pro Glu Glu
                325                 330

<210> SEQ ID NO 10
<211> LENGTH: 331
<212> TYPE: PRT
<213> ORGANISM: Artificial Sequence
<220> FEATURE:
<223> OTHER INFORMATION: FGFR4 ECD delta17

<400> SEQUENCE: 10

Leu Glu Ala Ser Glu Glu Val Glu Leu Glu Pro Cys Leu Ala Pro Ser
1               5                   10                  15
Leu Glu Gln Gln Glu Gln Glu Leu Thr Val Ala Leu Gly Gln Pro Val
            20                  25                  30
Arg Leu Cys Cys Gly Arg Ala Glu Arg Gly Gly His Trp Tyr Lys Glu
        35                  40                  45
Gly Ser Arg Leu Ala Pro Ala Gly Arg Val Arg Gly Trp Arg Gly Arg
    50                  55                  60
Leu Glu Ile Ala Ser Phe Leu Pro Glu Asp Ala Gly Arg Tyr Leu Cys
65                  70                  75                  80
Leu Ala Arg Gly Ser Met Ile Val Leu Gln Asn Leu Thr Leu Ile Thr
                85                  90                  95
Gly Asp Ser Leu Thr Ser Ser Asn Asp Asp Glu Asp Pro Lys Ser His
            100                 105                 110
Arg Asp Pro Ser Asn Arg His Ser Tyr Pro Gln Gln Ala Pro Tyr Trp
        115                 120                 125
Thr His Pro Gln Arg Met Glu Lys Lys Leu His Ala Val Pro Ala Gly
    130                 135                 140
Asn Thr Val Lys Phe Arg Cys Pro Ala Ala Gly Asn Pro Thr Pro Thr
145                 150                 155                 160
Ile Arg Trp Leu Lys Asp Gly Gln Ala Phe His Gly Glu Asn Arg Ile
                165                 170                 175
Gly Gly Ile Arg Leu Arg His Gln His Trp Ser Leu Val Met Glu Ser
            180                 185                 190
Val Val Pro Ser Asp Arg Gly Thr Tyr Thr Cys Leu Val Glu Asn Ala
        195                 200                 205
Val Gly Ser Ile Arg Tyr Asn Tyr Leu Leu Asp Val Leu Glu Arg Ser
    210                 215                 220
```

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
        260                 265                 270

Phe Gly Ala Asp Gly Phe Pro Tyr Val Gln Val Leu Lys Thr Ala Asp
    275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
            325                 330

<210> SEQ ID NO 11
<211> LENGTH: 330
<212> TYPE: PRT
<213> ORGANISM: Artificial Sequence
<220> FEATURE:
<223> OTHER INFORMATION: FGFR4 ECD delta18

<400> SEQUENCE: 11

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
            85                  90                  95

Gly Asp Ser Leu Thr Ser Ser Asn Asp Asp Glu Asp Pro Lys Ser His
        100                 105                 110

Arg Asp Pro Ser Asn Arg His Ser Tyr Pro Gln Gln Ala Pro Tyr Trp
    115                 120                 125

Thr His Pro Gln Arg Met Glu Lys Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
            165                 170                 175

Gly Gly Ile Arg Leu Arg His Gln His Trp Ser Leu Val Met Glu Ser
        180                 185                 190

Val Val Pro Ser Asp Arg Gly Thr Tyr Thr Cys Leu Val Glu Asn Ala
    195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

```
Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu
            325                 330

<210> SEQ ID NO 12
<211> LENGTH: 575
<212> TYPE: PRT
<213> ORGANISM: Artificial Sequence
<220> FEATURE:
<223> OTHER INFORMATION: FGFR4 ECD delta5 + Fc

<400> SEQUENCE: 12

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
```

```
                290                 295                 300
Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Ala Ala Ala Pro Glu Glu Pro Lys Ser Ser Asp Lys Thr His
                340                 345                 350

Thr Cys Pro Pro Cys Pro Ala Pro Glu Leu Leu Gly Gly Pro Ser Val
                355                 360                 365

Phe Leu Phe Pro Pro Lys Pro Lys Asp Thr Leu Met Ile Ser Arg Thr
                370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Thr Tyr Arg Val Val Ser
                420                 425                 430

Val Leu Thr Val Leu His Gln Asp Trp Leu Asn Gly Lys Glu Tyr Lys
                435                 440                 445

Cys Lys Val Ser Asn Lys Ala Leu Pro Ala Pro Ile Glu Lys Thr Ile
450                 455                 460

Ser Lys Ala Lys Gly Gln Pro Arg Glu Pro Gln Val Tyr Thr Leu Pro
465                 470                 475                 480

Pro Ser Arg Asp Glu Leu Thr Lys Asn Gln Val Ser Leu Thr Cys Leu
                485                 490                 495

Val Lys Gly Phe Tyr Pro Ser Asp Ile Ala Val Glu Trp Glu Ser Asn
                500                 505                 510

Gly Gln Pro Glu Asn Asn Tyr Lys Thr Thr Pro Pro Val Leu Asp Ser
                515                 520                 525

Asp Gly Ser Phe Phe Leu Tyr Ser Lys Leu Thr Val Asp Lys Ser Arg
                530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 13
<211> LENGTH: 570
<212> TYPE: PRT
<213> ORGANISM: Artificial Sequence
<220> FEATURE:
<223> OTHER INFORMATION: FGFR4 ECD delta10 + Fc

<400> SEQUENCE: 13

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
                35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95
```

-continued

```
Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Glu Asp Pro Thr
                325                 330                 335

Trp Thr Glu Pro Lys Ser Ser Asp Lys Thr His Thr Cys Pro Pro Cys
            340                 345                 350

Pro Ala Pro Glu Leu Leu Gly Gly Pro Ser Val Phe Leu Phe Pro Pro
        355                 360                 365

Lys Pro Lys Asp Thr Leu Met Ile Ser Arg Thr Pro Glu Val Thr Cys
370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
        435                 440                 445

Lys Ala Leu Pro Ala Pro Ile Glu Lys Thr Ile Ser Lys Ala Lys Gly
450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
```

```
                  515                 520                 525
Leu Tyr Ser Lys Leu Thr Val Asp Lys Ser Arg Trp Gln Gln Gly Asn
530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys
                565                 570

<210> SEQ ID NO 14
<211> LENGTH: 565
<212> TYPE: PRT
<213> ORGANISM: Artificial Sequence
<220> FEATURE:
<223> OTHER INFORMATION: FGFR4 ECD delta15 + Fc

<400> SEQUENCE: 14

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320
```

```
Ser Tyr Gln Ser Ala Trp Leu Thr Val Leu Pro Glu Glu Pro Lys
            325                 330                 335

Ser Ser Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
            355                 360                 365

Leu Met Ile Ser Arg Thr Pro Glu Val Thr Cys Val Val Val Asp Val
        370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
    450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Pro Gly Lys
            565

<210> SEQ ID NO 15
<211> LENGTH: 563
<212> TYPE: PRT
<213> ORGANISM: Artificial Sequence
<220> FEATURE:
<223> OTHER INFORMATION: FGFR4 ECD delta17 + Fc (also called FGFR4ECD
      (delta17)-Fc and R4Mut4)

<400> SEQUENCE: 15

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110
```

```
Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
    195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
    275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
    355                 360                 365

Ile Ser Arg Thr Pro Glu Val Thr Cys Val Val Val Asp Val Ser His
    370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
    435                 440                 445

Glu Lys Thr Ile Ser Lys Ala Lys Gly Gln Pro Arg Glu Pro Gln Val
    450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
    515                 520                 525

Asp Lys Ser Arg Trp Gln Gln Gly Asn Val Phe Ser Cys Ser Val Met
```

```
                  530                 535                 540
His Glu Ala Leu His Asn His Tyr Thr Gln Lys Ser Leu Ser Leu Ser
545                 550                 555                 560

Pro Gly Lys

<210> SEQ ID NO 16
<211> LENGTH: 562
<212> TYPE: PRT
<213> ORGANISM: Artificial Sequence
<220> FEATURE:
<223> OTHER INFORMATION: FGFR4 ECD delta18 + Fc

<400> SEQUENCE: 16

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Glu Pro Lys Ser Ser Asp
                325                 330                 335
```

-continued

```
Lys Thr His Thr Cys Pro Pro Cys Pro Ala Pro Glu Leu Leu Gly Gly
            340                 345                 350

Pro Ser Val Phe Leu Phe Pro Pro Lys Pro Lys Asp Thr Leu Met Ile
        355                 360                 365

Ser Arg Thr Pro Glu Val Thr Cys Val Val Val Asp Val Ser His Glu
    370                 375                 380

Asp Pro Glu Val Lys Phe Asn Trp Tyr Val Asp Gly Val Glu Val His
385                 390                 395                 400

Asn Ala Lys Thr Lys Pro Arg Glu Glu Gln Tyr Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Ala Leu Pro Ala Pro Ile Glu
        435                 440                 445

Lys Thr Ile Ser Lys Ala Lys Gly Gln Pro Arg Glu Pro Gln Val Tyr
    450                 455                 460

Thr Leu Pro Pro Ser Arg Asp Glu Leu Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Lys Leu Thr Val Asp
        515                 520                 525

Lys Ser Arg Trp Gln Gln Gly Asn Val Phe Ser Cys Ser Val Met His
    530                 535                 540

Glu Ala Leu His Asn His Tyr Thr Gln Lys Ser Leu Ser Leu Ser Pro
545                 550                 555                 560

Gly Lys

<210> SEQ ID NO 17
<211> LENGTH: 27
<212> TYPE: PRT
<213> ORGANISM: Artificial Sequence
<220> FEATURE:
<223> OTHER INFORMATION: FGFR4 D1-D2 linker

<400> SEQUENCE: 17

Asp Ser Leu Thr Ser Ser Asn Asp Glu Asp Pro Lys Ser His Arg
1               5                   10                  15

Asp Pro Ser Asn Arg His Ser Tyr Pro Gln Gln
            20                  25

<210> SEQ ID NO 18
<211> LENGTH: 27
<212> TYPE: PRT
<213> ORGANISM: Artificial Sequence
<220> FEATURE:
<223> OTHER INFORMATION: FGFR4 P115L D1-D2 linker

<400> SEQUENCE: 18

Asp Ser Leu Thr Ser Ser Asn Asp Glu Asp Pro Lys Ser His Arg
1               5                   10                  15

Asp Leu Ser Asn Arg His Ser Tyr Pro Gln Gln
            20                  25

<210> SEQ ID NO 19
<211> LENGTH: 26
<212> TYPE: PRT
```

<213> ORGANISM: Artificial Sequence
<220> FEATURE:
<223> OTHER INFORMATION: FGFR4 exon 4

<400> SEQUENCE: 19

Asp Ser Leu Thr Ser Ser Asn Asp Asp Glu Asp Pro Lys Ser His Arg
1               5                   10                  15

Asp Pro Ser Asn Arg His Ser Tyr Pro Gln
            20                  25

<210> SEQ ID NO 20
<211> LENGTH: 26
<212> TYPE: PRT
<213> ORGANISM: Artificial Sequence
<220> FEATURE:
<223> OTHER INFORMATION: FGFR4 P115L exon 4

<400> SEQUENCE: 20

Asp Ser Leu Thr Ser Ser Asn Asp Asp Glu Asp Pro Lys Ser His Arg
1               5                   10                  15

Asp Leu Ser Asn Arg His Ser Tyr Pro Gln
            20                  25

<210> SEQ ID NO 21
<211> LENGTH: 9
<212> TYPE: PRT
<213> ORGANISM: Artificial Sequence
<220> FEATURE:
<223> OTHER INFORMATION: FGFR4 acid box

<400> SEQUENCE: 21

Asp Asp Glu Asp Pro Lys Ser His Arg
1               5

<210> SEQ ID NO 22
<211> LENGTH: 353
<212> TYPE: PRT
<213> ORGANISM: Artificial Sequence
<220> FEATURE:
<223> OTHER INFORMATION: Native FGFR1 ECD

<400> SEQUENCE: 22

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
                35                  40                  45

Gly Val Gln Leu Ala Glu Ser Asn Arg Thr Arg Ile Thr Gly Glu Glu
        50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

```
Pro Asn Pro Thr Leu Arg Trp Leu Lys Asn Gly Lys Glu Phe Lys Pro
                165                 170                 175
Asp His Arg Ile Gly Gly Tyr Lys Val Arg Tyr Ala Thr Trp Ser Ile
            180                 185                 190
Ile Met Asp Ser Val Val Pro Ser Asp Lys Gly Asn Tyr Thr Cys Ile
        195                 200                 205
Val Glu Asn Glu Tyr Gly Ser Ile Asn His Thr Tyr Gln Leu Asp Val
    210                 215                 220
Val Glu Arg Ser Pro His Arg Pro Ile Leu Gln Ala Gly Leu Pro Ala
225                 230                 235                 240
Asn Lys Thr Val Ala Leu Gly Ser Asn Val Glu Phe Met Cys Lys Val
                245                 250                 255
Tyr Ser Asp Pro Gln Pro His Ile Gln Trp Leu Lys His Ile Glu Val
            260                 265                 270
Asn Gly Ser Lys Ile Gly Pro Asp Asn Leu Pro Tyr Val Gln Ile Leu
        275                 280                 285
Lys Thr Ala Gly Val Asn Thr Thr Asp Lys Glu Met Glu Val Leu His
    290                 295                 300
Leu Arg Asn Val Ser Phe Glu Asp Ala Gly Glu Tyr Thr Cys Leu Ala
305                 310                 315                 320
Gly Asn Ser Ile Gly Leu Ser His His Ser Ala Trp Leu Thr Val Leu
                325                 330                 335
Glu Ala Leu Glu Glu Arg Pro Ala Val Met Thr Ser Pro Leu Tyr Leu
            340                 345                 350
Glu

<210> SEQ ID NO 23
<211> LENGTH: 30
<212> TYPE: PRT
<213> ORGANISM: Artificial Sequence
<220> FEATURE:
<223> OTHER INFORMATION: FGFR1 D1-D2 linker

<400> SEQUENCE: 23

Asp Ala Leu Pro Ser Ser Glu Asp Asp Asp Asp Asp Asp Ser Ser
1               5                   10                  15
Ser Glu Glu Lys Glu Thr Asp Asn Thr Lys Pro Asn Pro Val
            20                  25                  30

<210> SEQ ID NO 24
<211> LENGTH: 28
<212> TYPE: PRT
<213> ORGANISM: Artificial Sequence
<220> FEATURE:
<223> OTHER INFORMATION: FGFR1 exon 4

<400> SEQUENCE: 24

Asp Ala Leu Pro Ser Ser Glu Asp Asp Asp Asp Asp Asp Ser Ser
1               5                   10                  15
Ser Glu Glu Lys Glu Thr Asp Asn Thr Lys Pro Asn
            20                  25

<210> SEQ ID NO 25
<211> LENGTH: 12
<212> TYPE: PRT
<213> ORGANISM: Artificial Sequence
<220> FEATURE:
<223> OTHER INFORMATION: FGFR1 acid box

<400> SEQUENCE: 25
```

Glu Asp Asp Asp Asp Asp Asp Ser Ser Glu
1               5                   10

<210> SEQ ID NO 26
<211> LENGTH: 355
<212> TYPE: PRT
<213> ORGANISM: Artificial Sequence
<220> FEATURE:
<223> OTHER INFORMATION: FGFR1 RM ECD

<400> SEQUENCE: 26

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
                20                  25                  30

Arg Cys Arg Leu Arg Asp Asp Val Gln Ser Ile Asn Trp Leu Arg Asp
            35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Arg Met
        115                 120                 125

Pro Val Ala Pro Tyr Trp Thr Ser Pro Glu Lys Met Glu Lys Lys Leu
130                 135                 140

His Ala Val Pro Ala Ala Lys Thr Val Lys Phe Lys Cys Pro Ser Ser
145                 150                 155                 160

Gly Thr Pro Asn Pro Thr Leu Arg Trp Leu Lys Asn Gly Lys Glu Phe
                165                 170                 175

Lys Pro Asp His Arg Ile Gly Gly Tyr Lys Val Arg Tyr Ala Thr Trp
            180                 185                 190

Ser Ile Ile Met Asp Ser Val Val Pro Ser Asp Lys Gly Asn Tyr Thr
    195                 200                 205

Cys Ile Val Glu Asn Glu Tyr Gly Ser Ile Asn His Thr Tyr Gln Leu
210                 215                 220

Asp Val Val Glu Arg Ser Pro His Arg Pro Ile Leu Gln Ala Gly Leu
225                 230                 235                 240

Pro Ala Asn Lys Thr Val Ala Leu Gly Ser Asn Val Glu Phe Met Cys
                245                 250                 255

Lys Val Tyr Ser Asp Pro Gln Pro His Ile Gln Trp Leu Lys His Ile
            260                 265                 270

Glu Val Asn Gly Ser Lys Ile Gly Pro Asp Asn Leu Pro Tyr Val Gln
    275                 280                 285

Ile Leu Lys Thr Ala Gly Val Asn Thr Thr Asp Lys Glu Met Glu Val
    290                 295                 300

Leu His Leu Arg Asn Val Ser Phe Glu Asp Ala Gly Glu Tyr Thr Cys
305                 310                 315                 320

Leu Ala Gly Asn Ser Ile Gly Leu Ser His His Ser Ala Trp Leu Thr
                325                 330                 335

Val Leu Glu Ala Leu Glu Glu Arg Pro Ala Val Met Thr Ser Pro Leu
            340                 345                 350

Tyr Leu Glu
        355

<210> SEQ ID NO 27
<211> LENGTH: 32
<212> TYPE: PRT
<213> ORGANISM: Artificial Sequence
<220> FEATURE:
<223> OTHER INFORMATION: FGFR1 RM D1-D2 linker

<400> SEQUENCE: 27

Asp Ala Leu Pro Ser Ser Glu Asp Asp Asp Asp Asp Ser Ser
1               5                   10                  15

Ser Glu Glu Lys Glu Thr Asp Asn Thr Lys Pro Asn Arg Met Pro Val
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: FGFR1 RM exon 4

<400> SEQUENCE: 28

Asp Ala Leu Pro Ser Ser Glu Asp Asp Asp Asp Asp Ser Ser
1               5                   10                  15

Ser Glu Glu Lys Glu Thr Asp Asn Thr Lys Pro Asn Arg Met
            20                  25                  30

<210> SEQ ID NO 29
<211> LENGTH: 334
<212> TYPE: PRT
<213> ORGANISM: Artificial Sequence
<220> FEATURE:
<223> OTHER INFORMATION: FGFR4 ECD delta17 R1 D1-D2 linker chimera

<400> SEQUENCE: 29

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

```
Met Glu Ser Val Val Pro Ser Asp Arg Gly Thr Tyr Thr Cys Leu Val
            195                 200                 205

Glu Asn Ala Val Gly Ser Ile Arg Tyr Asn Tyr Leu Leu Asp Val Leu
210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
            245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
            275                 280                 285

Thr Ala Asp Ile Asn Ser Ser Glu Val Glu Val Leu Tyr Leu Arg Asn
            290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro
            325                 330

<210> SEQ ID NO 30
<211> LENGTH: 336
<212> TYPE: PRT
<213> ORGANISM: Artificial Sequence
<220> FEATURE:
<223> OTHER INFORMATION: FGFR4 ECD delta17 R1 RM D1-D2 linker chimera

<400> SEQUENCE: 30

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
            85                  90                  95

Gly Asp Ala Leu Pro Ser Ser Asp Asp Asp Asp Asp Asp Asp Asp Ser
            100                 105                 110

Ser Ser Glu Glu Lys Glu Thr Asp Asn Thr Lys Pro Asn Arg Met Pro
            115                 120                 125

Val Ala Pro Tyr Trp Thr His Pro Gln Arg Met Glu Lys Lys Leu His
130                 135                 140

Ala Val Pro Ala Gly Asn Thr Val Lys Phe Arg Cys Pro Ala Ala Gly
145                 150                 155                 160

Asn Pro Thr Pro Thr Ile Arg Trp Leu Lys Asp Gly Gln Ala Phe His
            165                 170                 175

Gly Glu Asn Arg Ile Gly Gly Ile Arg Leu Arg His Gln His Trp Ser
            180                 185                 190

Leu Val Met Glu Ser Val Val Pro Ser Asp Arg Gly Thr Tyr Thr Cys
            195                 200                 205

Leu Val Glu Asn Ala Val Gly Ser Ile Arg Tyr Asn Tyr Leu Leu Asp
210                 215                 220
```

-continued

```
Val Leu Glu Arg Ser Pro His Arg Pro Ile Leu Gln Ala Gly Leu Pro
225                 230                 235                 240

Ala Asn Thr Thr Ala Val Val Gly Ser Asp Val Glu Leu Leu Cys Lys
                245                 250                 255

Val Tyr Ser Asp Ala Gln Pro His Ile Gln Trp Leu Lys His Ile Val
            260                 265                 270

Ile Asn Gly Ser Ser Phe Gly Ala Asp Gly Phe Pro Tyr Val Gln Val
        275                 280                 285

Leu Lys Thr Ala Asp Ile Asn Ser Ser Glu Val Glu Val Leu Tyr Leu
    290                 295                 300

Arg Asn Val Ser Ala Glu Asp Ala Gly Glu Tyr Thr Cys Leu Ala Gly
305                 310                 315                 320

Asn Ser Ile Gly Leu Ser Tyr Gln Ser Ala Trp Leu Thr Val Leu Pro
                325                 330                 335

<210> SEQ ID NO 31
<211> LENGTH: 333
<212> TYPE: PRT
<213> ORGANISM: Artificial Sequence
<220> FEATURE:
<223> OTHER INFORMATION: FGFR4 ECD delta17 R1 exon 4 chimera

<400> SEQUENCE: 31

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
```

```
                260                 265                 270
Ser Ser Phe Gly Ala Asp Gly Phe Pro Tyr Val Gln Val Leu Lys Thr
            275                 280                 285

Ala Asp Ile Asn Ser Ser Glu Val Glu Val Leu Tyr Leu Arg Asn Val
        290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
                325                 330

<210> SEQ ID NO 32
<211> LENGTH: 335
<212> TYPE: PRT
<213> ORGANISM: Artificial Sequence
<220> FEATURE:
<223> OTHER INFORMATION: FGFR4 ECD delta17 R1 RM exon 4 chimera

<400> SEQUENCE: 32

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Arg Met Gln
        115                 120                 125

Ala Pro Tyr Trp Thr His Pro Gln Arg Met Glu Lys Lys Leu His Ala
    130                 135                 140

Val Pro Ala Gly Asn Thr Val Lys Phe Arg Cys Pro Ala Ala Gly Asn
145                 150                 155                 160

Pro Thr Pro Thr Ile Arg Trp Leu Lys Asp Gly Gln Ala Phe His Gly
                165                 170                 175

Glu Asn Arg Ile Gly Gly Ile Arg Leu Arg His Gln His Trp Ser Leu
            180                 185                 190

Val Met Glu Ser Val Val Pro Ser Asp Arg Gly Thr Tyr Thr Cys Leu
        195                 200                 205

Val Glu Asn Ala Val Gly Ser Ile Arg Tyr Asn Tyr Leu Leu Asp Val
    210                 215                 220

Leu Glu Arg Ser Pro His Arg Pro Ile Leu Gln Ala Gly Leu Pro Ala
225                 230                 235                 240

Asn Thr Thr Ala Val Val Gly Ser Asp Val Glu Leu Leu Cys Lys Val
                245                 250                 255

Tyr Ser Asp Ala Gln Pro His Ile Gln Trp Leu Lys His Ile Val Ile
            260                 265                 270

Asn Gly Ser Ser Phe Gly Ala Asp Gly Phe Pro Tyr Val Gln Val Leu
        275                 280                 285

Lys Thr Ala Asp Ile Asn Ser Ser Glu Val Glu Val Leu Tyr Leu Arg
    290                 295                 300
```

Asn Val Ser Ala Glu Asp Ala Gly Glu Tyr Thr Cys Leu Ala Gly Asn
305                 310                 315                 320

Ser Ile Gly Leu Ser Tyr Gln Ser Ala Trp Leu Thr Val Leu Pro
            325                 330                 335

<210> SEQ ID NO 33
<211> LENGTH: 334
<212> TYPE: PRT
<213> ORGANISM: Artificial Sequence
<220> FEATURE:
<223> OTHER INFORMATION: FGFR4 ECD delta17 R1 acid box chimera

<400> SEQUENCE: 33

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Glu Asp Asp Asp Asp Asp Asp Asp
            100                 105                 110

Ser Ser Ser Glu Asp Pro Ser Asn Arg His Ser Tyr Pro Gln Gln Ala
        115                 120                 125

Pro Tyr Trp Thr His Pro Gln Arg Met Glu Lys Lys Leu His Ala Val
130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro
                325                 330

-continued

```
<210> SEQ ID NO 34
<211> LENGTH: 21
<212> TYPE: PRT
<213> ORGANISM: Artificial Sequence
<220> FEATURE:
<223> OTHER INFORMATION: FGFR1 signal peptide

<400> SEQUENCE: 34

Met Trp Ser Trp Lys Cys Leu Leu Phe Trp Ala Val Leu Val Thr Ala
1               5                   10                  15

Thr Leu Cys Thr Ala
            20

<210> SEQ ID NO 35
<211> LENGTH: 21
<212> TYPE: PRT
<213> ORGANISM: Artificial Sequence
<220> FEATURE:
<223> OTHER INFORMATION: FGFR2 signal peptide

<400> SEQUENCE: 35

Met Val Ser Trp Gly Arg Phe Ile Cys Leu Val Val Val Thr Met Ala
1               5                   10                  15

Thr Leu Ser Leu Ala
            20

<210> SEQ ID NO 36
<211> LENGTH: 22
<212> TYPE: PRT
<213> ORGANISM: Artificial Sequence
<220> FEATURE:
<223> OTHER INFORMATION: FGFR3 signal peptide

<400> SEQUENCE: 36

Met Gly Ala Pro Ala Cys Ala Leu Ala Leu Cys Val Ala Val Ala Ile
1               5                   10                  15

Val Ala Gly Ala Ser Ser
            20

<210> SEQ ID NO 37
<211> LENGTH: 21
<212> TYPE: PRT
<213> ORGANISM: Artificial Sequence
<220> FEATURE:
<223> OTHER INFORMATION: FGFR4 signal peptide

<400> SEQUENCE: 37

Met Arg Leu Leu Leu Ala Leu Leu Gly Ile Leu Leu Ser Val Pro Gly
1               5                   10                  15

Pro Pro Val Leu Ser
            20

<210> SEQ ID NO 38
<211> LENGTH: 8
<212> TYPE: PRT
<213> ORGANISM: Artificial Sequence
<220> FEATURE:
<223> OTHER INFORMATION: FGFR4 N-terminal sequence

<400> SEQUENCE: 38

Leu Glu Ala Ser Glu Glu Val Glu
1               5

<210> SEQ ID NO 39
<211> LENGTH: 19
```

```
<212> TYPE: PRT
<213> ORGANISM: Artificial Sequence
<220> FEATURE:
<223> OTHER INFORMATION: FGFR4 C-terminal sequence

<400> SEQUENCE: 39

Leu Pro Glu Glu Asp Pro Thr Trp Thr Ala Ala Ala Pro Glu Ala Arg
1               5                   10                  15

Tyr Thr Asp

<210> SEQ ID NO 40
<211> LENGTH: 232
<212> TYPE: PRT
<213> ORGANISM: Artificial Sequence
<220> FEATURE:
<223> OTHER INFORMATION: Fc C237S

<400> SEQUENCE: 40

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 41
<211> LENGTH: 228
<212> TYPE: PRT
<213> ORGANISM: Artificial Sequence
<220> FEATURE:
<223> OTHER INFORMATION: Fc

<400> SEQUENCE: 41

Glu Arg Lys Cys Cys Val Glu Cys Pro Pro Cys Pro Ala Pro Pro Val
1               5                   10                  15
```

```
Ala Gly Pro Ser Val Phe Leu Phe Pro Pro Lys Pro Lys Asp Thr Leu
         20                  25                  30

Met Ile Ser Arg Thr Pro Glu Val Thr Cys Val Val Val Asp Val Ser
             35                  40                  45

His Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Phe Arg Val Val Ser Val Leu Thr Val His Gln Asp Trp Leu Asn
                 85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
            115                 120                 125

Val Tyr Thr Leu Pro Pro Ser Arg Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220

Ser Pro Gly Lys
225

<210> SEQ ID NO 42
<211> LENGTH: 229
<212> TYPE: PRT
<213> ORGANISM: Artificial Sequence
<220> FEATURE:
<223> OTHER INFORMATION: Fc

<400> SEQUENCE: 42

Glu Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
             35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
```

```
                      145                 150                 155                 160
Val Glu Trp Glu Ser Asn Gly Gln Pro Glu Asn Asn Tyr Lys Thr Thr
                    165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 43
<211> LENGTH: 21
<212> TYPE: PRT
<213> ORGANISM: Artificial Sequence
<220> FEATURE:
<223> OTHER INFORMATION: FGFR4 V10I signal peptide

<400> SEQUENCE: 43

Met Arg Leu Leu Leu Ala Leu Leu Gly Ile Leu Leu Ser Val Pro Gly
1               5                   10                  15

Pro Pro Val Leu Ser
            20

<210> SEQ ID NO 44
<211> LENGTH: 346
<212> TYPE: PRT
<213> ORGANISM: Artificial Sequence
<220> FEATURE:
<223> OTHER INFORMATION: FGFR4 ECD Ndelta2

<400> SEQUENCE: 44

Ala Ser Glu Glu Val Glu Leu Glu Pro Cys Leu Ala Pro Ser Leu Glu
1               5                   10                  15

Gln Gln Glu Gln Glu Leu Thr Val Ala Leu Gly Gln Pro Val Arg Leu
            20                  25                  30

Cys Cys Gly Arg Ala Glu Arg Gly Gly His Trp Tyr Lys Glu Gly Ser
        35                  40                  45

Arg Leu Ala Pro Ala Gly Arg Val Arg Gly Trp Arg Gly Arg Leu Glu
    50                  55                  60

Ile Ala Ser Phe Leu Pro Glu Asp Ala Gly Arg Tyr Leu Cys Leu Ala
65                  70                  75                  80

Arg Gly Ser Met Ile Val Leu Gln Asn Leu Thr Leu Ile Thr Gly Asp
                85                  90                  95

Ser Leu Thr Ser Ser Asn Asp Asp Glu Asp Pro Lys Ser His Arg Asp
            100                 105                 110

Pro Ser Asn Arg His Ser Tyr Pro Gln Gln Ala Pro Tyr Trp Thr His
        115                 120                 125

Pro Gln Arg Met Glu Lys Lys Leu His Ala Val Pro Ala Gly Asn Thr
    130                 135                 140

Val Lys Phe Arg Cys Pro Ala Ala Gly Asn Pro Thr Pro Thr Ile Arg
145                 150                 155                 160

Trp Leu Lys Asp Gly Gln Ala Phe His Gly Glu Asn Arg Ile Gly Gly
                165                 170                 175

Ile Arg Leu Arg His Gln His Trp Ser Leu Val Met Glu Ser Val Val
            180                 185                 190

Pro Ser Asp Arg Gly Thr Tyr Thr Cys Leu Val Glu Asn Ala Val Gly
```

```
              195                 200                 205
Ser Ile Arg Tyr Asn Tyr Leu Leu Asp Val Leu Glu Arg Ser Pro His
    210                 215                 220

Arg Pro Ile Leu Gln Ala Gly Leu Pro Ala Asn Thr Thr Ala Val Val
225                 230                 235                 240

Gly Ser Asp Val Glu Leu Leu Cys Lys Val Tyr Ser Asp Ala Gln Pro
                245                 250                 255

His Ile Gln Trp Leu Lys His Ile Val Ile Asn Gly Ser Ser Phe Gly
                260                 265                 270

Ala Asp Gly Phe Pro Tyr Val Gln Val Leu Lys Thr Ala Asp Ile Asn
                275                 280                 285

Ser Ser Glu Val Glu Val Leu Tyr Leu Arg Asn Val Ser Ala Glu Asp
                290                 295                 300

Ala Gly Glu Tyr Thr Cys Leu Ala Gly Asn Ser Ile Gly Leu Ser Tyr
305                 310                 315                 320

Gln Ser Ala Trp Leu Thr Val Leu Pro Glu Glu Asp Pro Thr Trp Thr
                325                 330                 335

Ala Ala Ala Pro Glu Ala Arg Tyr Thr Asp
                340                 345

<210> SEQ ID NO 45
<211> LENGTH: 345
<212> TYPE: PRT
<213> ORGANISM: Artificial Sequence
<220> FEATURE:
<223> OTHER INFORMATION: FGFR4 ECD Ndelta3

<400> SEQUENCE: 45

Ser Glu Glu Val Glu Leu Glu Pro Cys Leu Ala Pro Ser Leu Glu Gln
1               5                   10                  15

Gln Glu Gln Glu Leu Thr Val Ala Leu Gly Gln Pro Val Arg Leu Cys
                20                  25                  30

Cys Gly Arg Ala Glu Arg Gly Gly His Trp Tyr Lys Glu Gly Ser Arg
            35                  40                  45

Leu Ala Pro Ala Gly Arg Val Arg Gly Trp Arg Gly Arg Leu Glu Ile
    50                  55                  60

Ala Ser Phe Leu Pro Glu Asp Ala Gly Arg Tyr Leu Cys Leu Ala Arg
65                  70                  75                  80

Gly Ser Met Ile Val Leu Gln Asn Leu Thr Leu Ile Thr Gly Asp Ser
                85                  90                  95

Leu Thr Ser Ser Asn Asp Asp Glu Asp Pro Lys Ser His Arg Asp Pro
                100                 105                 110

Ser Asn Arg His Ser Tyr Pro Gln Gln Ala Pro Tyr Trp Thr His Pro
            115                 120                 125

Gln Arg Met Glu Lys Lys Leu His Ala Val Pro Ala Gly Asn Thr Val
    130                 135                 140

Lys Phe Arg Cys Pro Ala Ala Gly Asn Pro Thr Pro Thr Ile Arg Trp
145                 150                 155                 160

Leu Lys Asp Gly Gln Ala Phe His Gly Glu Asn Arg Ile Gly Gly Ile
                165                 170                 175

Arg Leu Arg His Gln His Trp Ser Leu Val Met Glu Ser Val Val Pro
                180                 185                 190

Ser Asp Arg Gly Thr Tyr Thr Cys Leu Val Glu Asn Ala Val Gly Ser
            195                 200                 205

Ile Arg Tyr Asn Tyr Leu Leu Asp Val Leu Glu Arg Ser Pro His Arg
    210                 215                 220
```

```
Pro Ile Leu Gln Ala Gly Leu Pro Ala Asn Thr Thr Ala Val Val Gly
225                 230                 235                 240

Ser Asp Val Glu Leu Leu Cys Lys Val Tyr Ser Asp Ala Gln Pro His
                245                 250                 255

Ile Gln Trp Leu Lys His Ile Val Ile Asn Gly Ser Ser Phe Gly Ala
            260                 265                 270

Asp Gly Phe Pro Tyr Val Gln Val Leu Lys Thr Ala Asp Ile Asn Ser
        275                 280                 285

Ser Glu Val Glu Val Leu Tyr Leu Arg Asn Val Ser Ala Glu Asp Ala
    290                 295                 300

Gly Glu Tyr Thr Cys Leu Ala Gly Asn Ser Ile Gly Leu Ser Tyr Gln
305                 310                 315                 320

Ser Ala Trp Leu Thr Val Leu Pro Glu Glu Asp Pro Thr Trp Thr Ala
                325                 330                 335

Ala Ala Pro Glu Ala Arg Tyr Thr Asp
                340                 345
```

<210> SEQ ID NO 46
<211> LENGTH: 343
<212> TYPE: PRT
<213> ORGANISM: Artificial Sequence
<220> FEATURE:
<223> OTHER INFORMATION: FGFR4 ECD Ndelta5

<400> SEQUENCE: 46

```
Glu Val Glu Leu Glu Pro Cys Leu Ala Pro Ser Leu Glu Gln Gln Glu
1               5                   10                  15

Gln Glu Leu Thr Val Ala Leu Gly Gln Pro Val Arg Leu Cys Cys Gly
            20                  25                  30

Arg Ala Glu Arg Gly Gly His Trp Tyr Lys Glu Gly Ser Arg Leu Ala
        35                  40                  45

Pro Ala Gly Arg Val Arg Gly Trp Arg Gly Arg Leu Glu Ile Ala Ser
    50                  55                  60

Phe Leu Pro Glu Asp Ala Gly Arg Tyr Leu Cys Leu Ala Arg Gly Ser
65                  70                  75                  80

Met Ile Val Leu Gln Asn Leu Thr Leu Ile Thr Gly Asp Ser Leu Thr
                85                  90                  95

Ser Ser Asn Asp Asp Glu Asp Pro Lys Ser His Arg Asp Pro Ser Asn
            100                 105                 110

Arg His Ser Tyr Pro Gln Gln Ala Pro Tyr Trp Thr His Pro Gln Arg
        115                 120                 125

Met Glu Lys Lys Leu His Ala Val Pro Ala Gly Asn Thr Val Lys Phe
    130                 135                 140

Arg Cys Pro Ala Ala Gly Asn Pro Thr Pro Thr Ile Arg Trp Leu Lys
145                 150                 155                 160

Asp Gly Gln Ala Phe His Gly Glu Asn Arg Ile Gly Gly Ile Arg Leu
                165                 170                 175

Arg His Gln His Trp Ser Leu Val Met Glu Ser Val Val Pro Ser Asp
            180                 185                 190

Arg Gly Thr Tyr Thr Cys Leu Val Glu Asn Ala Val Gly Ser Ile Arg
        195                 200                 205

Tyr Asn Tyr Leu Leu Asp Val Leu Glu Arg Ser Pro His Arg Pro Ile
    210                 215                 220

Leu Gln Ala Gly Leu Pro Ala Asn Thr Thr Ala Val Val Gly Ser Asp
225                 230                 235                 240
```

```
Val Glu Leu Leu Cys Lys Val Tyr Ser Asp Ala Gln Pro His Ile Gln
                245                 250                 255

Trp Leu Lys His Ile Val Ile Asn Gly Ser Ser Phe Gly Ala Asp Gly
            260                 265                 270

Phe Pro Tyr Val Gln Val Leu Lys Thr Ala Asp Ile Asn Ser Ser Glu
        275                 280                 285

Val Glu Val Leu Tyr Leu Arg Asn Val Ser Ala Glu Asp Ala Gly Glu
    290                 295                 300

Tyr Thr Cys Leu Ala Gly Asn Ser Ile Gly Leu Ser Tyr Gln Ser Ala
305                 310                 315                 320

Trp Leu Thr Val Leu Pro Glu Glu Asp Pro Thr Trp Thr Ala Ala Ala
                325                 330                 335

Pro Glu Ala Arg Tyr Thr Asp
                340

<210> SEQ ID NO 47
<211> LENGTH: 341
<212> TYPE: PRT
<213> ORGANISM: Artificial Sequence
<220> FEATURE:
<223> OTHER INFORMATION: FGFR4 ECD Ndelta7

<400> SEQUENCE: 47

Glu Leu Glu Pro Cys Leu Ala Pro Ser Leu Glu Gln Gln Glu Gln Glu
1               5                   10                  15

Leu Thr Val Ala Leu Gly Gln Pro Val Arg Leu Cys Cys Gly Arg Ala
            20                  25                  30

Glu Arg Gly Gly His Trp Tyr Lys Glu Gly Ser Arg Leu Ala Pro Ala
        35                  40                  45

Gly Arg Val Arg Gly Trp Arg Gly Arg Leu Glu Ile Ala Ser Phe Leu
    50                  55                  60

Pro Glu Asp Ala Gly Arg Tyr Leu Cys Leu Ala Arg Gly Ser Met Ile
65                  70                  75                  80

Val Leu Gln Asn Leu Thr Leu Ile Thr Gly Asp Ser Leu Thr Ser Ser
                85                  90                  95

Asn Asp Asp Glu Asp Pro Lys Ser His Arg Asp Pro Ser Asn Arg His
            100                 105                 110

Ser Tyr Pro Gln Gln Ala Pro Tyr Trp Thr His Pro Gln Arg Met Glu
        115                 120                 125

Lys Lys Leu His Ala Val Pro Ala Gly Asn Thr Val Lys Phe Arg Cys
    130                 135                 140

Pro Ala Ala Gly Asn Pro Thr Pro Thr Ile Arg Trp Leu Lys Asp Gly
145                 150                 155                 160

Gln Ala Phe His Gly Glu Asn Arg Ile Gly Ile Arg Leu Arg His
                165                 170                 175

Gln His Trp Ser Leu Val Met Glu Ser Val Val Pro Ser Asp Arg Gly
            180                 185                 190

Thr Tyr Thr Cys Leu Val Glu Asn Ala Val Gly Ser Ile Arg Tyr Asn
        195                 200                 205

Tyr Leu Leu Asp Val Leu Glu Arg Ser Pro His Arg Pro Ile Leu Gln
    210                 215                 220

Ala Gly Leu Pro Ala Asn Thr Thr Ala Val Val Gly Ser Asp Val Glu
225                 230                 235                 240

Leu Leu Cys Lys Val Tyr Ser Asp Ala Gln Pro His Ile Gln Trp Leu
                245                 250                 255

Lys His Ile Val Ile Asn Gly Ser Ser Phe Gly Ala Asp Gly Phe Pro
```

```
                   260                 265                 270
Tyr Val Gln Val Leu Lys Thr Ala Asp Ile Asn Ser Ser Glu Val Glu
                275                 280                 285

Val Leu Tyr Leu Arg Asn Val Ser Ala Glu Asp Ala Gly Glu Tyr Thr
                290                 295                 300

Cys Leu Ala Gly Asn Ser Ile Gly Leu Ser Tyr Gln Ser Ala Trp Leu
305                 310                 315                 320

Thr Val Leu Pro Glu Glu Asp Pro Thr Trp Thr Ala Ala Ala Pro Glu
                325                 330                 335

Ala Arg Tyr Thr Asp
                340

<210> SEQ ID NO 48
<211> LENGTH: 340
<212> TYPE: PRT
<213> ORGANISM: Artificial Sequence
<220> FEATURE:
<223> OTHER INFORMATION: FGFR4 ECD Ndelta8

<400> SEQUENCE: 48

Leu Glu Pro Cys Leu Ala Pro Ser Leu Glu Gln Gln Glu Gln Glu Leu
1               5                   10                  15

Thr Val Ala Leu Gly Gln Pro Val Arg Leu Cys Cys Gly Arg Ala Glu
                20                  25                  30

Arg Gly Gly His Trp Tyr Lys Glu Gly Ser Arg Leu Ala Pro Ala Gly
            35                  40                  45

Arg Val Arg Gly Trp Arg Gly Arg Leu Glu Ile Ala Ser Phe Leu Pro
        50                  55                  60

Glu Asp Ala Gly Arg Tyr Leu Cys Leu Ala Arg Gly Ser Met Ile Val
65                  70                  75                  80

Leu Gln Asn Leu Thr Leu Ile Thr Gly Asp Ser Leu Thr Ser Ser Asn
                85                  90                  95

Asp Asp Glu Asp Pro Lys Ser His Arg Asp Pro Ser Asn Arg His Ser
                100                 105                 110

Tyr Pro Gln Gln Ala Pro Tyr Trp Thr His Pro Gln Arg Met Glu Lys
            115                 120                 125

Lys Leu His Ala Val Pro Ala Gly Asn Thr Val Lys Phe Arg Cys Pro
130                 135                 140

Ala Ala Gly Asn Pro Thr Pro Thr Ile Arg Trp Leu Lys Asp Gly Gln
145                 150                 155                 160

Ala Phe His Gly Glu Asn Arg Ile Gly Gly Ile Arg Leu Arg His Gln
                165                 170                 175

His Trp Ser Leu Val Met Glu Ser Val Val Pro Ser Asp Arg Gly Thr
            180                 185                 190

Tyr Thr Cys Leu Val Glu Asn Ala Val Gly Ser Ile Arg Tyr Asn Tyr
        195                 200                 205

Leu Leu Asp Val Leu Glu Arg Ser Pro His Arg Pro Ile Leu Gln Ala
    210                 215                 220

Gly Leu Pro Ala Asn Thr Thr Ala Val Val Gly Ser Asp Val Glu Leu
225                 230                 235                 240

Leu Cys Lys Val Tyr Ser Asp Ala Gln Pro His Ile Gln Trp Leu Lys
                245                 250                 255

His Ile Val Ile Asn Gly Ser Ser Phe Gly Ala Asp Gly Phe Pro Tyr
            260                 265                 270

Val Gln Val Leu Lys Thr Ala Asp Ile Asn Ser Ser Glu Val Glu Val
        275                 280                 285
```

```
Leu Tyr Leu Arg Asn Val Ser Ala Glu Asp Ala Gly Glu Tyr Thr Cys
    290                 295                 300

Leu Ala Gly Asn Ser Ile Gly Leu Ser Tyr Gln Ser Ala Trp Leu Thr
305                 310                 315                 320

Val Leu Pro Glu Glu Asp Pro Thr Trp Thr Ala Ala Pro Glu Ala
                325                 330                 335

Arg Tyr Thr Asp
            340

<210> SEQ ID NO 49
<211> LENGTH: 323
<212> TYPE: PRT
<213> ORGANISM: Artificial Sequence
<220> FEATURE:
<223> OTHER INFORMATION: FGFR4 ECD Ndelta8 delta17

<400> SEQUENCE: 49

Leu Glu Pro Cys Leu Ala Pro Ser Leu Glu Gln Gln Glu Gln Glu Leu
1               5                   10                  15

Thr Val Ala Leu Gly Gln Pro Val Arg Leu Cys Cys Gly Arg Ala Glu
            20                  25                  30

Arg Gly Gly His Trp Tyr Lys Glu Gly Ser Arg Leu Ala Pro Ala Gly
        35                  40                  45

Arg Val Arg Gly Trp Arg Gly Arg Leu Glu Ile Ala Ser Phe Leu Pro
    50                  55                  60

Glu Asp Ala Gly Arg Tyr Leu Cys Leu Ala Arg Gly Ser Met Ile Val
65                  70                  75                  80

Leu Gln Asn Leu Thr Leu Ile Thr Gly Asp Ser Leu Thr Ser Ser Asn
                85                  90                  95

Asp Asp Glu Asp Pro Lys Ser His Arg Asp Pro Ser Asn Arg His Ser
            100                 105                 110

Tyr Pro Gln Gln Ala Pro Tyr Trp Thr His Pro Gln Arg Met Glu Lys
        115                 120                 125

Lys Leu His Ala Val Pro Ala Gly Asn Thr Val Lys Phe Arg Cys Pro
130                 135                 140

Ala Ala Gly Asn Pro Thr Pro Thr Ile Arg Trp Leu Lys Asp Gly Gln
145                 150                 155                 160

Ala Phe His Gly Glu Asn Arg Ile Gly Gly Ile Arg Leu Arg His Gln
                165                 170                 175

His Trp Ser Leu Val Met Glu Ser Val Val Pro Ser Asp Arg Gly Thr
            180                 185                 190

Tyr Thr Cys Leu Val Glu Asn Ala Val Gly Ser Ile Arg Tyr Asn Tyr
        195                 200                 205

Leu Leu Asp Val Leu Glu Arg Ser Pro His Arg Pro Ile Leu Gln Ala
    210                 215                 220

Gly Leu Pro Ala Asn Thr Thr Ala Val Val Gly Ser Asp Val Glu Leu
225                 230                 235                 240

Leu Cys Lys Val Tyr Ser Asp Ala Gln Pro His Ile Gln Trp Leu Lys
                245                 250                 255

His Ile Val Ile Asn Gly Ser Ser Phe Gly Ala Asp Gly Phe Pro Tyr
            260                 265                 270

Val Gln Val Leu Lys Thr Ala Asp Ile Asn Ser Ser Glu Val Glu Val
        275                 280                 285

Leu Tyr Leu Arg Asn Val Ser Ala Glu Asp Ala Gly Glu Tyr Thr Cys
    290                 295                 300
```

```
Leu Ala Gly Asn Ser Ile Gly Leu Ser Tyr Gln Ser Ala Trp Leu Thr
305                 310                 315                 320

Val Leu Pro

<210> SEQ ID NO 50
<211> LENGTH: 369
<212> TYPE: PRT
<213> ORGANISM: Artificial Sequence
<220> FEATURE:
<223> OTHER INFORMATION: FGFR4 ECD w/ signal peptide

<400> SEQUENCE: 50

Met Arg Leu Leu Leu Ala Leu Leu Gly Ile Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
        50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350
```

```
Glu Glu Asp Pro Thr Trp Thr Ala Ala Ala Pro Glu Ala Arg Tyr Thr
        355                 360                 365

Asp

<210> SEQ ID NO 51
<211> LENGTH: 376
<212> TYPE: PRT
<213> ORGANISM: Artificial Sequence
<220> FEATURE:
<223> OTHER INFORMATION: FGFR1 RM ECD w/ signal peptide

<400> SEQUENCE: 51

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
```

```
                340                 345                 350
Ser Ala Trp Leu Thr Val Leu Glu Ala Leu Glu Glu Arg Pro Ala Val
        355                 360                 365

Met Thr Ser Pro Leu Tyr Leu Glu
    370                 375

<210> SEQ ID NO 52
<211> LENGTH: 566
<212> TYPE: PRT
<213> ORGANISM: Artificial Sequence
<220> FEATURE:
<223> OTHER INFORMATION: FGFR4 ECD delta17 R1 D1-D2 linker chimera + Fc
      (also called FGFR4ECD (ABMut1: delta 17)-Fc and ABMut1)

<400> SEQUENCE: 52

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
    210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
```

```
                 325                 330                 335
Lys Ser Ser Asp Lys Thr His Thr Cys Pro Pro Cys Pro Ala Pro Glu
            340                 345                 350

Leu Leu Gly Gly Pro Ser Val Phe Leu Phe Pro Pro Lys Pro Lys Asp
            355                 360                 365

Thr Leu Met Ile Ser Arg Thr Pro Glu Val Thr Cys Val Val Val Asp
370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
            405                 410                 415

Ser Thr Tyr Arg Val Val Ser Val Leu Thr Val Leu His Gln Asp Trp
            420                 425                 430

Leu Asn Gly Lys Glu Tyr Lys Cys Lys Val Ser Asn Lys Ala Leu Pro
            435                 440                 445

Ala Pro Ile Glu Lys Thr Ile Ser Lys Ala Lys Gly Gln Pro Arg Glu
            450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
            515                 520                 525

Leu Thr Val Asp Lys Ser Arg Trp Gln Gln Gly Asn Val Phe Ser Cys
            530                 535                 540

Ser Val Met His Glu Ala Leu His Asn His Tyr Thr Gln Lys Ser Leu
545                 550                 555                 560

Ser Leu Ser Pro Gly Lys
                565

<210> SEQ ID NO 53
<211> LENGTH: 565
<212> TYPE: PRT
<213> ORGANISM: Artificial Sequence
<220> FEATURE:
<223> OTHER INFORMATION: FGFR4 ECD delta17 R1 exon 4 chimera + Fc (also
      called FGFR4ECD (ABMut2: delta17)-Fc and ABMut2)

<400> SEQUENCE: 53

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Gln Ala Pro
```

```
              115                 120                 125
Tyr Trp Thr His Pro Gln Arg Met Glu Lys Lys Leu His Ala Val Pro
            130                 135                 140
Ala Gly Asn Thr Val Lys Phe Arg Cys Pro Ala Ala Gly Asn Pro Thr
145                 150                 155                 160
Pro Thr Ile Arg Trp Leu Lys Asp Gly Gln Ala Phe His Gly Glu Asn
                165                 170                 175
Arg Ile Gly Gly Ile Arg Leu Arg His Gln His Trp Ser Leu Val Met
                180                 185                 190
Glu Ser Val Val Pro Ser Asp Arg Gly Thr Tyr Thr Cys Leu Val Glu
            195                 200                 205
Asn Ala Val Gly Ser Ile Arg Tyr Asn Tyr Leu Leu Asp Val Leu Glu
            210                 215                 220
Arg Ser Pro His Arg Pro Ile Leu Gln Ala Gly Leu Pro Ala Asn Thr
225                 230                 235                 240
Thr Ala Val Val Gly Ser Asp Val Glu Leu Leu Cys Lys Val Tyr Ser
                245                 250                 255
Asp Ala Gln Pro His Ile Gln Trp Leu Lys His Ile Val Ile Asn Gly
                260                 265                 270
Ser Ser Phe Gly Ala Asp Gly Phe Pro Tyr Val Gln Val Leu Lys Thr
            275                 280                 285
Ala Asp Ile Asn Ser Ser Glu Val Glu Val Leu Tyr Leu Arg Asn Val
            290                 295                 300
Ser Ala Glu Asp Ala Gly Glu Tyr Thr Cys Leu Ala Gly Asn Ser Ile
305                 310                 315                 320
Gly Leu Ser Tyr Gln Ser Ala Trp Leu Thr Val Leu Pro Glu Pro Lys
                325                 330                 335
Ser Ser Asp Lys Thr His Thr Cys Pro Pro Cys Pro Ala Pro Glu Leu
                340                 345                 350
Leu Gly Gly Pro Ser Val Phe Leu Phe Pro Pro Lys Pro Lys Asp Thr
            355                 360                 365
Leu Met Ile Ser Arg Thr Pro Glu Val Thr Cys Val Val Val Asp Val
            370                 375                 380
Ser His Glu Asp Pro Glu Val Lys Phe Asn Trp Tyr Val Asp Gly Val
385                 390                 395                 400
Glu Val His Asn Ala Lys Thr Lys Pro Arg Glu Glu Gln Tyr Asn Ser
                405                 410                 415
Thr Tyr Arg Val Val Ser Val Leu Thr Val Leu His Gln Asp Trp Leu
                420                 425                 430
Asn Gly Lys Glu Tyr Lys Cys Lys Val Ser Asn Lys Ala Leu Pro Ala
            435                 440                 445
Pro Ile Glu Lys Thr Ile Ser Lys Ala Lys Gly Gln Pro Arg Glu Pro
            450                 455                 460
Gln Val Tyr Thr Leu Pro Pro Ser Arg Asp Glu Leu Thr Lys Asn Gln
465                 470                 475                 480
Val Ser Leu Thr Cys Leu Val Lys Gly Phe Tyr Pro Ser Asp Ile Ala
                485                 490                 495
Val Glu Trp Glu Ser Asn Gly Gln Pro Glu Asn Asn Tyr Lys Thr Thr
                500                 505                 510
Pro Pro Val Leu Asp Ser Asp Gly Ser Phe Phe Leu Tyr Ser Lys Leu
            515                 520                 525
Thr Val Asp Lys Ser Arg Trp Gln Gln Gly Asn Val Phe Ser Cys Ser
            530                 535                 540
```

Val Met His Glu Ala Leu His Asn His Tyr Thr Gln Lys Ser Leu Ser
545                 550                 555                 560

Leu Ser Pro Gly Lys
            565

<210> SEQ ID NO 54
<211> LENGTH: 566
<212> TYPE: PRT
<213> ORGANISM: Artificial Sequence
<220> FEATURE:
<223> OTHER INFORMATION: FGFR4 ECD delta17 R1 acid box chimera + Fc

<400> SEQUENCE: 54

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Glu Asp Asp Asp Asp Asp Asp Asp
            100                 105                 110

Ser Ser Ser Glu Asp Pro Ser Asn Arg His Ser Tyr Pro Gln Gln Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
    210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
                325                 330                 335

Lys Ser Ser Asp Lys Thr His Thr Cys Pro Pro Cys Pro Ala Pro Glu

-continued

```
                340                 345                 350
Leu Leu Gly Gly Pro Ser Val Phe Leu Phe Pro Lys Pro Lys Asp
            355                 360                 365
Thr Leu Met Ile Ser Arg Thr Pro Glu Val Thr Cys Val Val Asp
        370                 375                 380
Val Ser His Glu Asp Pro Glu Val Lys Phe Asn Trp Tyr Val Asp Gly
385                 390                 395                 400
Val Glu Val His Asn Ala Lys Thr Lys Pro Arg Glu Glu Gln Tyr Asn
                405                 410                 415
Ser Thr Tyr Arg Val Val Ser Val Leu Thr Val Leu His Gln Asp Trp
            420                 425                 430
Leu Asn Gly Lys Glu Tyr Lys Cys Lys Val Ser Asn Lys Ala Leu Pro
        435                 440                 445
Ala Pro Ile Glu Lys Thr Ile Ser Lys Ala Lys Gly Gln Pro Arg Glu
    450                 455                 460
Pro Gln Val Tyr Thr Leu Pro Pro Ser Arg Asp Glu Leu Thr Lys Asn
465                 470                 475                 480
Gln Val Ser Leu Thr Cys Leu Val Lys Gly Phe Tyr Pro Ser Asp Ile
                485                 490                 495
Ala Val Glu Trp Glu Ser Asn Gly Gln Pro Glu Asn Asn Tyr Lys Thr
            500                 505                 510
Thr Pro Pro Val Leu Asp Ser Asp Gly Ser Phe Phe Leu Tyr Ser Lys
        515                 520                 525
Leu Thr Val Asp Lys Ser Arg Trp Gln Gln Gly Asn Val Phe Ser Cys
    530                 535                 540
Ser Val Met His Glu Ala Leu His Asn His Tyr Thr Gln Lys Ser Leu
545                 550                 555                 560
Ser Leu Ser Pro Gly Lys
                565

<210> SEQ ID NO 55
<211> LENGTH: 495
<212> TYPE: PRT
<213> ORGANISM: Artificial Sequence
<220> FEATURE:
<223> OTHER INFORMATION: FGFR4 ECD 2Ig + D1-D2 linker + GS linker + Fc
      (also called FGFR4ECD(2Ig+Linker)-Fc and R4(2Ig+L))

<400> SEQUENCE: 55

Leu Glu Ala Ser Glu Glu Val Glu Leu Glu Asp Ser Leu Thr Ser
1               5                   10                  15
Asn Asp Asp Glu Asp Pro Lys Ser His Arg Asp Pro Ser Asn Arg His
                20                  25                  30
Ser Tyr Pro Gln Gln Ala Pro Tyr Trp Thr His Pro Gln Arg Met Glu
            35                  40                  45
Lys Lys Leu His Ala Val Pro Ala Gly Asn Thr Val Lys Phe Arg Cys
        50                  55                  60
Pro Ala Ala Gly Asn Pro Thr Pro Thr Ile Arg Trp Leu Lys Asp Gly
65                  70                  75                  80
Gln Ala Phe His Gly Glu Asn Arg Ile Gly Gly Ile Arg Leu Arg His
                85                  90                  95
Gln His Trp Ser Leu Val Met Glu Ser Val Val Pro Ser Asp Arg Gly
            100                 105                 110
Thr Tyr Thr Cys Leu Val Glu Asn Ala Val Gly Ser Ile Arg Tyr Asn
        115                 120                 125
Tyr Leu Leu Asp Val Leu Glu Arg Ser Pro His Arg Pro Ile Leu Gln
```

```
                    130                 135                 140
Ala Gly Leu Pro Ala Asn Thr Thr Ala Val Gly Ser Asp Val Glu
145                 150                 155                 160

Leu Leu Cys Lys Val Tyr Ser Asp Ala Gln Pro His Ile Gln Trp Leu
                165                 170                 175

Lys His Ile Val Ile Asn Gly Ser Ser Phe Gly Ala Asp Gly Phe Pro
                180                 185                 190

Tyr Val Gln Val Leu Lys Thr Ala Asp Ile Asn Ser Ser Glu Val Glu
                195                 200                 205

Val Leu Tyr Leu Arg Asn Val Ser Ala Glu Asp Ala Gly Glu Tyr Thr
210                 215                 220

Cys Leu Ala Gly Asn Ser Ile Gly Leu Ser Tyr Gln Ser Ala Trp Leu
225                 230                 235                 240

Thr Val Leu Pro Glu Glu Asp Pro Thr Trp Thr Ala Ala Pro Glu
                245                 250                 255

Ala Arg Tyr Thr Asp Gly Ser Glu Pro Lys Ser Ser Asp Lys Thr His
                260                 265                 270

Thr Cys Pro Pro Cys Pro Ala Pro Glu Leu Leu Gly Gly Pro Ser Val
                275                 280                 285

Phe Leu Phe Pro Pro Lys Pro Lys Asp Thr Leu Met Ile Ser Arg Thr
290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
                340                 345                 350

Val Leu Thr Val Leu His Gln Asp Trp Leu Asn Gly Lys Glu Tyr Lys
                355                 360                 365

Cys Lys Val Ser Asn Lys Ala Leu Pro Ala Pro Ile Glu Lys Thr Ile
370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
                420                 425                 430

Gly Gln Pro Glu Asn Asn Tyr Lys Thr Thr Pro Pro Val Leu Asp Ser
                435                 440                 445

Asp Gly Ser Phe Phe Leu Tyr Ser Lys Leu Thr Val Asp Lys Ser Arg
450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys
                485                 490                 495

<210> SEQ ID NO 56
<211> LENGTH: 468
<212> TYPE: PRT
<213> ORGANISM: Artificial Sequence
<220> FEATURE:
<223> OTHER INFORMATION: FGFR4 ECD 2Ig - D1-D2 linker + GS linker + Fc
      (also called FGFR4ECD(2Ig-Linker)-Fc and R4(2Ig-L))

<400> SEQUENCE: 56

Leu Glu Ala Ser Glu Glu Val Glu Leu Glu Ala Pro Tyr Trp Thr His
```

-continued

```
    1               5                  10                 15
Pro Gln Arg Met Glu Lys Lys Leu His Ala Val Pro Ala Gly Asn Thr
                20                 25                 30

Val Lys Phe Arg Cys Pro Ala Ala Gly Asn Pro Thr Pro Thr Ile Arg
                35                 40                 45

Trp Leu Lys Asp Gly Gln Ala Phe His Gly Glu Asn Arg Ile Gly Gly
                50                 55                 60

Ile Arg Leu Arg His Gln His Trp Ser Leu Val Met Glu Ser Val Val
 65                 70                 75                 80

Pro Ser Asp Arg Gly Thr Tyr Thr Cys Leu Val Glu Asn Ala Val Gly
                85                 90                 95

Ser Ile Arg Tyr Asn Tyr Leu Leu Asp Val Leu Glu Arg Ser Pro His
                100                105                110

Arg Pro Ile Leu Gln Ala Gly Leu Pro Ala Asn Thr Ala Val Val
                115                120                125

Gly Ser Asp Val Glu Leu Leu Cys Lys Val Tyr Ser Asp Ala Gln Pro
                130                135                140

His Ile Gln Trp Leu Lys His Ile Val Ile Asn Gly Ser Ser Phe Gly
145                150                155                160

Ala Asp Gly Phe Pro Tyr Val Gln Val Leu Lys Thr Ala Asp Ile Asn
                165                170                175

Ser Ser Glu Val Glu Val Leu Tyr Leu Arg Asn Val Ser Ala Glu Asp
                180                185                190

Ala Gly Glu Tyr Thr Cys Leu Ala Gly Asn Ser Ile Gly Leu Ser Tyr
                195                200                205

Gln Ser Ala Trp Leu Thr Val Leu Pro Glu Glu Asp Pro Thr Trp Thr
                210                215                220

Ala Ala Ala Pro Glu Ala Arg Tyr Thr Asp Gly Ser Glu Pro Lys Ser
225                230                235                240

Ser Asp Lys Thr His Thr Cys Pro Pro Cys Pro Ala Pro Glu Leu Leu
                245                250                255

Gly Gly Pro Ser Val Phe Leu Phe Pro Pro Lys Pro Lys Asp Thr Leu
                260                265                270

Met Ile Ser Arg Thr Pro Glu Val Thr Cys Val Val Val Asp Val Ser
                275                280                285

His Glu Asp Pro Glu Val Lys Phe Asn Trp Tyr Val Asp Gly Val Glu
                290                295                300

Val His Asn Ala Lys Thr Lys Pro Arg Glu Glu Gln Tyr Asn Ser Thr
305                310                315                320

Tyr Arg Val Val Ser Val Leu Thr Val Leu His Gln Asp Trp Leu Asn
                325                330                335

Gly Lys Glu Tyr Lys Cys Lys Val Ser Asn Lys Ala Leu Pro Ala Pro
                340                345                350

Ile Glu Lys Thr Ile Ser Lys Ala Lys Gly Gln Pro Arg Glu Pro Gln
                355                360                365

Val Tyr Thr Leu Pro Pro Ser Arg Asp Glu Leu Thr Lys Asn Gln Val
                370                375                380

Ser Leu Thr Cys Leu Val Lys Gly Phe Tyr Pro Ser Asp Ile Ala Val
385                390                395                400

Glu Trp Glu Ser Asn Gly Gln Pro Glu Asn Asn Tyr Lys Thr Thr Pro
                405                410                415

Pro Val Leu Asp Ser Asp Gly Ser Phe Phe Leu Tyr Ser Lys Leu Thr
                420                425                430
```

```
Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
450                 455                 460

Ser Pro Gly Lys
465

<210> SEQ ID NO 57
<211> LENGTH: 571
<212> TYPE: PRT
<213> ORGANISM: Artificial Sequence
<220> FEATURE:
<223> OTHER INFORMATION: FGFR1 ECD delta14 + Fc (also called
      FGFR1ECD(delta14)-Fc and R1Mut4)

<400> SEQUENCE: 57

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
    50                  55                  60

Val Glu Val Gln Asp Ser Val Pro Ala Asp Ser Gly Leu Tyr Ala Cys
65                  70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
    130                 135                 140

Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
            180                 185                 190

Ile Met Asp Ser Val Val Pro Ser Asp Lys Gly Asn Tyr Thr Cys Ile
        195                 200                 205

Val Glu Asn Glu Tyr Gly Ser Ile Asn His Thr Tyr Gln Leu Asp Val
    210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
            260                 265                 270

Asn Gly Ser Lys Ile Gly Pro Asp Asn Leu Pro Tyr Val Gln Ile Leu
        275                 280                 285

Lys Thr Ala Gly Val Asn Thr Thr Asp Lys Glu Met Glu Val Leu His
    290                 295                 300

Leu Arg Asn Val Ser Phe Glu Asp Ala Gly Glu Tyr Thr Cys Leu Ala
305                 310                 315                 320
```

```
Gly Asn Ser Ile Gly Leu Ser His His Ser Ala Trp Leu Thr Val Leu
            325                 330                 335

Glu Ala Leu Glu Pro Lys Ser Ser Asp Lys Thr His Thr Cys Pro Pro
            340                 345                 350

Cys Pro Ala Pro Glu Leu Leu Gly Gly Pro Ser Val Phe Leu Phe Pro
            355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
            565                 570

<210> SEQ ID NO 58
<211> LENGTH: 261
<212> TYPE: PRT
<213> ORGANISM: Artificial Sequence
<220> FEATURE:
<223> OTHER INFORMATION: FGFR4 ECD 2Ig + D1-D2 linker

<400> SEQUENCE: 58

Leu Glu Ala Ser Glu Glu Val Glu Leu Glu Asp Ser Leu Thr Ser Ser
1               5                   10                  15

Asn Asp Asp Glu Asp Pro Lys Ser His Arg Asp Pro Ser Asn Arg His
            20                  25                  30

Ser Tyr Pro Gln Gln Ala Pro Tyr Trp Thr His Pro Gln Arg Met Glu
        35                  40                  45

Lys Lys Leu His Ala Val Pro Ala Gly Asn Thr Val Lys Phe Arg Cys
    50                  55                  60

Pro Ala Ala Gly Asn Pro Thr Pro Thr Ile Arg Trp Leu Lys Asp Gly
65                  70                  75                  80

Gln Ala Phe His Gly Glu Asn Arg Ile Gly Gly Ile Arg Leu Arg His
                85                  90                  95

Gln His Trp Ser Leu Val Met Glu Ser Val Val Pro Ser Asp Arg Gly
            100                 105                 110

Thr Tyr Thr Cys Leu Val Glu Asn Ala Val Gly Ser Ile Arg Tyr Asn
```

```
                115                 120                 125
Tyr Leu Leu Asp Val Leu Glu Arg Ser Pro His Arg Pro Ile Leu Gln
        130                 135                 140
Ala Gly Leu Pro Ala Asn Thr Thr Ala Val Gly Ser Asp Val Glu
145                 150                 155                 160
Leu Leu Cys Lys Val Tyr Ser Asp Ala Gln Pro His Ile Gln Trp Leu
                165                 170                 175
Lys His Ile Val Ile Asn Gly Ser Ser Phe Gly Ala Asp Gly Phe Pro
                180                 185                 190
Tyr Val Gln Val Leu Lys Thr Ala Asp Ile Asn Ser Ser Glu Val Glu
                195                 200                 205
Val Leu Tyr Leu Arg Asn Val Ser Ala Glu Asp Ala Gly Glu Tyr Thr
                210                 215                 220
Cys Leu Ala Gly Asn Ser Ile Gly Leu Ser Tyr Gln Ser Ala Trp Leu
225                 230                 235                 240
Thr Val Leu Pro Glu Glu Asp Pro Thr Trp Thr Ala Ala Ala Pro Glu
                245                 250                 255
Ala Arg Tyr Thr Asp
            260

<210> SEQ ID NO 59
<211> LENGTH: 234
<212> TYPE: PRT
<213> ORGANISM: Artificial Sequence
<220> FEATURE:
<223> OTHER INFORMATION: FGFR4 ECD 2Ig - D1-D2 linker

<400> SEQUENCE: 59

Leu Glu Ala Ser Glu Glu Val Glu Leu Glu Ala Pro Tyr Trp Thr His
1               5                   10                  15
Pro Gln Arg Met Glu Lys Lys Leu His Ala Val Pro Ala Gly Asn Thr
                20                  25                  30
Val Lys Phe Arg Cys Pro Ala Ala Gly Asn Pro Thr Pro Thr Ile Arg
            35                  40                  45
Trp Leu Lys Asp Gly Gln Ala Phe His Gly Glu Asn Arg Ile Gly Gly
        50                  55                  60
Ile Arg Leu Arg His Gln His Trp Ser Leu Val Met Glu Ser Val Val
65                  70                  75                  80
Pro Ser Asp Arg Gly Thr Tyr Thr Cys Leu Val Glu Asn Ala Val Gly
                85                  90                  95
Ser Ile Arg Tyr Asn Tyr Leu Leu Asp Val Leu Glu Arg Ser Pro His
                100                 105                 110
Arg Pro Ile Leu Gln Ala Gly Leu Pro Ala Asn Thr Thr Ala Val Val
                115                 120                 125
Gly Ser Asp Val Glu Leu Leu Cys Lys Val Tyr Ser Asp Ala Gln Pro
        130                 135                 140
His Ile Gln Trp Leu Lys His Ile Val Ile Asn Gly Ser Ser Phe Gly
145                 150                 155                 160
Ala Asp Gly Phe Pro Tyr Val Gln Val Leu Lys Thr Ala Asp Ile Asn
                165                 170                 175
Ser Ser Glu Val Glu Val Leu Tyr Leu Arg Asn Val Ser Ala Glu Asp
                180                 185                 190
Ala Gly Glu Tyr Thr Cys Leu Ala Gly Asn Ser Ile Gly Leu Ser Tyr
                195                 200                 205
Gln Ser Ala Trp Leu Thr Val Leu Pro Glu Glu Asp Pro Thr Trp Thr
        210                 215                 220
```

```
Ala Ala Ala Pro Glu Ala Arg Tyr Thr Asp
        225                 230

<210> SEQ ID NO 60
<211> LENGTH: 15
<212> TYPE: PRT
<213> ORGANISM: Artificial Sequence
<220> FEATURE:
<223> OTHER INFORMATION: FGFR4 long acid box

<400> SEQUENCE: 60

Asn Asp Asp Glu Asp Pro Lys Ser His Arg Asp Pro Ser Asn Arg
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: FGFR4 P115L long acid box

<400> SEQUENCE: 61

Asn Asp Asp Glu Asp Pro Lys Ser His Arg Asp Leu Ser Asn Arg
1               5                   10                  15

<210> SEQ ID NO 62
<211> LENGTH: 17
<212> TYPE: PRT
<213> ORGANISM: Artificial Sequence
<220> FEATURE:
<223> OTHER INFORMATION: FGFR1 long acid box

<400> SEQUENCE: 62

Glu Asp Asp Asp Asp Asp Asp Asp Ser Ser Ser Glu Glu Lys Glu Thr
1               5                   10                  15

Asp

<210> SEQ ID NO 63
<211> LENGTH: 4
<212> TYPE: PRT
<213> ORGANISM: Artificial Sequence
<220> FEATURE:
<223> OTHER INFORMATION: FGFR4 short acid box

<400> SEQUENCE: 63

Asp Asp Glu Asp
1

<210> SEQ ID NO 64
<211> LENGTH: 333
<212> TYPE: PRT
<213> ORGANISM: Artificial Sequence
<220> FEATURE:
<223> OTHER INFORMATION: FGFR4 ECD delta17 R1 long acid box chimera

<400> SEQUENCE: 64

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60
```

```
Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Glu Asp Asp Asp Asp Asp Asp Asp Ser
            100                 105                 110

Ser Ser Glu Glu Lys Glu Thr Asp His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
    290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
                325                 330

<210> SEQ ID NO 65
<211> LENGTH: 335
<212> TYPE: PRT
<213> ORGANISM: Artificial Sequence
<220> FEATURE:
<223> OTHER INFORMATION: FGFR4 ECD delta17 R1 short acid box chimera

<400> SEQUENCE: 65

Leu Glu Ala Ser Glu Glu Val Glu Leu Glu Pro Cys Leu Ala Pro Ser
 1               5                  10                  15

Leu Glu Gln Gln Glu Gln Glu Leu Thr Val Ala Leu Gly Gln Pro Val
                 20                  25                  30

Arg Leu Cys Cys Gly Arg Ala Glu Arg Gly Gly His Trp Tyr Lys Glu
             35                  40                  45

Gly Ser Arg Leu Ala Pro Ala Gly Arg Val Arg Gly Trp Arg Gly Arg
         50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                 85                  90                  95

Gly Asp Ser Leu Thr Ser Ser Asn Glu Asp Asp Asp Asp Asp Asp Asp
```

```
                100                 105                 110
Pro Lys Ser His Arg Asp Pro Ser Asn Arg His Ser Tyr Pro Gln Gln
            115                 120                 125

Ala Pro Tyr Trp Thr His Pro Gln Arg Met Glu Lys Lys Leu His Ala
            130                 135                 140

Val Pro Ala Gly Asn Thr Val Lys Phe Arg Cys Pro Ala Ala Gly Asn
145                 150                 155                 160

Pro Thr Pro Thr Ile Arg Trp Leu Lys Asp Gly Gln Ala Phe His Gly
            165                 170                 175

Glu Asn Arg Ile Gly Gly Ile Arg Leu Arg His Gln His Trp Ser Leu
            180                 185                 190

Val Met Glu Ser Val Val Pro Ser Asp Arg Gly Thr Tyr Thr Cys Leu
            195                 200                 205

Val Glu Asn Ala Val Gly Ser Ile Arg Tyr Asn Tyr Leu Leu Asp Val
            210                 215                 220

Leu Glu Arg Ser Pro His Arg Pro Ile Leu Gln Ala Gly Leu Pro Ala
225                 230                 235                 240

Asn Thr Thr Ala Val Val Gly Ser Asp Val Glu Leu Leu Cys Lys Val
            245                 250                 255

Tyr Ser Asp Ala Gln Pro His Ile Gln Trp Leu Lys His Ile Val Ile
            260                 265                 270

Asn Gly Ser Ser Phe Gly Ala Asp Gly Phe Pro Tyr Val Gln Val Leu
            275                 280                 285

Lys Thr Ala Asp Ile Asn Ser Ser Glu Val Glu Val Leu Tyr Leu Arg
            290                 295                 300

Asn Val Ser Ala Glu Asp Ala Gly Glu Tyr Thr Cys Leu Ala Gly Asn
305                 310                 315                 320

Ser Ile Gly Leu Ser Tyr Gln Ser Ala Trp Leu Thr Val Leu Pro
            325                 330                 335

<210> SEQ ID NO 66
<211> LENGTH: 331
<212> TYPE: PRT
<213> ORGANISM: Artificial Sequence
<220> FEATURE:
<223> OTHER INFORMATION: FGFR4 ECD delta17 N104D

<400> SEQUENCE: 66

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
            85                  90                  95

Gly Asp Ser Leu Thr Ser Ser Asp Asp Glu Asp Pro Lys Ser His
            100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
            130                 135                 140
```

```
Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 67
<211> LENGTH: 331
<212> TYPE: PRT
<213> ORGANISM: Artificial Sequence
<220> FEATURE:
<223> OTHER INFORMATION: FGFR4 ECD delta17 P109D

<400> SEQUENCE: 67

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Asp Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175
```

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
            210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 68
<211> LENGTH: 331
<212> TYPE: PRT
<213> ORGANISM: Artificial Sequence
<220> FEATURE:
<223> OTHER INFORMATION: FGFR4 ECD delta17 R113E

<400> SEQUENCE: 68

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Glu Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
        130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser

```
                    210                 215                 220
Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                    245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330
```

<210> SEQ ID NO 69
<211> LENGTH: 331
<212> TYPE: PRT
<213> ORGANISM: Artificial Sequence
<220> FEATURE:
<223> OTHER INFORMATION: FGFR4 ECD delta17 S116E

<400> SEQUENCE: 69

```
Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
                100                 105                 110

Arg Asp Pro Glu Asn Arg His Ser Tyr Pro Gln Gln Ala Pro Tyr Trp
            115                 120                 125

Thr His Pro Gln Arg Met Glu Lys Lys Leu His Ala Val Pro Ala Gly
130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255
```

```
Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 70
<211> LENGTH: 332
<212> TYPE: PRT
<213> ORGANISM: Artificial Sequence
<220> FEATURE:
<223> OTHER INFORMATION: FGFR4 ECD delta17 R4(104-114):R1(106-117)

<400> SEQUENCE: 70

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Asp Ser Ser Ser
            100                 105                 110

Ser Glu Glu Pro Ser Asn Arg His Ser Tyr Pro Gln Gln Ala Pro Tyr
        115                 120                 125

Trp Thr His Pro Gln Arg Met Glu Lys Lys Leu His Ala Val Pro Ala
    130                 135                 140

Gly Asn Thr Val Lys Phe Arg Cys Pro Ala Ala Gly Asn Pro Thr Pro
145                 150                 155                 160

Thr Ile Arg Trp Leu Lys Asp Gly Gln Ala Phe His Gly Glu Asn Arg
                165                 170                 175

Ile Gly Gly Ile Arg Leu Arg His Gln His Trp Ser Leu Val Met Glu
            180                 185                 190

Ser Val Val Pro Ser Asp Arg Gly Thr Tyr Thr Cys Leu Val Glu Asn
        195                 200                 205

Ala Val Gly Ser Ile Arg Tyr Asn Tyr Leu Leu Asp Val Leu Glu Arg
    210                 215                 220

Ser Pro His Arg Pro Ile Leu Gln Ala Gly Leu Pro Ala Asn Thr Thr
225                 230                 235                 240

Ala Val Val Gly Ser Asp Val Glu Leu Leu Cys Lys Val Tyr Ser Asp
                245                 250                 255

Ala Gln Pro His Ile Gln Trp Leu Lys His Ile Val Ile Asn Gly Ser
            260                 265                 270

Ser Phe Gly Ala Asp Gly Phe Pro Tyr Val Gln Val Leu Lys Thr Ala
        275                 280                 285
```

```
Asp Ile Asn Ser Ser Glu Val Glu Val Leu Tyr Leu Arg Asn Val Ser
        290                 295                 300

Ala Glu Asp Ala Gly Glu Tyr Thr Cys Leu Ala Gly Asn Ser Ile Gly
305                 310                 315                 320

Leu Ser Tyr Gln Ser Ala Trp Leu Thr Val Leu Pro
                325                 330

<210> SEQ ID NO 71
<211> LENGTH: 331
<212> TYPE: PRT
<213> ORGANISM: Artificial Sequence
<220> FEATURE:
<223> OTHER INFORMATION: FGFR4 ECD delta17 R4(104-114):R1(107-117)

<400> SEQUENCE: 71

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Ser Ser Ser Ser
            100                 105                 110

Glu Glu Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330
```

325                 330

<210> SEQ ID NO 72
<211> LENGTH: 333
<212> TYPE: PRT
<213> ORGANISM: Artificial Sequence
<220> FEATURE:
<223> OTHER INFORMATION: FGFR4 ECD delta17 R4(104-110):R1 (105-113)

<400> SEQUENCE: 72

Leu Glu Ala Ser Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Asp Ser
            100                 105                 110

Ser His Arg Asp Pro Ser Asn Arg His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
    290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
                325                 330

<210> SEQ ID NO 73
<211> LENGTH: 331
<212> TYPE: PRT
<213> ORGANISM: Artificial Sequence
<220> FEATURE:
<223> OTHER INFORMATION: FGFR4 ECD delta17 R4(113-116):R1(116-119)

<400> SEQUENCE: 73

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Glu Glu Lys Glu Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 74
<211> LENGTH: 331
<212> TYPE: PRT
<213> ORGANISM: Artificial Sequence
<220> FEATURE:
<223> OTHER INFORMATION: FGFR4 ECD delta17 R4(109-113):R1(112-116)

<400> SEQUENCE: 74

Leu Glu Ala Ser Glu Glu Val Glu Leu Glu Pro Cys Leu Ala Pro Ser
1               5                   10                  15

```
Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
 50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Ser Ser Ser
                100                 105                 110

Glu Asp Pro Ser Asn Arg His Ser Tyr Pro Gln Ala Pro Tyr Trp
                115                 120                 125

Thr His Pro Gln Arg Met Glu Lys Lys Leu His Ala Val Pro Ala Gly
            130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
                290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro
                325                 330

<210> SEQ ID NO 75
<211> LENGTH: 334
<212> TYPE: PRT
<213> ORGANISM: Artificial Sequence
<220> FEATURE:
<223> OTHER INFORMATION: FGFR4 ECD delta17 R1 D1-D2 linker chimera
      (N91A)

<400> SEQUENCE: 75

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45
```

```
Gly Ser Arg Leu Ala Pro Ala Gly Arg Val Arg Gly Trp Arg Gly Arg
         50                  55                  60

Leu Glu Ile Ala Ser Phe Leu Pro Glu Asp Ala Gly Arg Tyr Leu Cys
 65                  70                  75                  80

Leu Ala Arg Gly Ser Met Ile Val Leu Gln Ala Leu Thr Leu Ile Thr
                 85                  90                  95

Gly Asp Ala Leu Pro Ser Ser Glu Asp Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Asn Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro
                325                 330

<210> SEQ ID NO 76
<211> LENGTH: 334
<212> TYPE: PRT
<213> ORGANISM: Artificial Sequence
<220> FEATURE:
<223> OTHER INFORMATION: FGFR4 ECD delta17 R1 D1-D2 linker chimera
      (N159A)

<400> SEQUENCE: 76

Leu Glu Ala Ser Glu Glu Val Glu Leu Glu Pro Cys Leu Ala Pro Ser
 1               5                  10                  15

Leu Glu Gln Gln Glu Gln Glu Leu Thr Val Ala Leu Gly Gln Pro Val
             20                  25                  30

Arg Leu Cys Cys Gly Arg Ala Glu Arg Gly Gly His Trp Tyr Lys Glu
         35                  40                  45

Gly Ser Arg Leu Ala Pro Ala Gly Arg Val Arg Gly Trp Arg Gly Arg
     50                  55                  60

Leu Glu Ile Ala Ser Phe Leu Pro Glu Asp Ala Gly Arg Tyr Leu Cys
 65                  70                  75                  80
```

```
Leu Ala Arg Gly Ser Met Ile Val Leu Gln Asn Leu Thr Leu Ile Thr
                85                  90                  95
Gly Asp Ala Leu Pro Ser Ser Glu Asp Asp Asp Asp Asp Asp Asp Ser
            100                 105                 110
Ser Ser Glu Glu Lys Glu Thr Asp Asn Thr Lys Pro Asn Pro Val Ala
        115                 120                 125
Pro Tyr Trp Thr His Pro Gln Arg Met Glu Lys Lys Leu His Ala Val
    130                 135                 140
Pro Ala Gly Asn Thr Val Lys Phe Arg Cys Pro Ala Ala Gly Ala Pro
145                 150                 155                 160
Thr Pro Thr Ile Arg Trp Leu Lys Asp Gly Gln Ala Phe His Gly Glu
                165                 170                 175
Asn Arg Ile Gly Gly Ile Arg Leu Arg His Gln His Trp Ser Leu Val
            180                 185                 190
Met Glu Ser Val Val Pro Ser Asp Arg Gly Thr Tyr Thr Cys Leu Val
        195                 200                 205
Glu Asn Ala Val Gly Ser Ile Arg Tyr Asn Tyr Leu Leu Asp Val Leu
    210                 215                 220
Glu Arg Ser Pro His Arg Pro Ile Leu Gln Ala Gly Leu Pro Ala Asn
225                 230                 235                 240
Thr Thr Ala Val Val Gly Ser Asp Val Glu Leu Leu Cys Lys Val Tyr
                245                 250                 255
Ser Asp Ala Gln Pro His Ile Gln Trp Leu Lys His Ile Val Ile Asn
            260                 265                 270
Gly Ser Ser Phe Gly Ala Asp Gly Phe Pro Tyr Val Gln Val Leu Lys
        275                 280                 285
Thr Ala Asp Ile Asn Ser Ser Glu Val Glu Val Leu Tyr Leu Arg Asn
    290                 295                 300
Val Ser Ala Glu Asp Ala Gly Glu Tyr Thr Cys Leu Ala Gly Asn Ser
305                 310                 315                 320
Ile Gly Leu Ser Tyr Gln Ser Ala Trp Leu Thr Val Leu Pro
                325                 330
```

<210> SEQ ID NO 77
<211> LENGTH: 565
<212> TYPE: PRT
<213> ORGANISM: Artificial Sequence
<220> FEATURE:
<223> OTHER INFORMATION: FGFR4 ECD delta17 R1 long acid box chimera-Fc

<400> SEQUENCE: 77

```
Leu Glu Ala Ser Glu Glu Val Glu Leu Glu Pro Cys Leu Ala Pro Ser
1               5                   10                  15
Leu Glu Gln Gln Glu Gln Glu Leu Thr Val Ala Leu Gly Gln Pro Val
            20                  25                  30
Arg Leu Cys Cys Gly Arg Ala Glu Arg Gly Gly His Trp Tyr Lys Glu
        35                  40                  45
Gly Ser Arg Leu Ala Pro Ala Gly Arg Val Arg Gly Trp Arg Gly Arg
    50                  55                  60
Leu Glu Ile Ala Ser Phe Leu Pro Glu Asp Ala Gly Arg Tyr Leu Cys
65                  70                  75                  80
Leu Ala Arg Gly Ser Met Ile Val Leu Gln Asn Leu Thr Leu Ile Thr
                85                  90                  95
Gly Asp Ser Leu Thr Ser Ser Glu Asp Asp Asp Asp Asp Asp Asp Ser
            100                 105                 110
```

```
Ser Ser Glu Glu Lys Glu Thr Asp His Ser Tyr Pro Gln Gln Ala Pro
        115                 120                 125

Tyr Trp Thr His Pro Gln Arg Met Glu Lys Lys Leu His Ala Val Pro
        130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
                180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
                260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
        290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro Glu Pro Lys
                325                 330                 335

Ser Ser Asp Lys Thr His Thr Cys Pro Pro Cys Pro Ala Pro Glu Leu
                340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
        370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415

Thr Tyr Arg Val Val Ser Val Leu Thr Val Leu His Gln Asp Trp Leu
                420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
                500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
        530                 535                 540
```

```
Val Met His Glu Ala Leu His Asn His Tyr Thr Gln Lys Ser Leu Ser
545                 550                 555                 560

Leu Ser Pro Gly Lys
                565

<210> SEQ ID NO 78
<211> LENGTH: 335
<212> TYPE: PRT
<213> ORGANISM: Artificial Sequence
<220> FEATURE:
<223> OTHER INFORMATION: FGFR4 ECD delta17 R1 short acid box chimera-Fc

<400> SEQUENCE: 78

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
        20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Glu Asp Asp Asp Asp Asp Asp
            100                 105                 110

Pro Lys Ser His Arg Asp Pro Ser Asn Arg His Ser Tyr Pro Gln Gln
        115                 120                 125

Ala Pro Tyr Trp Thr His Pro Gln Arg Met Glu Lys Lys Leu His Ala
    130                 135                 140

Val Pro Ala Gly Asn Thr Val Lys Phe Arg Cys Pro Ala Ala Gly Asn
145                 150                 155                 160

Pro Thr Pro Thr Ile Arg Trp Leu Lys Asp Gly Gln Ala Phe His Gly
                165                 170                 175

Glu Asn Arg Ile Gly Gly Ile Arg Leu Arg His Gln His Trp Ser Leu
            180                 185                 190

Val Met Glu Ser Val Val Pro Ser Asp Arg Gly Thr Tyr Thr Cys Leu
        195                 200                 205

Val Glu Asn Ala Val Gly Ser Ile Arg Tyr Asn Tyr Leu Leu Asp Val
    210                 215                 220

Leu Glu Arg Ser Pro His Arg Pro Ile Leu Gln Ala Gly Leu Pro Ala
225                 230                 235                 240

Asn Thr Thr Ala Val Val Gly Ser Asp Val Glu Leu Leu Cys Lys Val
                245                 250                 255

Tyr Ser Asp Ala Gln Pro His Ile Gln Trp Leu Lys His Ile Val Ile
            260                 265                 270

Asn Gly Ser Ser Phe Gly Ala Asp Gly Phe Pro Tyr Val Gln Val Leu
        275                 280                 285

Lys Thr Ala Asp Ile Asn Ser Ser Glu Val Glu Val Leu Tyr Leu Arg
    290                 295                 300

Asn Val Ser Ala Glu Asp Ala Gly Glu Tyr Thr Cys Leu Ala Gly Asn
305                 310                 315                 320

Ser Ile Gly Leu Ser Tyr Gln Ser Ala Trp Leu Thr Val Leu Pro
                325                 330                 335
```

<210> SEQ ID NO 79
<211> LENGTH: 563
<212> TYPE: PRT
<213> ORGANISM: Artificial Sequence
<220> FEATURE:
<223> OTHER INFORMATION: FGFR4 ECD delta17 N104D + Fc (also called
      FGFR4ECD(R4Mut4(N104D): delta17)-Fc and R4Mut4(N104D))

<400> SEQUENCE: 79

```
Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Glu Asp Pro Lys Ser His
            100                 105                 110

Arg Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
    210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
    290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
        355                 360                 365
```

```
Ile Ser Arg Thr Pro Glu Val Thr Cys Val Val Asp Val Ser His
        370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
            405                 410                 415

Arg Val Val Ser Val Leu Thr Val Leu His Gln Asp Trp Leu Asn Gly
        420                 425                 430

Lys Glu Tyr Lys Cys Lys Val Ser Asn Lys Ala Leu Pro Ala Pro Ile
            435                 440                 445

Glu Lys Thr Ile Ser Lys Ala Lys Gly Gln Pro Arg Glu Pro Gln Val
450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
            485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
530                 535                 540

His Glu Ala Leu His Asn His Tyr Thr Gln Lys Ser Leu Ser Leu Ser
545                 550                 555                 560

Pro Gly Lys

<210> SEQ ID NO 80
<211> LENGTH: 563
<212> TYPE: PRT
<213> ORGANISM: Artificial Sequence
<220> FEATURE:
<223> OTHER INFORMATION: FGFR4 ECD delta17 P109D + Fc (also called
      FGFR4ECD(R4Mut4(P109D): delta17)-Fc and R4Mut4(P109D))

<400> SEQUENCE: 80

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Lys Ser His
            100                 105                 110

Arg Asp Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
```

```
                            165                 170                 175
Gly Gly Ile Arg Leu Arg His Gln His Trp Ser Leu Val Met Glu Ser
                180                 185                 190

Val Val Pro Ser Asp Arg Gly Thr Tyr Thr Cys Leu Val Glu Asn Ala
                195                 200                 205

Val Gly Ser Ile Arg Tyr Asn Tyr Leu Leu Asp Val Leu Glu Arg Ser
                210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
                275                 280                 285

Ile Asn Ser Ser Glu Val Glu Val Leu Tyr Leu Arg Asn Val Ser Ala
                290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
                340                 345                 350

Gly Pro Ser Val Phe Leu Phe Pro Pro Lys Pro Lys Asp Thr Leu Met
                355                 360                 365

Ile Ser Arg Thr Pro Glu Val Thr Cys Val Val Val Asp Val Ser His
                370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
                420                 425                 430

Lys Glu Tyr Lys Cys Lys Val Ser Asn Lys Ala Leu Pro Ala Pro Ile
                435                 440                 445

Glu Lys Thr Ile Ser Lys Ala Lys Gly Gln Pro Arg Glu Pro Gln Val
                450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
                500                 505                 510

Val Leu Asp Ser Asp Gly Ser Phe Phe Leu Tyr Ser Lys Leu Thr Val
                515                 520                 525

Asp Lys Ser Arg Trp Gln Gln Gly Asn Val Phe Ser Cys Ser Val Met
                530                 535                 540

His Glu Ala Leu His Asn His Tyr Thr Gln Lys Ser Leu Ser Leu Ser
545                 550                 555                 560

Pro Gly Lys

<210> SEQ ID NO 81
<211> LENGTH: 563
<212> TYPE: PRT
```

<213> ORGANISM: Artificial Sequence
<220> FEATURE:
<223> OTHER INFORMATION: FGFR4 ECD delta17 R113E + Fc (also called
      FGFR4ECD(R4Mut4(R113E): delta17)-Fc and R4Mut4(R113E))

<400> SEQUENCE: 81

| Leu | Glu | Ala | Ser | Glu | Glu | Val | Glu | Leu | Glu | Pro | Cys | Leu | Ala | Pro | Ser |
| 1 | | | | 5 | | | | | 10 | | | | | 15 | |

| Leu | Glu | Gln | Gln | Glu | Gln | Glu | Leu | Thr | Val | Ala | Leu | Gly | Gln | Pro | Val |
| | | | 20 | | | | | 25 | | | | | 30 | | |

| Arg | Leu | Cys | Cys | Gly | Arg | Ala | Glu | Arg | Gly | Gly | His | Trp | Tyr | Lys | Glu |
| | | 35 | | | | | 40 | | | | | 45 | | | |

| Gly | Ser | Arg | Leu | Ala | Pro | Ala | Gly | Arg | Val | Arg | Gly | Trp | Arg | Gly | Arg |
| | 50 | | | | | 55 | | | | | 60 | | | | |

| Leu | Glu | Ile | Ala | Ser | Phe | Leu | Pro | Glu | Asp | Ala | Gly | Arg | Tyr | Leu | Cys |
| 65 | | | | | 70 | | | | | 75 | | | | | 80 |

| Leu | Ala | Arg | Gly | Ser | Met | Ile | Val | Leu | Gln | Asn | Leu | Thr | Leu | Ile | Thr |
| | | | | 85 | | | | | 90 | | | | | 95 | |

| Gly | Asp | Ser | Leu | Thr | Ser | Ser | Asn | Asp | Asp | Glu | Asp | Pro | Lys | Ser | His |
| | | | 100 | | | | | 105 | | | | | 110 | | |

| Glu | Asp | Pro | Ser | Asn | Arg | His | Ser | Tyr | Pro | Gln | Gln | Ala | Pro | Tyr | Trp |
| | | 115 | | | | | 120 | | | | | 125 | | | |

| Thr | His | Pro | Gln | Arg | Met | Glu | Lys | Lys | Leu | His | Ala | Val | Pro | Ala | Gly |
| | 130 | | | | | 135 | | | | | 140 | | | | |

| Asn | Thr | Val | Lys | Phe | Arg | Cys | Pro | Ala | Ala | Gly | Asn | Pro | Thr | Pro | Thr |
| 145 | | | | | 150 | | | | | 155 | | | | | 160 |

| Ile | Arg | Trp | Leu | Lys | Asp | Gly | Gln | Ala | Phe | His | Gly | Glu | Asn | Arg | Ile |
| | | | | 165 | | | | | 170 | | | | | 175 | |

| Gly | Gly | Ile | Arg | Leu | Arg | His | Gln | His | Trp | Ser | Leu | Val | Met | Glu | Ser |
| | | | 180 | | | | | 185 | | | | | 190 | | |

| Val | Val | Pro | Ser | Asp | Arg | Gly | Thr | Tyr | Thr | Cys | Leu | Val | Glu | Asn | Ala |
| | | 195 | | | | | 200 | | | | | 205 | | | |

| Val | Gly | Ser | Ile | Arg | Tyr | Asn | Tyr | Leu | Leu | Asp | Val | Leu | Glu | Arg | Ser |
| | 210 | | | | | 215 | | | | | 220 | | | | |

| Pro | His | Arg | Pro | Ile | Leu | Gln | Ala | Gly | Leu | Pro | Ala | Asn | Thr | Thr | Ala |
| 225 | | | | | 230 | | | | | 235 | | | | | 240 |

| Val | Val | Gly | Ser | Asp | Val | Glu | Leu | Leu | Cys | Lys | Val | Tyr | Ser | Asp | Ala |
| | | | | 245 | | | | | 250 | | | | | 255 | |

| Gln | Pro | His | Ile | Gln | Trp | Leu | Lys | His | Ile | Val | Ile | Asn | Gly | Ser | Ser |
| | | | 260 | | | | | 265 | | | | | 270 | | |

| Phe | Gly | Ala | Asp | Gly | Phe | Pro | Tyr | Val | Gln | Val | Leu | Lys | Thr | Ala | Asp |
| | | 275 | | | | | 280 | | | | | 285 | | | |

| Ile | Asn | Ser | Ser | Glu | Val | Glu | Val | Leu | Tyr | Leu | Arg | Asn | Val | Ser | Ala |
| | 290 | | | | | 295 | | | | | 300 | | | | |

| Glu | Asp | Ala | Gly | Glu | Tyr | Thr | Cys | Leu | Ala | Gly | Asn | Ser | Ile | Gly | Leu |
| 305 | | | | | 310 | | | | | 315 | | | | | 320 |

| Ser | Tyr | Gln | Ser | Ala | Trp | Leu | Thr | Val | Leu | Pro | Glu | Pro | Lys | Ser | Ser |
| | | | | 325 | | | | | 330 | | | | | 335 | |

| Asp | Lys | Thr | His | Thr | Cys | Pro | Pro | Cys | Pro | Ala | Pro | Glu | Leu | Leu | Gly |
| | | | 340 | | | | | 345 | | | | | 350 | | |

| Gly | Pro | Ser | Val | Phe | Leu | Phe | Pro | Pro | Lys | Pro | Lys | Asp | Thr | Leu | Met |
| | | 355 | | | | | 360 | | | | | 365 | | | |

| Ile | Ser | Arg | Thr | Pro | Glu | Val | Thr | Cys | Val | Val | Val | Asp | Val | Ser | His |
| | 370 | | | | | 375 | | | | | 380 | | | | |

| Glu | Asp | Pro | Glu | Val | Lys | Phe | Asn | Trp | Tyr | Val | Asp | Gly | Val | Glu | Val |

```
                385                 390                 395                 400

His Asn Ala Lys Thr Lys Pro Arg Glu Glu Gln Tyr Asn Ser Thr Tyr
                    405                 410                 415

Arg Val Val Ser Val Leu Thr Val Leu His Gln Asp Trp Leu Asn Gly
                    420                 425                 430

Lys Glu Tyr Lys Cys Lys Val Ser Asn Lys Ala Leu Pro Ala Pro Ile
                    435                 440                 445

Glu Lys Thr Ile Ser Lys Ala Lys Gly Gln Pro Arg Glu Pro Gln Val
            450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                    485                 490                 495

Trp Glu Ser Asn Gly Gln Pro Glu Asn Asn Tyr Lys Thr Thr Pro Pro
                    500                 505                 510

Val Leu Asp Ser Asp Gly Ser Phe Phe Leu Tyr Ser Lys Leu Thr Val
                515                 520                 525

Asp Lys Ser Arg Trp Gln Gln Gly Asn Val Phe Ser Cys Ser Val Met
530                 535                 540

His Glu Ala Leu His Asn His Tyr Thr Gln Lys Ser Leu Ser Leu Ser
545                 550                 555                 560

Pro Gly Lys

<210> SEQ ID NO 82
<211> LENGTH: 563
<212> TYPE: PRT
<213> ORGANISM: Artificial Sequence
<220> FEATURE:
<223> OTHER INFORMATION: FGFR4 ECD delta17 S116E + Fc (also called
      FGFR4ECD(R4Mut4(S116E): delta17)-Fc and R4Mut4(S116E))

<400> SEQUENCE: 82

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
                20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asn Asp Asp Glu Asp Pro Lys Ser His
            100                 105                 110

Arg Asp Pro Glu Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190
```

```
Val Val Pro Ser Asp Arg Gly Thr Tyr Thr Cys Leu Val Glu Asn Ala
            195                 200                 205

Val Gly Ser Ile Arg Tyr Asn Tyr Leu Leu Asp Val Leu Glu Arg Ser
            210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
            245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
            290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
            325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser His
            370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
            405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
            435                 440                 445

Glu Lys Thr Ile Ser Lys Ala Lys Gly Gln Pro Arg Glu Pro Gln Val
            450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
            485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
            530                 535                 540

His Glu Ala Leu His Asn His Tyr Thr Gln Lys Ser Leu Ser Leu Ser
545                 550                 555                 560

Pro Gly Lys

<210> SEQ ID NO 83
<211> LENGTH: 564
<212> TYPE: PRT
<213> ORGANISM: Artificial Sequence
<220> FEATURE:
<223> OTHER INFORMATION: FGFR4 ECD delta17 R4(104-114):R1(106-117) + Fc
      (also called FGFR4ECD(R4Mut4(104-114):FGFR1(106-117): delta 17)-Fc
``` and R4(104-114):R1(106-117))

<400> SEQUENCE: 83

| Leu | Glu | Ala | Ser | Glu | Val | Glu | Leu | Glu | Pro | Cys | Leu | Ala | Pro | Ser |
|---|---|---|---|---|---|---|---|---|---|---|---|---|---|---|
| 1 | | | | 5 | | | | | 10 | | | | | 15 |

| Leu | Glu | Gln | Gln | Glu | Gln | Glu | Leu | Thr | Val | Ala | Leu | Gly | Gln | Pro | Val |
|---|---|---|---|---|---|---|---|---|---|---|---|---|---|---|---|
| | | | 20 | | | | | 25 | | | | | 30 | | |

Arg Leu Cys Cys Gly Arg Ala Glu Arg Gly Gly His Trp Tyr Lys Glu
         35                  40                  45

Gly Ser Arg Leu Ala Pro Ala Gly Arg Val Arg Gly Trp Arg Gly Arg
     50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Asp Ser Ser
             100                 105                 110

Ser Glu Glu Pro Ser Asn Arg His Ser Tyr Pro Gln Gln Ala Pro Tyr
         115                 120                 125

Trp Thr His Pro Gln Arg Met Glu Lys Lys Leu His Ala Val Pro Ala
         130                 135                 140

Gly Asn Thr Val Lys Phe Arg Cys Pro Ala Ala Gly Asn Pro Thr Pro
145                 150                 155                 160

Thr Ile Arg Trp Leu Lys Asp Gly Gln Ala Phe His Gly Glu Asn Arg
             165                 170                 175

Ile Gly Gly Ile Arg Leu Arg His Gln His Trp Ser Leu Val Met Glu
             180                 185                 190

Ser Val Val Pro Ser Asp Arg Gly Thr Tyr Thr Cys Leu Val Glu Asn
         195                 200                 205

Ala Val Gly Ser Ile Arg Tyr Asn Tyr Leu Leu Asp Val Leu Glu Arg
     210                 215                 220

Ser Pro His Arg Pro Ile Leu Gln Ala Gly Leu Pro Ala Asn Thr Thr
225                 230                 235                 240

Ala Val Val Gly Ser Asp Val Glu Leu Leu Cys Lys Val Tyr Ser Asp
             245                 250                 255

Ala Gln Pro His Ile Gln Trp Leu Lys His Ile Val Ile Asn Gly Ser
         260                 265                 270

Ser Phe Gly Ala Asp Gly Phe Pro Tyr Val Gln Val Leu Lys Thr Ala
     275                 280                 285

Asp Ile Asn Ser Ser Glu Val Glu Val Leu Tyr Leu Arg Asn Val Ser
290                 295                 300

Ala Glu Asp Ala Gly Glu Tyr Thr Cys Leu Ala Gly Asn Ser Ile Gly
305                 310                 315                 320

Leu Ser Tyr Gln Ser Ala Trp Leu Thr Val Leu Pro Glu Pro Lys Ser
             325                 330                 335

Ser Asp Lys Thr His Thr Cys Pro Pro Cys Pro Ala Pro Glu Leu Leu
         340                 345                 350

Gly Gly Pro Ser Val Phe Leu Phe Pro Pro Lys Pro Lys Asp Thr Leu
     355                 360                 365

Met Ile Ser Arg Thr Pro Glu Val Thr Cys Val Val Val Asp Val Ser
370                 375                 380

His Glu Asp Pro Glu Val Lys Phe Asn Trp Tyr Val Asp Gly Val Glu
385                 390                 395                 400

Val His Asn Ala Lys Thr Lys Pro Arg Glu Glu Gln Tyr Asn Ser Thr

```
                   405                 410                 415
Tyr Arg Val Val Ser Val Leu Thr Val Leu His Gln Asp Trp Leu Asn
            420                 425                 430

Gly Lys Glu Tyr Lys Cys Lys Val Ser Asn Lys Ala Leu Pro Ala Pro
            435                 440                 445

Ile Glu Lys Thr Ile Ser Lys Ala Lys Gly Gln Pro Arg Glu Pro Gln
    450                 455                 460

Val Tyr Thr Leu Pro Pro Ser Arg Asp Glu Leu Thr Lys Asn Gln Val
465                 470                 475                 480

Ser Leu Thr Cys Leu Val Lys Gly Phe Tyr Pro Ser Asp Ile Ala Val
            485                 490                 495

Glu Trp Glu Ser Asn Gly Gln Pro Glu Asn Asn Tyr Lys Thr Thr Pro
            500                 505                 510

Pro Val Leu Asp Ser Asp Gly Ser Phe Phe Leu Tyr Ser Lys Leu Thr
            515                 520                 525

Val Asp Lys Ser Arg Trp Gln Gln Gly Asn Val Phe Ser Cys Ser Val
530                 535                 540

Met His Glu Ala Leu His Asn His Tyr Thr Gln Lys Ser Leu Ser Leu
545                 550                 555                 560

Ser Pro Gly Lys

<210> SEQ ID NO 84
<211> LENGTH: 563
<212> TYPE: PRT
<213> ORGANISM: Artificial Sequence
<220> FEATURE:
<223> OTHER INFORMATION: FGFR4 ECD delta17 R4(104-114):R1(107-117) + Fc
      (also called FGFR4ECD(R4Mut4(104-114):FGFR1(107-117): delta 17)-Fc
      and R4(104-114):R1(107-117))

<400> SEQUENCE: 84

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Ser Ser Ser Ser
            100                 105                 110

Glu Glu Pro Ser Asn Arg His Ser Tyr Pro Gln Gln Ala Pro Tyr Trp
        115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
```

195                 200                 205
Val Gly Ser Ile Arg Tyr Asn Tyr Leu Leu Asp Val Leu Glu Arg Ser
210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                    245                 250                 255

Gln Pro His Ile Gln Trp Leu Lys His Ile Val Ile Asn Gly Ser Ser
                260                 265                 270

Phe Gly Ala Asp Gly Phe Pro Tyr Val Gln Val Leu Lys Thr Ala Asp
            275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                    325                 330                 335

Asp Lys Thr His Thr Cys Pro Pro Cys Pro Ala Pro Glu Leu Leu Gly
                340                 345                 350

Gly Pro Ser Val Phe Leu Phe Pro Pro Lys Pro Lys Asp Thr Leu Met
            355                 360                 365

Ile Ser Arg Thr Pro Glu Val Thr Cys Val Val Val Asp Val Ser His
        370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                    405                 410                 415

Arg Val Val Ser Val Leu Thr Val Leu His Gln Asp Trp Leu Asn Gly
                420                 425                 430

Lys Glu Tyr Lys Cys Lys Val Ser Asn Lys Ala Leu Pro Ala Pro Ile
            435                 440                 445

Glu Lys Thr Ile Ser Lys Ala Lys Gly Gln Pro Arg Glu Pro Gln Val
        450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                    485                 490                 495

Trp Glu Ser Asn Gly Gln Pro Glu Asn Asn Tyr Lys Thr Thr Pro Pro
                500                 505                 510

Val Leu Asp Ser Asp Gly Ser Phe Phe Leu Tyr Ser Lys Leu Thr Val
            515                 520                 525

Asp Lys Ser Arg Trp Gln Gln Gly Asn Val Phe Ser Cys Ser Val Met
        530                 535                 540

His Glu Ala Leu His Asn His Tyr Thr Gln Lys Ser Leu Ser Leu Ser
545                 550                 555                 560

Pro Gly Lys

<210> SEQ ID NO 85
<211> LENGTH: 565
<212> TYPE: PRT
<213> ORGANISM: Artificial Sequence
<220> FEATURE:
<223> OTHER INFORMATION: FGFR4 ECD delta17 R4(104-110):R1(105-113) + Fc
      (also called FGFR4ECD(R4Mut4(104-110):FGFR1(105-113): delta 17)-Fc
      and R4(104-110):R1(105-113))

```
<400> SEQUENCE: 85

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Asp Ser
            100                 105                 110

Ser His Arg Asp Pro Ser Asn Arg His Ser Tyr Pro Gln Gln Ala Pro
        115                 120                 125

Tyr Trp Thr His Pro Gln Arg Met Glu Lys Lys Leu His Ala Val Pro
130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
                245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro Glu Pro Lys
                325                 330                 335

Ser Ser Asp Lys Thr His Thr Cys Pro Pro Cys Pro Ala Pro Glu Leu
            340                 345                 350

Leu Gly Gly Pro Ser Val Phe Leu Phe Pro Pro Lys Pro Lys Asp Thr
        355                 360                 365

Leu Met Ile Ser Arg Thr Pro Glu Val Thr Cys Val Val Val Asp Val
370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
                405                 410                 415
```

-continued

```
Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
            435                 440                 445

Pro Ile Glu Lys Thr Ile Ser Lys Ala Lys Gly Gln Pro Arg Glu Pro
450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
            485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
            515                 520                 525

Thr Val Asp Lys Ser Arg Trp Gln Gln Gly Asn Val Phe Ser Cys Ser
530                 535                 540

Val Met His Glu Ala Leu His Asn His Tyr Thr Gln Lys Ser Leu Ser
545                 550                 555                 560

Leu Ser Pro Gly Lys
            565

<210> SEQ ID NO 86
<211> LENGTH: 563
<212> TYPE: PRT
<213> ORGANISM: Artificial Sequence
<220> FEATURE:
<223> OTHER INFORMATION: FGFR4 ECD delta17 R4(113-116):R1(116-119) + Fc
      (also called FGFR4ECD(R4Mut4(113-116):FGFR1(116-119): delta 17)-Fc
      and R4(113-116):R1(116-119))

<400> SEQUENCE: 86

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
            85                  90                  95

Gly Asp Ser Leu Thr Ser Ser Asn Asp Asp Glu Asp Pro Lys Ser His
            100                 105                 110

Glu Glu Lys Glu Asn Arg His Ser Tyr Pro Gln Gln Ala Pro Tyr Trp
            115                 120                 125

Thr His Pro Gln Arg Met Glu Lys Lys Leu His Ala Val Pro Ala Gly
            130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
            165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
            195                 200                 205
```

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
        355                 360                 365

Ile Ser Arg Thr Pro Glu Val Thr Cys Val Val Val Asp Val Ser His
370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
            420                 425                 430

Lys Glu Tyr Lys Cys Lys Val Ser Asn Lys Ala Leu Pro Ala Pro Ile
        435                 440                 445

Glu Lys Thr Ile Ser Lys Ala Lys Gly Gln Pro Arg Glu Pro Gln Val
450                 455                 460

Tyr Thr Leu Pro Pro Ser Arg Asp Glu Leu Thr Lys Asn Gln Val Ser
465                 470                 475                 480

Leu Thr Cys Leu Val Lys Gly Phe Tyr Pro Ser Asp Ile Ala Val Glu
                485                 490                 495

Trp Glu Ser Asn Gly Gln Pro Glu Asn Asn Tyr Lys Thr Thr Pro Pro
            500                 505                 510

Val Leu Asp Ser Asp Gly Ser Phe Phe Leu Tyr Ser Lys Leu Thr Val
        515                 520                 525

Asp Lys Ser Arg Trp Gln Gln Gly Asn Val Phe Ser Cys Ser Val Met
530                 535                 540

His Glu Ala Leu His Asn His Tyr Thr Gln Lys Ser Leu Ser Leu Ser
545                 550                 555                 560

Pro Gly Lys

<210> SEQ ID NO 87
<211> LENGTH: 563
<212> TYPE: PRT
<213> ORGANISM: Artificial Sequence
<220> FEATURE:
<223> OTHER INFORMATION: FGFR4 ECD delta17 R4(109-113):R1(112-116) + Fc
      (also called FGFR4ECD(R4Mut4(109-113):FGFR1(112-116): delta 17)-Fc
      and R4(109-113):R1(112-116))

<400> SEQUENCE: 87

```
Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                    85                  90                  95

Gly Asp Ser Leu Thr Ser Ser Asn Asp Asp Glu Asp Asp Ser Ser Ser
                100                 105                 110

Glu Asp Pro Ser Asn Arg His Ser Tyr Pro Gln Gln Ala Pro Tyr Trp
            115                 120                 125

Thr His Pro Gln Arg Met Glu Lys Lys Leu His Ala Val Pro Ala Gly
    130                 135                 140

Asn Thr Val Lys Phe Arg Cys Pro Ala Ala Gly Asn Pro Thr Pro Thr
145                 150                 155                 160

Ile Arg Trp Leu Lys Asp Gly Gln Ala Phe His Gly Glu Asn Arg Ile
                165                 170                 175

Gly Gly Ile Arg Leu Arg His Gln His Trp Ser Leu Val Met Glu Ser
            180                 185                 190

Val Val Pro Ser Asp Arg Gly Thr Tyr Thr Cys Leu Val Glu Asn Ala
        195                 200                 205

Val Gly Ser Ile Arg Tyr Asn Tyr Leu Leu Asp Val Leu Glu Arg Ser
        210                 215                 220

Pro His Arg Pro Ile Leu Gln Ala Gly Leu Pro Ala Asn Thr Thr Ala
225                 230                 235                 240

Val Val Gly Ser Asp Val Glu Leu Leu Cys Lys Val Tyr Ser Asp Ala
                245                 250                 255

Gln Pro His Ile Gln Trp Leu Lys His Ile Val Ile Asn Gly Ser Ser
            260                 265                 270

Phe Gly Ala Asp Gly Phe Pro Tyr Val Gln Val Leu Lys Thr Ala Asp
        275                 280                 285

Ile Asn Ser Ser Glu Val Glu Val Leu Tyr Leu Arg Asn Val Ser Ala
        290                 295                 300

Glu Asp Ala Gly Glu Tyr Thr Cys Leu Ala Gly Asn Ser Ile Gly Leu
305                 310                 315                 320

Ser Tyr Gln Ser Ala Trp Leu Thr Val Leu Pro Glu Pro Lys Ser Ser
                325                 330                 335

Asp Lys Thr His Thr Cys Pro Pro Cys Pro Ala Pro Glu Leu Leu Gly
            340                 345                 350

Gly Pro Ser Val Phe Leu Phe Pro Pro Lys Pro Lys Asp Thr Leu Met
        355                 360                 365

Ile Ser Arg Thr Pro Glu Val Thr Cys Val Val Val Asp Val Ser His
        370                 375                 380

Glu Asp Pro Glu Val Lys Phe Asn Trp Tyr Val Asp Gly Val Glu Val
385                 390                 395                 400

His Asn Ala Lys Thr Lys Pro Arg Glu Glu Gln Tyr Asn Ser Thr Tyr
                405                 410                 415

Arg Val Val Ser Val Leu Thr Val Leu His Gln Asp Trp Leu Asn Gly
```

```
                    420             425             430
Lys Glu Tyr Lys Cys Lys Val Ser Asn Lys Ala Leu Pro Ala Pro Ile
            435                 440                 445
Glu Lys Thr Ile Ser Lys Ala Lys Gly Gln Pro Arg Glu Pro Gln Val
        450                 455                 460
Tyr Thr Leu Pro Pro Ser Arg Asp Glu Leu Thr Lys Asn Gln Val Ser
465                 470                 475                 480
Leu Thr Cys Leu Val Lys Gly Phe Tyr Pro Ser Asp Ile Ala Val Glu
                485                 490                 495
Trp Glu Ser Asn Gly Gln Pro Glu Asn Asn Tyr Lys Thr Thr Pro Pro
                    500                 505                 510
Val Leu Asp Ser Asp Gly Ser Phe Phe Leu Tyr Ser Lys Leu Thr Val
            515                 520                 525
Asp Lys Ser Arg Trp Gln Gln Gly Asn Val Phe Ser Cys Ser Val Met
        530                 535                 540
His Glu Ala Leu His Asn His Tyr Thr Gln Lys Ser Leu Ser Leu Ser
545                 550                 555                 560
Pro Gly Lys

<210> SEQ ID NO 88
<211> LENGTH: 566
<212> TYPE: PRT
<213> ORGANISM: Artificial Sequence
<220> FEATURE:
<223> OTHER INFORMATION: FGFR4 ECD delta17 R1 D1-D2 linker chimera
      (N91A) + Fc (also called FGFR4ECD(ABMut1(N91A): delta 17)-Fc and
      ABMut1(N91A))

<400> SEQUENCE: 88

Leu Glu Ala Ser Glu Glu Val Glu Leu Glu Pro Cys Leu Ala Pro Ser
1               5                   10                  15
Leu Glu Gln Gln Glu Gln Glu Leu Thr Val Ala Leu Gly Gln Pro Val
            20                  25                  30
Arg Leu Cys Cys Gly Arg Ala Glu Arg Gly Gly His Trp Tyr Lys Glu
        35                  40                  45
Gly Ser Arg Leu Ala Pro Ala Gly Arg Val Arg Gly Trp Arg Gly Arg
    50                  55                  60
Leu Glu Ile Ala Ser Phe Leu Pro Glu Asp Ala Gly Arg Tyr Leu Cys
65                  70                  75                  80
Leu Ala Arg Gly Ser Met Ile Val Leu Gln Ala Leu Thr Leu Ile Thr
                85                  90                  95
Gly Asp Ala Leu Pro Ser Ser Glu Asp Asp Asp Asp Asp Asp Asp Ser
            100                 105                 110
Ser Ser Glu Glu Lys Glu Thr Asp Asn Thr Lys Pro Asn Pro Val Ala
        115                 120                 125
Pro Tyr Trp Thr His Pro Gln Arg Met Glu Lys Lys Leu His Ala Val
    130                 135                 140
Pro Ala Gly Asn Thr Val Lys Phe Arg Cys Pro Ala Ala Gly Asn Pro
145                 150                 155                 160
Thr Pro Thr Ile Arg Trp Leu Lys Asp Gly Gln Ala Phe His Gly Glu
                165                 170                 175
Asn Arg Ile Gly Gly Ile Arg Leu Arg His Gln His Trp Ser Leu Val
            180                 185                 190
Met Glu Ser Val Val Pro Ser Asp Arg Gly Thr Tyr Thr Cys Leu Val
        195                 200                 205
Glu Asn Ala Val Gly Ser Ile Arg Tyr Asn Tyr Leu Leu Asp Val Leu
```

-continued

```
            210                 215                 220
Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
                260                 265                 270

Gly Ser Ser Phe Gly Ala Asp Gly Phe Pro Tyr Val Gln Val Leu Lys
            275                 280                 285

Thr Ala Asp Ile Asn Ser Ser Glu Val Glu Val Leu Tyr Leu Arg Asn
290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
                325                 330                 335

Lys Ser Ser Asp Lys Thr His Thr Cys Pro Pro Cys Pro Ala Pro Glu
                340                 345                 350

Leu Leu Gly Gly Pro Ser Val Phe Leu Phe Pro Pro Lys Pro Lys Asp
            355                 360                 365

Thr Leu Met Ile Ser Arg Thr Pro Glu Val Thr Cys Val Val Val Asp
370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
                420                 425                 430

Leu Asn Gly Lys Glu Tyr Lys Cys Lys Val Ser Asn Lys Ala Leu Pro
            435                 440                 445

Ala Pro Ile Glu Lys Thr Ile Ser Lys Ala Lys Gly Gln Pro Arg Glu
450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
                500                 505                 510

Thr Pro Pro Val Leu Asp Ser Asp Gly Ser Phe Phe Leu Tyr Ser Lys
            515                 520                 525

Leu Thr Val Asp Lys Ser Arg Trp Gln Gln Gly Asn Val Phe Ser Cys
530                 535                 540

Ser Val Met His Glu Ala Leu His Asn His Tyr Thr Gln Lys Ser Leu
545                 550                 555                 560

Ser Leu Ser Pro Gly Lys
                565
```

<210> SEQ ID NO 89
<211> LENGTH: 566
<212> TYPE: PRT
<213> ORGANISM: Artificial Sequence
<220> FEATURE:
<223> OTHER INFORMATION: FGFR4 ECD delta17 R1 D1-D2 linker chimera
      (N159A) + Fc (also called FGFR4ECD(ABMut1(N159A): delta 17)-Fc and
      ABMut1(N159A))

<400> SEQUENCE: 89

-continued

```
Leu Glu Ala Ser Glu Val Glu Leu Glu Pro Cys Leu Ala Pro Ser
1               5                   10                  15

Leu Glu Gln Gln Gln Gln Leu Thr Val Ala Leu Gly Gln Pro Val
            20                  25                  30

Arg Leu Cys Cys Gly Arg Ala Glu Arg Gly Gly His Trp Tyr Lys Glu
            35                  40                  45

Gly Ser Arg Leu Ala Pro Ala Gly Arg Val Arg Gly Trp Arg Gly Arg
        50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ala Leu Pro Ser Ser Glu Asp Asp Asp Asp Asp Asp Ser
            100                 105                 110

Ser Ser Glu Glu Lys Glu Thr Asp Asn Thr Lys Pro Asn Pro Val Ala
        115                 120                 125

Pro Tyr Trp Thr His Pro Gln Arg Met Glu Lys Lys Leu His Ala Val
    130                 135                 140

Pro Ala Gly Asn Thr Val Lys Phe Arg Cys Pro Ala Ala Gly Ala Pro
145                 150                 155                 160

Thr Pro Thr Ile Arg Trp Leu Lys Asp Gly Gln Ala Phe His Gly Glu
                165                 170                 175

Asn Arg Ile Gly Gly Ile Arg Leu Arg His Gln His Trp Ser Leu Val
            180                 185                 190

Met Glu Ser Val Val Pro Ser Asp Arg Gly Thr Tyr Thr Cys Leu Val
        195                 200                 205

Glu Asn Ala Val Gly Ser Ile Arg Tyr Asn Tyr Leu Leu Asp Val Leu
    210                 215                 220

Glu Arg Ser Pro His Arg Pro Ile Leu Gln Ala Gly Leu Pro Ala Asn
225                 230                 235                 240

Thr Thr Ala Val Val Gly Ser Asp Val Glu Leu Leu Cys Lys Val Tyr
                245                 250                 255

Ser Asp Ala Gln Pro His Ile Gln Trp Leu Lys His Ile Val Ile Asn
            260                 265                 270

Gly Ser Ser Phe Gly Ala Asp Gly Phe Pro Tyr Val Gln Val Leu Lys
        275                 280                 285

Thr Ala Asp Ile Asn Ser Ser Glu Val Glu Val Leu Tyr Leu Arg Asn
    290                 295                 300

Val Ser Ala Glu Asp Ala Gly Glu Tyr Thr Cys Leu Ala Gly Asn Ser
305                 310                 315                 320

Ile Gly Leu Ser Tyr Gln Ser Ala Trp Leu Thr Val Leu Pro Glu Pro
                325                 330                 335

Lys Ser Ser Asp Lys Thr His Thr Cys Pro Pro Cys Pro Ala Pro Glu
            340                 345                 350

Leu Leu Gly Gly Pro Ser Val Phe Leu Phe Pro Pro Lys Pro Lys Asp
        355                 360                 365

Thr Leu Met Ile Ser Arg Thr Pro Glu Val Thr Cys Val Val Val Asp
    370                 375                 380

Val Ser His Glu Asp Pro Glu Val Lys Phe Asn Trp Tyr Val Asp Gly
385                 390                 395                 400

Val Glu Val His Asn Ala Lys Thr Lys Pro Arg Glu Glu Gln Tyr Asn
                405                 410                 415

Ser Thr Tyr Arg Val Val Ser Val Leu Thr Val Leu His Gln Asp Trp
            420                 425                 430
```

```
Leu Asn Gly Lys Glu Tyr Lys Cys Lys Val Ser Asn Lys Ala Leu Pro
            435                 440                 445

Ala Pro Ile Glu Lys Thr Ile Ser Lys Ala Lys Gly Gln Pro Arg Glu
    450                 455                 460

Pro Gln Val Tyr Thr Leu Pro Pro Ser Arg Asp Glu Leu Thr Lys Asn
465                 470                 475                 480

Gln Val Ser Leu Thr Cys Leu Val Lys Gly Phe Tyr Pro Ser Asp Ile
                485                 490                 495

Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
        515                 520                 525

Leu Thr Val Asp Lys Ser Arg Trp Gln Gln Gly Asn Val Phe Ser Cys
    530                 535                 540

Ser Val Met His Glu Ala Leu His Asn His Tyr Thr Gln Lys Ser Leu
545                 550                 555                 560

Ser Leu Ser Pro Gly Lys
                565

<210> SEQ ID NO 90
<211> LENGTH: 333
<212> TYPE: PRT
<213> ORGANISM: Artificial Sequence
<220> FEATURE:
<223> OTHER INFORMATION: FGFR4 ECD delta17 R4(104-114):R1(105-117) acid
      box chimera

<400> SEQUENCE: 90

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Glu Asp Asp Asp Asp Asp Asp Asp Ser
            100                 105                 110

Ser Ser Glu Glu Pro Ser Asn Arg His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220
```

```
Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
            245                 250                 255

Asp Ala Gln Pro His Ile Gln Trp Leu Lys His Ile Val Ile Asn Gly
            260                 265                 270

Ser Ser Phe Gly Ala Asp Gly Phe Pro Tyr Val Gln Val Leu Lys Thr
        275                 280                 285

Ala Asp Ile Asn Ser Ser Glu Val Glu Val Leu Tyr Leu Arg Asn Val
    290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro
                325                 330

<210> SEQ ID NO 91
<211> LENGTH: 565
<212> TYPE: PRT
<213> ORGANISM: Artificial Sequence
<220> FEATURE:
<223> OTHER INFORMATION: FGFR4 ECD delta17 R4(104-114):R1(105-117) acid
      box chimera + Fc (also called FGF4ECD(ABMut3: delta17)-Fc or
      ABMut3)

<400> SEQUENCE: 91

Leu Glu Ala Ser Glu Glu Val Glu Leu Glu Pro Cys Leu Ala Pro Ser
1               5                   10                  15

Leu Glu Gln Gln Glu Gln Leu Thr Val Ala Leu Gly Gln Pro Val
            20                  25                  30

Arg Leu Cys Cys Gly Arg Ala Glu Arg Gly Gly His Trp Tyr Lys Glu
        35                  40                  45

Gly Ser Arg Leu Ala Pro Ala Gly Arg Val Arg Gly Trp Arg Gly Arg
    50                  55                  60

Leu Glu Ile Ala Ser Phe Leu Pro Glu Asp Ala Gly Arg Tyr Leu Cys
65                  70                  75                  80

Leu Ala Arg Gly Ser Met Ile Val Leu Gln Asn Leu Thr Leu Ile Thr
                85                  90                  95

Gly Asp Ser Leu Thr Ser Ser Asp Asp Asp Asp Asp Asp Asp Asp Ser
            100                 105                 110

Ser Ser Glu Glu Pro Ser Asn Arg His Ser Tyr Pro Gln Gln Ala Pro
        115                 120                 125

Tyr Trp Thr His Pro Gln Arg Met Glu Lys Lys Leu His Ala Val Pro
    130                 135                 140

Ala Gly Asn Thr Val Lys Phe Arg Cys Pro Ala Ala Gly Asn Pro Thr
145                 150                 155                 160

Pro Thr Ile Arg Trp Leu Lys Asp Gly Gln Ala Phe His Gly Glu Asn
                165                 170                 175

Arg Ile Gly Gly Ile Arg Leu Arg His Gln His Trp Ser Leu Val Met
            180                 185                 190

Glu Ser Val Val Pro Ser Asp Arg Gly Thr Tyr Thr Cys Leu Val Glu
        195                 200                 205

Asn Ala Val Gly Ser Ile Arg Tyr Asn Tyr Leu Leu Asp Val Leu Glu
    210                 215                 220

Arg Ser Pro His Arg Pro Ile Leu Gln Ala Gly Leu Pro Ala Asn Thr
225                 230                 235                 240

Thr Ala Val Val Gly Ser Asp Val Glu Leu Leu Cys Lys Val Tyr Ser
```

```
                245                 250                 255
Asp Ala Gln Pro His Ile Gln Trp Leu Lys His Ile Val Ile Asn Gly
                260                 265                 270

Ser Ser Phe Gly Ala Asp Gly Phe Pro Tyr Val Gln Val Leu Lys Thr
            275                 280                 285

Ala Asp Ile Asn Ser Ser Glu Val Glu Val Leu Tyr Leu Arg Asn Val
        290                 295                 300

Ser Ala Glu Asp Ala Gly Glu Tyr Thr Cys Leu Ala Gly Asn Ser Ile
305                 310                 315                 320

Gly Leu Ser Tyr Gln Ser Ala Trp Leu Thr Val Leu Pro Glu Pro Lys
                325                 330                 335

Ser Ser Asp Lys Thr His Thr Cys Pro Pro Cys Pro Ala Pro Glu Leu
                340                 345                 350

Leu Gly Gly Pro Ser Val Phe Leu Phe Pro Pro Lys Pro Lys Asp Thr
            355                 360                 365

Leu Met Ile Ser Arg Thr Pro Glu Val Thr Cys Val Val Val Asp Val
        370                 375                 380

Ser His Glu Asp Pro Glu Val Lys Phe Asn Trp Tyr Val Asp Gly Val
385                 390                 395                 400

Glu Val His Asn Ala Lys Thr Lys Pro Arg Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
        435                 440                 445

Pro Ile Glu Lys Thr Ile Ser Lys Ala Lys Gly Gln Pro Arg Glu Pro
    450                 455                 460

Gln Val Tyr Thr Leu Pro Pro Ser Arg Asp Glu Leu Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
    530                 535                 540

Val Met His Glu Ala Leu His Asn His Tyr Thr Gln Lys Ser Leu Ser
545                 550                 555                 560

Leu Ser Pro Gly Lys
                565

<210> SEQ ID NO 92
<211> LENGTH: 334
<212> TYPE: PRT
<213> ORGANISM: Artificial Sequence
<220> FEATURE:
<223> OTHER INFORMATION: FGFR4 ECD delta17 R1 D1-D2 linker chimera
      (N91A, N159A)

<400> SEQUENCE: 92

Leu Glu Ala Ser Glu Glu Val Glu Leu Glu Pro Cys Leu Ala Pro Ser
1               5                   10                  15

Leu Glu Gln Gln Glu Gln Glu Leu Thr Val Ala Leu Gly Gln Pro Val
            20                  25                  30

Arg Leu Cys Cys Gly Arg Ala Glu Arg Gly Gly His Trp Tyr Lys Glu
```

```
                 35                  40                  45
Gly Ser Arg Leu Ala Pro Ala Gly Arg Val Arg Gly Trp Arg Gly Arg
            50                  55                  60
Leu Glu Ile Ala Ser Phe Leu Pro Glu Asp Ala Gly Arg Tyr Leu Cys
65                  70                  75                  80
Leu Ala Arg Gly Ser Met Ile Val Leu Gln Ala Leu Thr Leu Ile Thr
                85                  90                  95
Gly Asp Ala Leu Pro Ser Ser Glu Asp Asp Asp Asp Asp Asp Asp Ser
            100                 105                 110
Ser Ser Glu Glu Lys Glu Thr Asp Asn Thr Lys Pro Asn Pro Val Ala
            115                 120                 125
Pro Tyr Trp Thr His Pro Gln Arg Met Glu Lys Lys Leu His Ala Val
            130                 135                 140
Pro Ala Gly Asn Thr Val Lys Phe Arg Cys Pro Ala Ala Gly Ala Pro
145                 150                 155                 160
Thr Pro Thr Ile Arg Trp Leu Lys Asp Gly Gln Ala Phe His Gly Glu
                165                 170                 175
Asn Arg Ile Gly Gly Ile Arg Leu Arg His Gln His Trp Ser Leu Val
            180                 185                 190
Met Glu Ser Val Val Pro Ser Asp Arg Gly Thr Tyr Thr Cys Leu Val
            195                 200                 205
Glu Asn Ala Val Gly Ser Ile Arg Tyr Asn Tyr Leu Leu Asp Val Leu
            210                 215                 220
Glu Arg Ser Pro His Arg Pro Ile Leu Gln Ala Gly Leu Pro Ala Asn
225                 230                 235                 240
Thr Thr Ala Val Val Gly Ser Asp Val Glu Leu Leu Cys Lys Val Tyr
                245                 250                 255
Ser Asp Ala Gln Pro His Ile Gln Trp Leu Lys His Ile Val Ile Asn
            260                 265                 270
Gly Ser Ser Phe Gly Ala Asp Gly Phe Pro Tyr Val Gln Val Leu Lys
            275                 280                 285
Thr Ala Asp Ile Asn Ser Ser Glu Val Glu Val Leu Tyr Leu Arg Asn
            290                 295                 300
Val Ser Ala Glu Asp Ala Gly Glu Tyr Thr Cys Leu Ala Gly Asn Ser
305                 310                 315                 320
Ile Gly Leu Ser Tyr Gln Ser Ala Trp Leu Thr Val Leu Pro
                325                 330

<210> SEQ ID NO 93
<211> LENGTH: 566
<212> TYPE: PRT
<213> ORGANISM: Artificial Sequence
<220> FEATURE:
<223> OTHER INFORMATION: FGFR4 ECD delta17 R1 D1-D2 linker chimera
      (N91A, N159A) + Fc

<400> SEQUENCE: 93

Leu Glu Ala Ser Glu Glu Val Glu Leu Glu Pro Cys Leu Ala Pro Ser
1               5                   10                  15
Leu Glu Gln Gln Glu Gln Glu Leu Thr Val Ala Leu Gly Gln Pro Val
            20                  25                  30
Arg Leu Cys Cys Gly Arg Ala Glu Arg Gly Gly His Trp Tyr Lys Glu
            35                  40                  45
Gly Ser Arg Leu Ala Pro Ala Gly Arg Val Arg Gly Trp Arg Gly Arg
            50                  55                  60
Leu Glu Ile Ala Ser Phe Leu Pro Glu Asp Ala Gly Arg Tyr Leu Cys
```

```
                65                  70                  75                  80
Leu Ala Arg Gly Ser Met Ile Val Leu Gln Ala Leu Thr Leu Ile Thr
                    85                  90                  95
Gly Asp Ala Leu Pro Ser Ser Glu Asp Asp Asp Asp Asp Asp Asp Ser
                    100                 105                 110
Ser Ser Glu Glu Lys Glu Thr Asp Asn Thr Lys Pro Asn Pro Val Ala
                    115                 120                 125
Pro Tyr Trp Thr His Pro Gln Arg Met Glu Lys Lys Leu His Ala Val
                    130                 135                 140
Pro Ala Gly Asn Thr Val Lys Phe Arg Cys Pro Ala Ala Gly Ala Pro
145                 150                 155                 160
Thr Pro Thr Ile Arg Trp Leu Lys Asp Gly Gln Ala Phe His Gly Glu
                    165                 170                 175
Asn Arg Ile Gly Gly Ile Arg Leu Arg His Gln His Trp Ser Leu Val
                    180                 185                 190
Met Glu Ser Val Val Pro Ser Asp Arg Gly Thr Tyr Thr Cys Leu Val
                    195                 200                 205
Glu Asn Ala Val Gly Ser Ile Arg Tyr Asn Tyr Leu Leu Asp Val Leu
                    210                 215                 220
Glu Arg Ser Pro His Arg Pro Ile Leu Gln Ala Gly Leu Pro Ala Asn
225                 230                 235                 240
Thr Thr Ala Val Val Gly Ser Asp Val Glu Leu Leu Cys Lys Val Tyr
                    245                 250                 255
Ser Asp Ala Gln Pro His Ile Gln Trp Leu Lys His Ile Val Ile Asn
                    260                 265                 270
Gly Ser Ser Phe Gly Ala Asp Gly Phe Pro Tyr Val Gln Val Leu Lys
                    275                 280                 285
Thr Ala Asp Ile Asn Ser Ser Glu Val Glu Val Leu Tyr Leu Arg Asn
                    290                 295                 300
Val Ser Ala Glu Asp Ala Gly Glu Tyr Thr Cys Leu Ala Gly Asn Ser
305                 310                 315                 320
Ile Gly Leu Ser Tyr Gln Ser Ala Trp Leu Thr Val Leu Pro Glu Pro
                    325                 330                 335
Lys Ser Ser Asp Lys Thr His Thr Cys Pro Pro Cys Pro Ala Pro Glu
                    340                 345                 350
Leu Leu Gly Gly Pro Ser Val Phe Leu Phe Pro Pro Lys Pro Lys Asp
                    355                 360                 365
Thr Leu Met Ile Ser Arg Thr Pro Glu Val Thr Cys Val Val Val Asp
                    370                 375                 380
Val Ser His Glu Asp Pro Glu Val Lys Phe Asn Trp Tyr Val Asp Gly
385                 390                 395                 400
Val Glu Val His Asn Ala Lys Thr Lys Pro Arg Glu Glu Gln Tyr Asn
                    405                 410                 415
Ser Thr Tyr Arg Val Val Ser Val Leu Thr Val Leu His Gln Asp Trp
                    420                 425                 430
Leu Asn Gly Lys Glu Tyr Lys Cys Lys Val Ser Asn Lys Ala Leu Pro
                    435                 440                 445
Ala Pro Ile Glu Lys Thr Ile Ser Lys Ala Lys Gly Gln Pro Arg Glu
                    450                 455                 460
Pro Gln Val Tyr Thr Leu Pro Pro Ser Arg Asp Glu Leu Thr Lys Asn
465                 470                 475                 480
Gln Val Ser Leu Thr Cys Leu Val Lys Gly Phe Tyr Pro Ser Asp Ile
                    485                 490                 495
```

```
Ala Val Glu Trp Glu Ser Asn Gly Gln Pro Glu Asn Asn Tyr Lys Thr
            500                 505                 510

Thr Pro Pro Val Leu Asp Ser Asp Gly Ser Phe Phe Leu Tyr Ser Lys
            515                 520                 525

Leu Thr Val Asp Lys Ser Arg Trp Gln Gln Gly Asn Val Phe Ser Cys
            530                 535                 540

Ser Val Met His Glu Ala Leu His Asn His Tyr Thr Gln Lys Ser Leu
545                 550                 555                 560

Ser Leu Ser Pro Gly Lys
                565

<210> SEQ ID NO 94
<211> LENGTH: 229
<212> TYPE: PRT
<213> ORGANISM: Artificial Sequence
<220> FEATURE:
<223> OTHER INFORMATION: Fc

<400> SEQUENCE: 94

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 95
<211> LENGTH: 228
<212> TYPE: PRT
<213> ORGANISM: Artificial Sequence
<220> FEATURE:
<223> OTHER INFORMATION: Fc

<400> SEQUENCE: 95
```

```
Glu Arg Lys Ser Ser Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
50                  55                  60

Val His Asn Ala Lys Thr Lys Pro Arg Glu Glu Gln Phe Asn Ser Thr
65              70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
210                 215                 220

Ser Pro Gly Lys
225

<210> SEQ ID NO 96
<211> LENGTH: 339
<212> TYPE: PRT
<213> ORGANISM: Artificial Sequence
<220> FEATURE:
<223> OTHER INFORMATION: FGFR1 ECD delta14

<400> SEQUENCE: 96

Arg Pro Ser Pro Thr Leu Pro Glu Gln Ala Gln Pro Trp Gly Ala Pro
1               5                   10                  15

Val Glu Val Glu Ser Phe Leu Val His Pro Gly Asp Leu Leu Gln Leu
            20                  25                  30

Arg Cys Arg Leu Arg Asp Asp Val Gln Ser Ile Asn Trp Leu Arg Asp
        35                  40                  45

Gly Val Gln Leu Ala Glu Ser Asn Arg Thr Arg Ile Thr Gly Glu Glu
50                  55                  60

Val Glu Val Gln Asp Ser Val Pro Ala Asp Ser Gly Leu Tyr Ala Cys
65              70                  75                  80

Val Thr Ser Ser Pro Ser Gly Ser Asp Thr Thr Tyr Phe Ser Val Asn
                85                  90                  95

Val Ser Asp Ala Leu Pro Ser Ser Glu Asp Asp Asp Asp Asp Asp Asp
            100                 105                 110

Ser Ser Ser Glu Glu Lys Glu Thr Asp Asn Thr Lys Pro Asn Pro Val
        115                 120                 125

Ala Pro Tyr Trp Thr Ser Pro Glu Lys Met Glu Lys Lys Leu His Ala
```

```
               130                 135                 140
Val Pro Ala Ala Lys Thr Val Lys Phe Lys Cys Pro Ser Ser Gly Thr
145                 150                 155                 160

Pro Asn Pro Thr Leu Arg Trp Leu Lys Asn Gly Lys Glu Phe Lys Pro
                165                 170                 175

Asp His Arg Ile Gly Gly Tyr Lys Val Arg Tyr Ala Thr Trp Ser Ile
                180                 185                 190

Ile Met Asp Ser Val Val Pro Ser Asp Lys Gly Asn Tyr Thr Cys Ile
                195                 200                 205

Val Glu Asn Glu Tyr Gly Ser Ile Asn His Thr Tyr Gln Leu Asp Val
                210                 215                 220

Val Glu Arg Ser Pro His Arg Pro Ile Leu Gln Ala Gly Leu Pro Ala
225                 230                 235                 240

Asn Lys Thr Val Ala Leu Gly Ser Asn Val Glu Phe Met Cys Lys Val
                245                 250                 255

Tyr Ser Asp Pro Gln Pro His Ile Gln Trp Leu Lys His Ile Glu Val
                260                 265                 270

Asn Gly Ser Lys Ile Gly Pro Asp Asn Leu Pro Tyr Val Gln Ile Leu
                275                 280                 285

Lys Thr Ala Gly Val Asn Thr Thr Asp Lys Glu Met Glu Val Leu His
                290                 295                 300

Leu Arg Asn Val Ser Phe Glu Asp Ala Gly Glu Tyr Thr Cys Leu Ala
305                 310                 315                 320

Gly Asn Ser Ile Gly Leu Ser His His Ser Ala Trp Leu Thr Val Leu
                325                 330                 335

Glu Ala Leu

<210> SEQ ID NO 97
<211> LENGTH: 374
<212> TYPE: PRT
<213> ORGANISM: Artificial Sequence
<220> FEATURE:
<223> OTHER INFORMATION: FGFR1 ECD w/ signal peptide

<400> SEQUENCE: 97

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
                35                  40                  45

Asp Leu Leu Gln Leu Arg Cys Arg Leu Arg Asp Asp Val Gln Ser Ile
                50                  55                  60

Asn Trp Leu Arg Asp Gly Val Gln Leu Ala Glu Ser Asn Arg Thr Arg
65              70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
                100                 105                 110

Tyr Phe Ser Val Asn Val Ser Asp Ala Leu Pro Ser Ser Glu Asp Asp
                115                 120                 125

Asp Asp Asp Asp Asp Ser Ser Ser Glu Glu Lys Glu Thr Asp Asn Thr
                130                 135                 140

Lys Pro Asn Pro Val Ala Pro Tyr Trp Thr Ser Pro Glu Lys Met Glu
145                 150                 155                 160
```

```
Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu
    370

<210> SEQ ID NO 98
<211> LENGTH: 89
<212> TYPE: PRT
<213> ORGANISM: Artificial Sequence
<220> FEATURE:
<223> OTHER INFORMATION: FGFR4 D1 Domain

<400> SEQUENCE: 98

Leu Glu Pro Cys Leu Ala Pro Ser Leu Glu Gln Gln Glu Gln Glu Leu
1               5                   10                  15

Thr Val Ala Leu Gly Gln Pro Val Arg Leu Cys Cys Gly Arg Ala Glu
            20                  25                  30

Arg Gly Gly His Trp Tyr Lys Glu Gly Ser Arg Leu Ala Pro Ala Gly
        35                  40                  45

Arg Val Arg Gly Trp Arg Gly Arg Leu Glu Ile Ala Ser Phe Leu Pro
    50                  55                  60

Glu Asp Ala Gly Arg Tyr Leu Cys Leu Ala Arg Gly Ser Met Ile Val
65                  70                  75                  80

Leu Gln Asn Leu Thr Leu Ile Thr Gly
                85

<210> SEQ ID NO 99
<211> LENGTH: 95
<212> TYPE: PRT
<213> ORGANISM: Artificial Sequence
<220> FEATURE:
<223> OTHER INFORMATION: FGFR4 D2 Domain

<400> SEQUENCE: 99
```

Ala Pro Tyr Trp Thr His Pro Gln Arg Met Glu Lys Lys Leu His Ala
1               5                   10                  15

Val Pro Ala Gly Asn Thr Val Lys Phe Arg Cys Pro Ala Ala Gly Asn
            20                  25                  30

Pro Thr Pro Thr Ile Arg Trp Leu Lys Asp Gly Gln Ala Phe His Gly
        35                  40                  45

Glu Asn Arg Ile Gly Gly Ile Arg Leu Arg His Gln His Trp Ser Leu
    50                  55                  60

Val Met Glu Ser Val Val Pro Ser Asp Arg Gly Thr Tyr Thr Cys Leu
65                  70                  75                  80

Val Glu Asn Ala Val Gly Ser Ile Arg Tyr Asn Tyr Leu Leu Asp
                85                  90                  95

<210> SEQ ID NO 100
<211> LENGTH: 95
<212> TYPE: PRT
<213> ORGANISM: Artificial Sequence
<220> FEATURE:
<223> OTHER INFORMATION: FGFR4 T158A D2 Domain

<400> SEQUENCE: 100

Ala Pro Tyr Trp Thr His Pro Gln Arg Met Glu Lys Lys Leu His Ala
1               5                   10                  15

Val Pro Ala Gly Asn Thr Val Lys Phe Arg Cys Pro Ala Ala Gly Asn
            20                  25                  30

Pro Ala Pro Thr Ile Arg Trp Leu Lys Asp Gly Gln Ala Phe His Gly
        35                  40                  45

Glu Asn Arg Ile Gly Gly Ile Arg Leu Arg His Gln His Trp Ser Leu
    50                  55                  60

Val Met Glu Ser Val Val Pro Ser Asp Arg Gly Thr Tyr Thr Cys Leu
65                  70                  75                  80

Val Glu Asn Ala Val Gly Ser Ile Arg Tyr Asn Tyr Leu Leu Asp
                85                  90                  95

<210> SEQ ID NO 101
<211> LENGTH: 101
<212> TYPE: PRT
<213> ORGANISM: Artificial Sequence
<220> FEATURE:
<223> OTHER INFORMATION: FGFR4 D3 Domain

<400> SEQUENCE: 101

Pro Ile Leu Gln Ala Gly Leu Pro Ala Asn Thr Thr Ala Val Val Gly
1               5                   10                  15

Ser Asp Val Glu Leu Leu Cys Lys Val Tyr Ser Asp Ala Gln Pro His
            20                  25                  30

Ile Gln Trp Leu Lys His Ile Val Ile Asn Gly Ser Ser Phe Gly Ala
        35                  40                  45

Asp Gly Phe Pro Tyr Val Gln Val Leu Lys Thr Ala Asp Ile Asn Ser
    50                  55                  60

Ser Glu Val Glu Val Leu Tyr Leu Arg Asn Val Ser Ala Glu Asp Ala
65                  70                  75                  80

Gly Glu Tyr Thr Cys Leu Ala Gly Asn Ser Ile Gly Leu Ser Tyr Gln
                85                  90                  95

Ser Ala Trp Leu Thr
            100

<210> SEQ ID NO 102
<211> LENGTH: 101

```
<212> TYPE: PRT
<213> ORGANISM: Artificial Sequence
<220> FEATURE:
<223> OTHER INFORMATION: FGFR4 D276V D3 Domain

<400> SEQUENCE: 102

Pro Ile Leu Gln Ala Gly Leu Pro Ala Asn Thr Thr Ala Val Val Gly
1               5                   10                  15

Ser Asp Val Glu Leu Leu Cys Lys Val Tyr Ser Asp Ala Gln Pro His
                20                  25                  30

Ile Gln Trp Leu Lys His Ile Val Ile Asn Gly Ser Ser Phe Gly Ala
            35                  40                  45

Val Gly Phe Pro Tyr Val Gln Val Leu Lys Thr Ala Asp Ile Asn Ser
    50                  55                  60

Ser Glu Val Glu Val Leu Tyr Leu Arg Asn Val Ser Ala Glu Asp Ala
65                  70                  75                  80

Gly Glu Tyr Thr Cys Leu Ala Gly Asn Ser Ile Gly Leu Ser Tyr Gln
                85                  90                  95

Ser Ala Trp Leu Thr
            100

<210> SEQ ID NO 103
<211> LENGTH: 8
<212> TYPE: PRT
<213> ORGANISM: Artificial Sequence
<220> FEATURE:
<223> OTHER INFORMATION: FGFR4 D2-D3 Linker

<400> SEQUENCE: 103

Val Leu Glu Arg Ser Pro His Arg
1               5

<210> SEQ ID NO 104
<211> LENGTH: 8
<212> TYPE: PRT
<213> ORGANISM: Artificial Sequence
<220> FEATURE:
<223> OTHER INFORMATION: FGFR1 short acid box

<400> SEQUENCE: 104

Glu Asp Asp Asp Asp Asp Asp Asp
1               5

<210> SEQ ID NO 105
<211> LENGTH: 352
<212> TYPE: PRT
<213> ORGANISM: Artificial Sequence
<220> FEATURE:
<223> OTHER INFORMATION: signal peptide + FGFR4 ECD delta17

<400> SEQUENCE: 105

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
                20                  25                  30

Cys Leu Ala Pro Ser Leu Glu Gln Gln Glu Gln Glu Leu Thr Val Ala
            35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
```

-continued

```
                     85                    90                    95
Gly Arg Tyr Leu Cys Leu Ala Arg Gly Ser Met Ile Val Leu Gln Asn
            100                   105                   110

Leu Thr Leu Ile Thr Gly Asp Ser Leu Thr Ser Ser Asn Asp Asp Glu
            115                   120                   125

Asp Pro Lys Ser His Arg Asp Pro Ser Asn Arg His Ser Tyr Pro Gln
            130                   135                   140

Gln Ala Pro Tyr Trp Thr His Pro Gln Arg Met Glu Lys Lys Leu His
145                   150                   155                   160

Ala Val Pro Ala Gly Asn Thr Val Lys Phe Arg Cys Pro Ala Ala Gly
                165                   170                   175

Asn Pro Thr Pro Thr Ile Arg Trp Leu Lys Asp Gly Gln Ala Phe His
            180                   185                   190

Gly Glu Asn Arg Ile Gly Gly Ile Arg Leu Arg His Gln His Trp Ser
            195                   200                   205

Leu Val Met Glu Ser Val Val Pro Ser Asp Arg Gly Thr Tyr Thr Cys
            210                   215                   220

Leu Val Glu Asn Ala Val Gly Ser Ile Arg Tyr Asn Tyr Leu Leu Asp
225                   230                   235                   240

Val Leu Glu Arg Ser Pro His Arg Pro Ile Leu Gln Ala Gly Leu Pro
                245                   250                   255

Ala Asn Thr Thr Ala Val Val Gly Ser Asp Val Glu Leu Leu Cys Lys
            260                   265                   270

Val Tyr Ser Asp Ala Gln Pro His Ile Gln Trp Leu Lys His Ile Val
            275                   280                   285

Ile Asn Gly Ser Ser Phe Gly Ala Asp Gly Phe Pro Tyr Val Gln Val
            290                   295                   300

Leu Lys Thr Ala Asp Ile Asn Ser Ser Glu Val Glu Val Leu Tyr Leu
305                   310                   315                   320

Arg Asn Val Ser Ala Glu Asp Ala Gly Glu Tyr Thr Cys Leu Ala Gly
                325                   330                   335

Asn Ser Ile Gly Leu Ser Tyr Gln Ser Ala Trp Leu Thr Val Leu Pro
            340                   345                   350
```